United States Patent
Kumar et al.

(10) Patent No.: US 12,427,174 B2
(45) Date of Patent: Sep. 30, 2025

(54) PROBIOTIC COMPOSITIONS COMPRISING LACTOBACILLUS REUTERI STRAINS AND METHODS OF USE

(71) Applicant: ELANCO US INC., Greenfield, IN (US)

(72) Inventors: Arvind Kumar, Fishers, IN (US); Dharanesh Mahimapura Gangaiah, Fishers, IN (US)

(73) Assignee: BIOMEDIT, INC., Fishers, IN (US)

( * ) Notice: Subject to any disclaimer, the term of this patent is extended or adjusted under 35 U.S.C. 154(b) by 871 days.

(21) Appl. No.: 17/428,510

(22) PCT Filed: Feb. 4, 2020

(86) PCT No.: PCT/US2020/016668
§ 371 (c)(1),
(2) Date: Aug. 4, 2021

(87) PCT Pub. No.: WO2020/163398
PCT Pub. Date: Aug. 13, 2020

(65) Prior Publication Data
US 2022/0125860 A1    Apr. 28, 2022

Related U.S. Application Data

(60) Provisional application No. 62/801,307, filed on Feb. 5, 2019.

(51) Int. Cl.
*A61K 35/747* (2015.01)
*A23K 10/18* (2016.01)
(Continued)

(52) U.S. Cl.
CPC ............ *A61K 35/747* (2013.01); *A23K 10/18* (2016.05); *A23K 20/163* (2016.05); *A23K 50/75* (2016.05); *A23L 33/135* (2016.08); *A61K 35/742* (2013.01); *A61P 1/00* (2018.01); *A61P 31/04* (2018.01); *C07K 16/1282* (2013.01); *C12N 1/205* (2021.05); *C12N 15/746* (2013.01); *A23V 2002/00* (2013.01); *A23V 2400/173* (2023.08);
(Continued)

(58) Field of Classification Search
None
See application file for complete search history.

(56) References Cited

U.S. PATENT DOCUMENTS

2015/0150917 A1 * 6/2015 Connolly ............... C12Q 1/689
506/4

FOREIGN PATENT DOCUMENTS

| CN | 105219683 A | * | 1/2016 | |
| CN | 104684408 B | * | 8/2018 | ............. A23K 10/18 |
| WO | 2013184064 A1 | | 12/2013 | |

OTHER PUBLICATIONS

Anonymous: "UPI000F4E49B8 Lactobacillus reuteri sequence", , Nov. 24, 2018 (Nov. 24, 2018), XP055695267, URL:https://www.uniprot.org/uniparc/UPIOOOF4E49B8 (Year: 2018).*

(Continued)

*Primary Examiner* — Sharmila G Landau
(74) *Attorney, Agent, or Firm* — Hoffmann & Baron LLP

(57) ABSTRACT

The present invention relates to probiotic compositions and methods for increasing animal health. The probiotic compositions include one or more isolated strains of novel *Lactobacillus reuteri* strains which colonizes the gastrointestinal tract to increase the health of an animal.

31 Claims, 19 Drawing Sheets
Specification includes a Sequence Listing.

(51) Int. Cl.
- A23K 20/163 (2016.01)
- A23K 50/75 (2016.01)
- A23L 33/135 (2016.01)
- A61K 35/742 (2015.01)
- A61P 1/00 (2006.01)
- A61P 31/04 (2006.01)
- C07K 16/12 (2006.01)
- C12N 1/20 (2006.01)
- C12N 15/74 (2006.01)
- A61K 38/00 (2006.01)
- C07K 14/32 (2006.01)
- C07K 14/335 (2006.01)
- C12R 1/225 (2006.01)

(52) U.S. Cl.
CPC .............. A61K 38/00 (2013.01); C07K 14/32 (2013.01); C07K 14/335 (2013.01); C07K 2317/22 (2013.01); C07K 2317/76 (2013.01); C07K 2319/02 (2013.01); C07K 2319/035 (2013.01); C12R 2001/225 (2021.05)

(56) References Cited

OTHER PUBLICATIONS

Wang et al., "Coexpression and Secretion of Endoglucanase and Phytase Genes in Lactobacillus reuteri", Int. J. Mol. Sci. 2014, 15, 12842-12860; doi:10.3390/ijms150712842). (Year: 2014).*

M'Sadeq, SA; et al. "Towards the control of necrotic enteritis in broiler chickens with in-feed antibiotics phasing-out worldwide", Animal Nutrition, vol. 1, Issue 1, 2015, pp. 1-11, https://doi.org/10.1016/j.aninu.2015.02.004. (Year: 2015).*

Zhang, Dexian, Rui Li, and Jichang Li. "Lactobacillus reuteri ATCC 55730 and L22 display probiotic potential in vitro and protect against Salmonella-induced pullorum disease in a chick model of infection." Research in veterinary science 93.1 (2012): 366-373.

Aalaei, Maryam, et al. "Comparison of single-and multi-strain probiotics effects on broiler breeder performance, egg production, egg quality and hatchability." British poultry science 59.5 (2018): 531-538.

De Moreno de LeBlanc, Alejandra, et al. "Current review of genetically modified lactic acid bacteria for the prevention and treatment of colitis using murine models." Gastroenterology research and practice 2015 (2015).

Mappley, Luke J., et al. "Oral treatment of chickens with Lactobacillus reuteri LM1 reduces Brachyspira pilosicoli-induced pathology." Journal of medical microbiology 62.2 (2013): 287-296.

Wang, Tianwei, et al. "Lactobacillus reuteri HCM2 protects mice against Enterotoxigenic Escherichia coli through modulation of gut microbiota." Scientific reports 8.1 (2018): 1-14.

Wang, Lei, et al. "Characterization of the most abundant Lactobacillus species in chicken gastrointestinal tract and potential use as probiotics for genetic engineering." Acta Biochim Biophys Sin 46.7 (2014): 612-619.

Duar, Rebbeca M., et al. "Experimental evaluation of host adaptation of Lactobacillus reuteri to different vertebrate species." Applied and environmental microbiology 83.12 (2017): e00132-17.

Mu, Qinghui, Vincent J. Tavella, and Xin M. Luo. "Role of Lactobacillus reuteri in human health and diseases." Frontiers in microbiology 9 (2018): 757.

Hou, Chengli, et al. "Study and use of the probiotic Lactobacillus reuteri in pigs: a review." Journal of animal science and biotechnology 6.1 (2015): 1-8.

Börner, Rosa A., et al. "Genome editing of lactic acid bacteria: opportunities for food, feed, pharma and biotech." FEMS microbiology letters 366.1 (2019): fny291.

Anonymous: "UPI000F4E49B8 Lactobacillus Reuteri Sequence," Nov. 24, 2018, retrieved from the Internet: URL: https://www.uniprot.org/uniparc/UPI000F4E49B8 (retreived on May 14, 2020).

* cited by examiner

PROBIOTIC COMPOSITIONS COMPRISING LACTOBACILLUS REUTERI STRAINS AND METHODS OF USE

CROSS-REFERENCE TO RELATED APPLICATIONS

This application is a National Stage Application claiming priority from co-pending PCT Application No. PCT/US2020/016668 filed on 4 Feb. 2020, which in turn claims priority to U.S. Provisional Application No. 62/801,307, filed on 5 Feb. 2019, the contents of which are hereby incorporated by reference.

SEQUENCE LISTING

This application contains a Sequence Listing, which was submitted in ASCII format via EFS-Web, and is hereby incorporated by reference in its entirety. The ASCII copy, created on 4 Feb. 2020, is named "X30027-SeqListing ST25.txt" and is 121 KB in size.

FIELD OF THE INVENTION

The present invention relates to probiotic compositions and methods for improving animal health. The probiotic compositions include one or more isolated strains of *Lactobacillus* sp which colonizes the gastrointestinal tract to increase the health of an animal.

BACKGROUND OF THE INVENTION

Direct fed microbials (DFMs), often also called probiotics, are microorganisms which colonize the gastrointestinal tract of an animal and provide some beneficial effect to that animal. The microorganisms can be bacterial species, for example those from the genera *Bacillus, Lactobacillus, Lactococcus*, and *Entercoccus*. The microorganisms can also be yeast or even molds. The microorganisms can be provided to an animal orally or mucosally or, in the case of birds, provided to a fertilized egg, i.e. in ovo.

The beneficial activity provided by a DFM can be the synthesis of vitamins or other nutritional molecules needed for a healthy metabolism of the host animal. A DFM can also protect the host animal from disease, disorders, or clinical symptoms caused by other, pathogenic microorganisms. For example, the DFM may naturally produce factors having inhibitory or cytotoxic activity against certain species of pathogens, such as deleterious or disease-causing bacteria.

There is a need in the art for probiotic compositions and methods that provide improved delivery of beneficial molecules to the gastrointestinal tract of an animal and improve animal health.

SUMMARY OF THE INVENTION

The present invention provides compositions and methods for improving animal health.

In one embodiment, the invention provides a composition having at least one of an isolated first *Lactobacillus reuteri* strain and an isolated second *Lactobacillus reuteri* strain, wherein said composition increases animal health when an effective amount is administered to an animal, as compared to an animal not administered the composition.

In one embodiment, the first isolated first *Lactobacillus reuteri* strain includes at least one of: a nucleic acid sequence having at least 95%, at least 96%, at least 97%, at least 98%, or at least 99% sequence identity with SEQ ID NO:26, a nucleic acid sequence having at least 95%, at least 96%, at least 97%, at least 98%, or at least 99% sequence identity with SEQ ID NO: 1, a nucleic acid sequence having at least 95%, at least 96%, at least 97%, at least 98%, or at least 99% sequence identity with SEQ ID NO: 3, and a nucleic acid that encodes for an amino acid sequence having at least 95%, at least 96%, at least 97%, at least 98%, or at least 99% sequence identity with SEQ ID NO: 8.

In one embodiment, the second isolated second *Lactobacillus reuteri* strain includes at least one of: a nucleic acid sequence having at least 95%, at least 96%, at least 97%, at least 98%, or at least 99% sequence identity with SEQ ID NO:25, a nucleic acid sequence having at least 95%, at least 96%, at least 97%, at least 98%, or at least 99% sequence identity with SEQ ID NO: 27, a nucleic acid sequence having at least 95%, at least 96%, at least 97%, at least 98%, or at least 99% sequence identity with SEQ ID NO: 28, and a nucleic acid sequence having at least 95%, at least 96%, at least 97%, at least 98%, or at least 99% sequence identity with SEQ ID NO: 29.

In one embodiment, the invention provides a method of increasing animal health. The method includes administering an effective amount of the above composition to an animal.

BRIEF DESCRIPTION OF THE DRAWINGS

FIG. 11A represents the cell pellet of the culture, 1_P-30 is the pellet from strain 3630, 2_P-32 is the pellet from strain 3632, and 3_P-30-32 is the pellet from a co-culture of strain 3630 and strain 3632.

FIG. 11B represents the supernatant of the culture, 1_S-30 is the supernatant from strain 3630, 2_S-32 is the supernatant from strain 3632, and 3_S-30-32 is the supernatant from a co-culture of strain 3630 and strain 3632. 4 Medial is AOF-MRS media control with no glucose but 0.5% GOS.

For FIGS. 12-19, data represents subject molecule that is secreted into the supernatant. 1) *Lactobacillus reuteri* strain 3630, 2) *Lactobacillus reuteri* strain 3632, 3) co-culture of *Lactobacillus reuteri* strain 3630 and *Lactobacillus reuteri* strain 3632, and 4) media control. Data are scaled such that the median value measured across all samples was set to 1.0.

Figure 12:
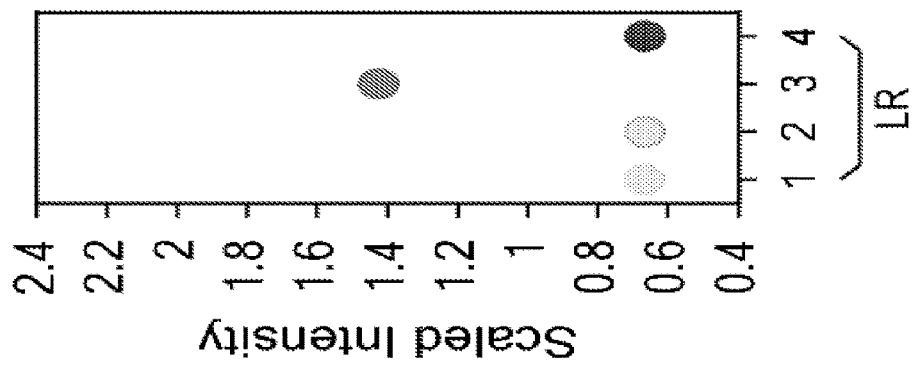
Figure 12:
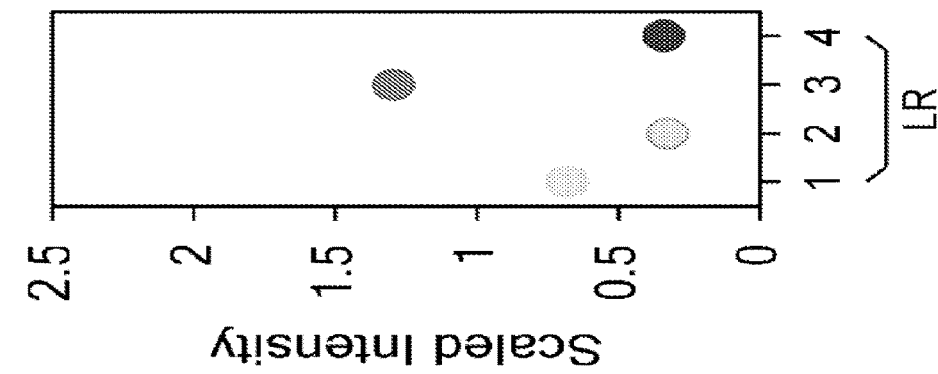
Figure 12:
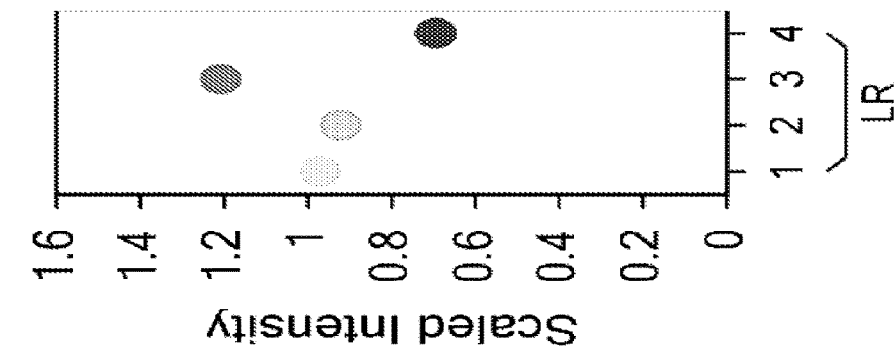

FIG. 12 depicts levels of dimethylglycine, allo-threonine, and 1-methyl-4-imidazoleacetate secreted by *Lactobacillus reuteri* strains.

Figure 13:
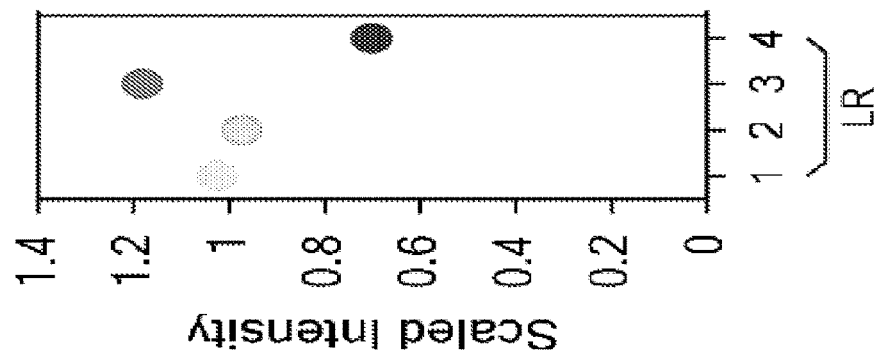
Figure 13:
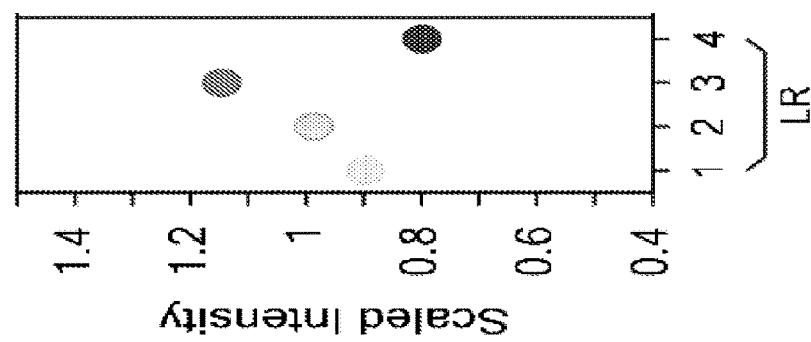
Figure 13:
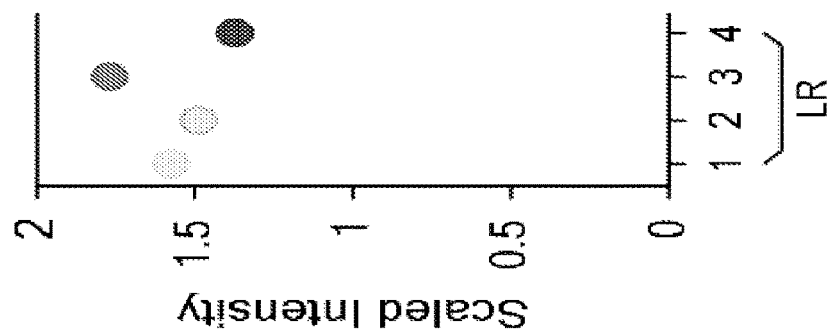

FIG. 13 depicts levels of 4-imidazoleacetate, lysine, and N6-methyllysine secreted by *Lactobacillus reuteri* strains.

Figure 14:
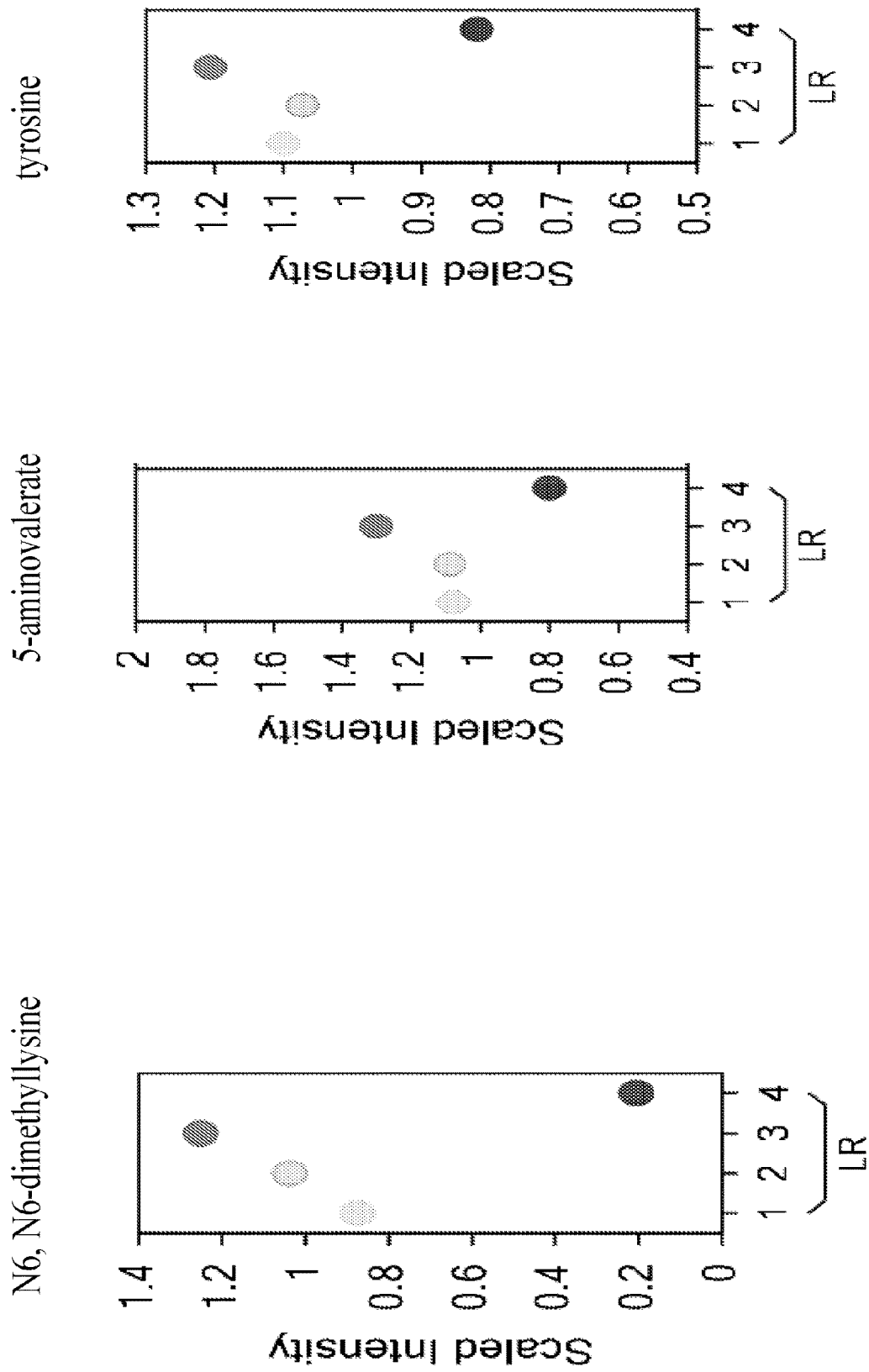

FIG. 14 depicts levels of N6, N6-dimethyllysine, 5-aminovalerate, and tyrosine secreted by *Lactobacillus reuteri* strains.

Figure 15:
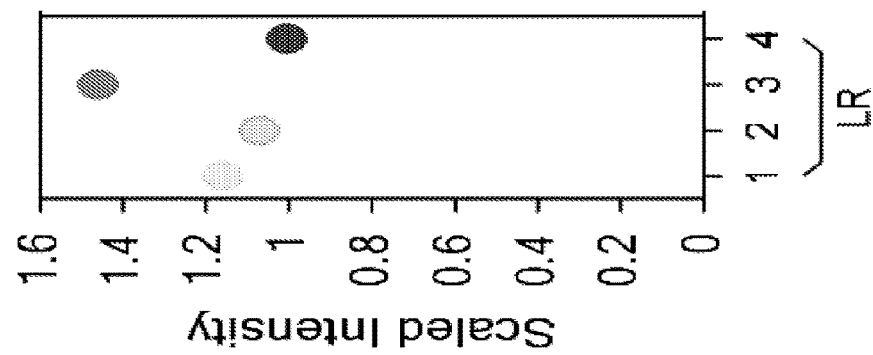
Figure 15:
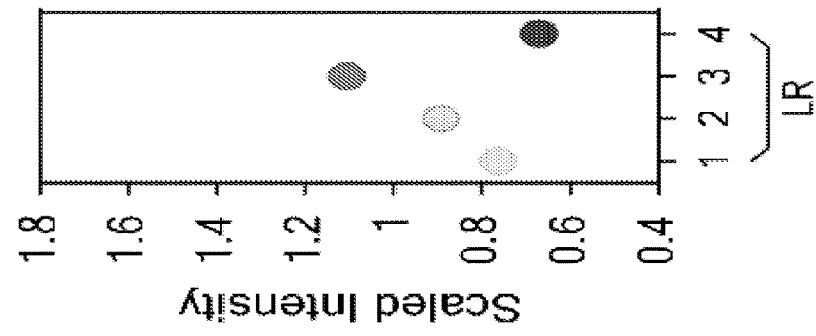
Figure 15:
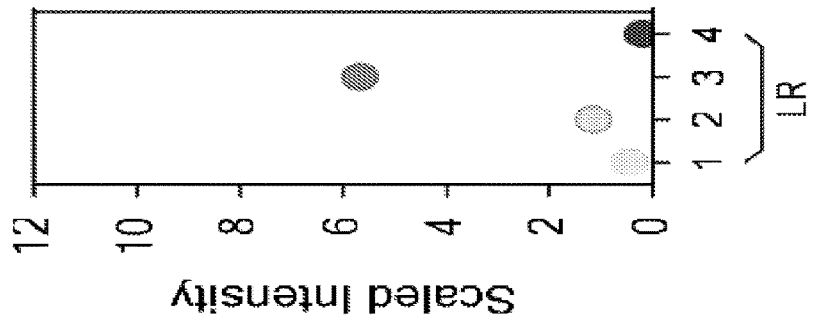

FIG. 15 depicts levels of 4-hydroxyphenylpyruvate, indolacetate, and gamma-glutamylglutamine secreted by *Lactobacillus reuteri* strains.

Figure 16:
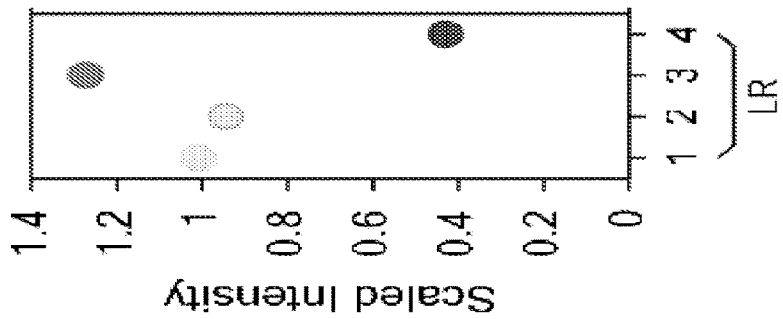
Figure 16:
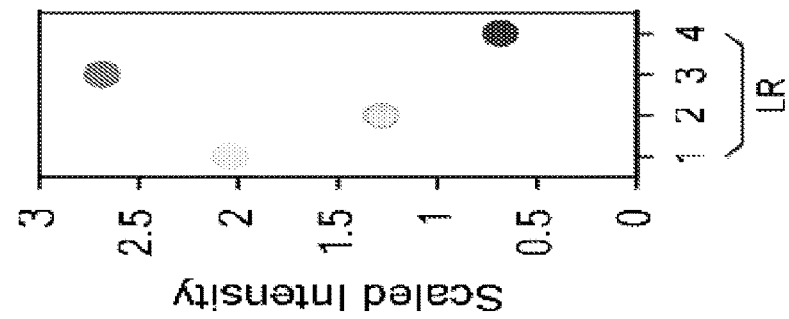
Figure 16:
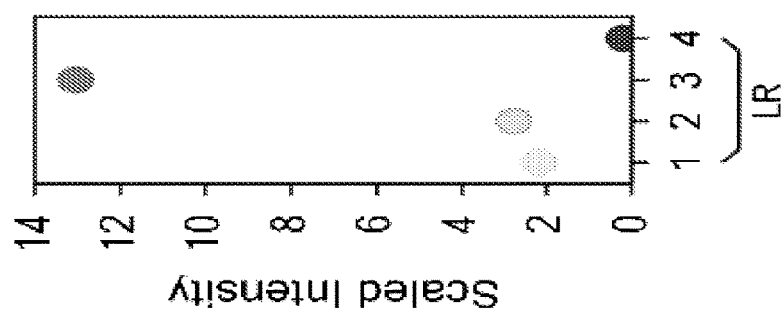

FIG. 16 depicts levels of glucose 6-phosphate, 4-hydroxyl-2-oxoglutaric acid, and myo-inositol secreted by *Lactobacillus reuteri* strains.

Figure 17:
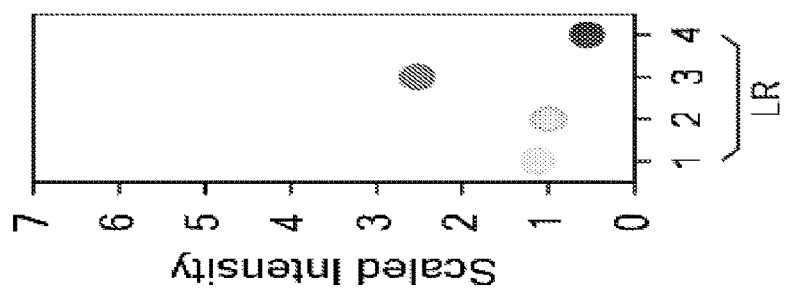
Figure 17:
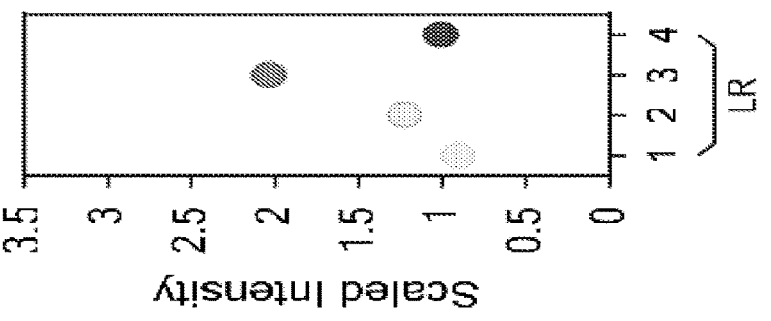
Figure 17:
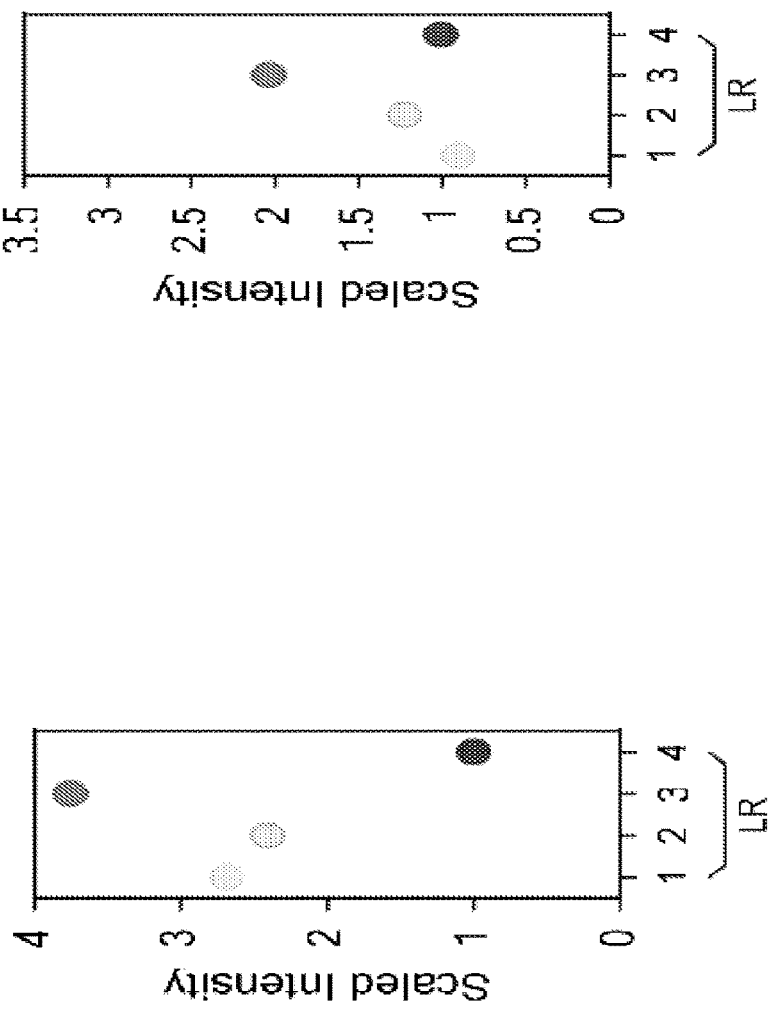

FIG. 17 depicts levels of Uridine 5'-monophosphate (UMP), Cytidine 5'-monophosphate (5'-CMP), and 3'-5'-uridylyluridine secreted by *Lactobacillus reuteri* strains.

Figure 18:
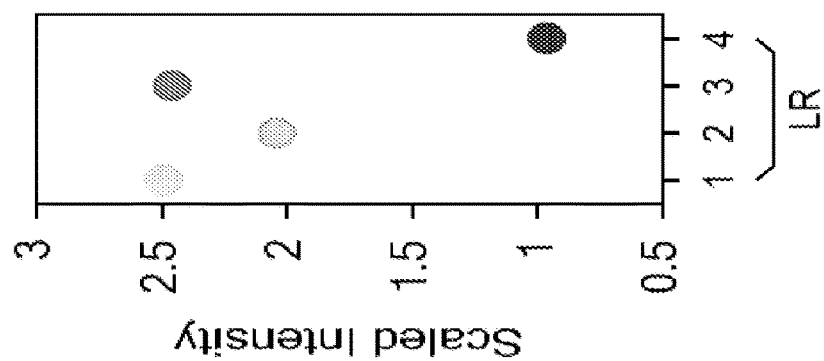
Figure 18:
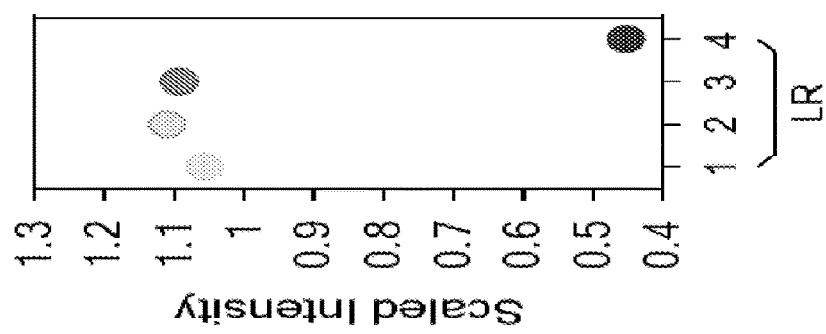
Figure 18:
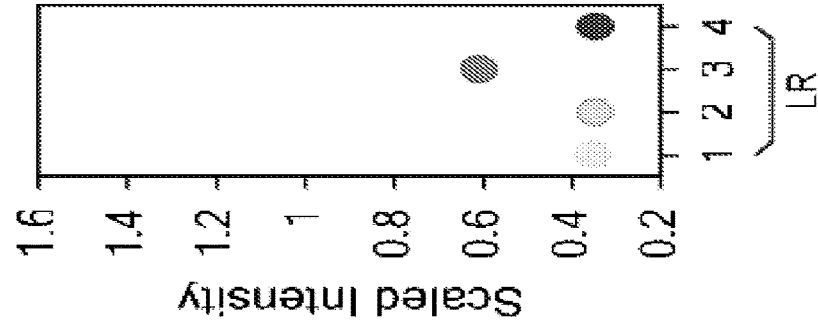

FIG. 18 depicts levels of O-sulfo-L-tyrosine, indole 3 acetamide, and indolin-2-one secreted by *Lactobacillus reuteri* strains.

Figure 19:
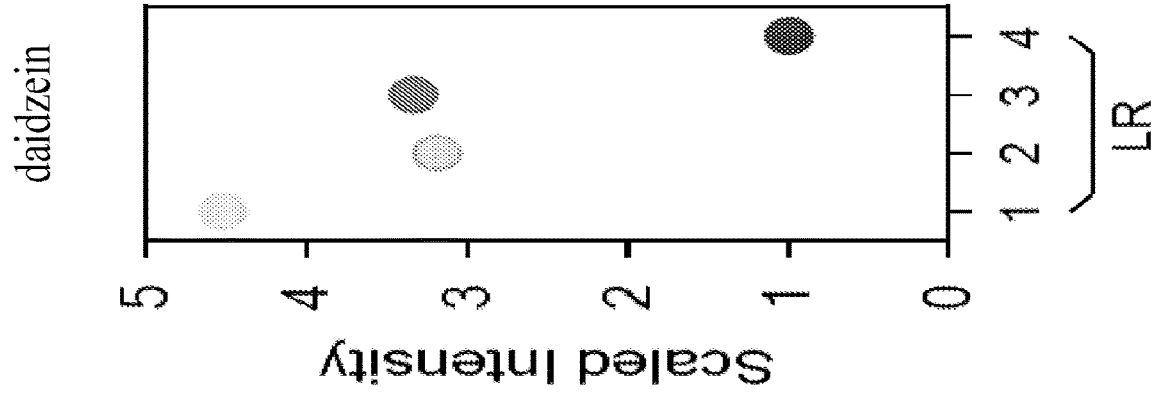

FIG. 19 depicts levels of daidzein secreted by *Lactobacillus reuteri* strains.

DETAILED DESCRIPTION OF THE INVENTION

The present invention provides compositions and methods for increasing animal health.

In one embodiment, the invention provides a composition having at least one of an isolated first *Lactobacillus reuteri* strain and an isolated second *Lactobacillus reuteri* strain.

In one embodiment, the isolated first *Lactobacillus reuteri* strain is strain 3632. As disclosed herein, strain 3632 has a nucleic acid or amino acid sequence including at least one of SEQ ID NOs: 1-24 and 26, sequences having at least 95%, at least 96%, at least 97%, at least 98%, or at least 99% sequence identity with at least one of SEQ ID NOs: 1-24 and 26. *Lactobacillus reuteri* strain 3632 was deposited on 19 Jun. 2020 according to the Budapest Treaty in the American Type Culture Collection (ATCC), ATCC Patent Depository, 10801 University Boulevard, Manassas, Va., 20110, USA. The deposit has been assigned ATCC Patent Deposit Number PTA-126788.

In one embodiment, the isolated second *Lactobacillus reuteri* strain is strain 3630. As disclosed herein, strain 3630 has a nucleic acid sequence including at least one of SEQ ID NOS: 25 and 27-43, sequences having at least 95%, at least 96%, at least 97%, at least 98%, or at least 99% sequence identity with at least one of SEQ ID NOs: 25 and 27-43. *Lactobacillus reuteri* strain 3630 was deposited on 19 Jun. 2020 according to the Budapest Treaty in the American Type Culture Collection (ATCC), ATCC Patent Depository, 10801 University Boulevard, Manassas, Va. 20110, USA. The deposit has been assigned ATCC Patent Deposit Number PTA-126787.

The isolated strains of the present disclosure are not genetically modified by recombinant or genetically engineered means.

In some embodiments, the composition disclosed herein includes an isolated first *Lactobacillus reuteri* strain and an isolated second *Lactobacillus reuteri* strain at a ratio of approximately 0.75-1.5:1. In a preferred embodiment, the composition includes about equal amounts of the isolated first *Lactobacillus reuteri* strain and the isolated second *Lactobacillus reuteri* strain.

The compositions disclosed herein can be formulated as animal feed, feed additive, food ingredient, water additive, water-mixed additive, consumable solution, consumable spray additive, consumable solid, consumable gel, injection, or combinations thereof. In one embodiment, the composition includes water.

The compositions disclosed herein includes the isolated first *Lactobacillus reuteri* strain in an amount of about 10^2-10^8 CFU/kg of the composition, about 10^4-10^7 CFU/kg of the composition, about 10^3-10^5 CFU/kg of the composition, about 10^2 CFU/kg of the composition, about 10^3 CFU/kg of the composition, or about 10^7 CFU/kg of the composition.

The compositions of the disclosure exhibit markedly different functional and/or structural characteristics/properties, as compared to their closest naturally occurring counterpart. For instance, the *Lactobacillus reuteri* strain of the disclosure are structurally different from a *Lactobacillus reuteri* strain as it naturally exists in a gastrointestinal tract. To elaborate, the *Lactobacillus reuteri* strain can be isolated and purified, such that it is not found in the milieu of the gastrointestinal tract, the *Lactobacillus reuteri* strain can be present at concentrations that do not occur in the gastrointestinal tract, the *Lactobacillus reuteri* strain can be associated with acceptable carriers that do not occur in the gastrointestinal tract, the *Lactobacillus reuteri* strain can be formulated to be shelf-stable and exist outside the gastrointestinal tract, and said microbe can be combined with other microbes at concentrations that do not exist in the gastrointestinal tract. Further, the *Lactobacillus reuteri* strain of the disclosure are functionally different from a *Lactobacillus reuteri* strain as it naturally exists in a gastrointestinal tract. To elaborate, the *Lactobacillus reuteri* strain when applied in an isolated and purified form can lead to modulation of the gastrointestinal microbiome, increased weight gain, increased feed utilization, decreased amounts of microbial pathogens, and decreased pathogen-associated gastro-intestinal lesions.

Method

The present disclosure also provides methods of increasing animal health, wherein the method includes administering an effective amount of the composition to an animal.

The composition disclosed herein and above increases animal health by providing positive health benefits when administered to an animal, as compared to an animal that has not been administered the composition. As used herein, "animal" includes bird, poultry, a human, or a non-human mammal. Specific examples include chickens, turkey, dogs, cats, cattle and swine. The chicken may be a broiler chicken or egg-laying or egg-producing chicken.

Positive health benefits include decreasing feed conversion ratio, increasing weight, increasing lean body mass, decreasing pathogen-associated lesion formation in the gastrointestinal tract, decreasing colonization of pathogens, reducing inflammation, and decreasing mortality rate.

In some embodiments, the compositions disclosed herein decreases feed conversion ratio by at least 1%, at least 5%, at least 25%, or at least 50%. In some embodiments, the compositions disclosed herein increases poultry weight by at least 1%, at least 5%, at least 25%, or at least 50%. In some embodiments, the compositions disclosed herein decrease pathogen-associated lesion formation in the gastrointestinal tract by at least 1%, at least 5%, at least 25%, or at least 50%. In some embodiments, the compositions disclosed herein decrease pathogen colonization by at least 1%, at least 5%, at least 25%, or at least 50%. In some embodiments, the compositions disclosed herein reduce inflammation by at least 1%, at least 5%, at least 25%, or at least 50%. In some embodiments, the compositions disclosed herein decrease mortality rate by at least 1%, at least 5%, at least 25%, or at least 50%.

In some embodiments, following values may be combined in any manner to create a minima, a maxima, or a range for decreasing feed conversion ratio, increasing poultry weight, increasing lean body mass, decreasing pathogen-associated lesion formation in the gastrointestinal tract, decreasing colonization of pathogens, and decreasing mortality rate, 1%, 5%, 25%, 50%, and 75%.

For example, the decrease in pathogen-associated lesion formation may be decreased by approximately 1% to 5%, and more preferably between approximately 5% to 50%.

As used herein, pathogen includes *Salmonella, Clostridium, Campylobacter, Staphylococcus, Streptococcus*, and *E. coli* bacterium. Further examples of pathogens include *Salmonella typhimurium, Salmonella infantis, Salmonella Hadar, Salmonella enteritidis, Salmonella Newport, Salmonella Kentucky, Clostridium perfringens, Staphylococcus aureus, Streptoccus uberis, Streptococcus suis, Escherichia coli, Campylobacter jejuni*, and *Fusobacterium necrophorum*.

The compositions may be administered orally, parentally, nasally, or mucosally.

In some aspects, administration includes feeding the poultry, or spraying onto the poultry. In other aspects, administration includes on ovo administration or in ovo administration, In some aspects the animal is vaccinated in conjunction with administration. The animal may be vaccinated prior to administration of the compositions disclosed herein. The animal may be vaccinated with an coccidiosis vaccine. Coccidiosis vaccines are known in the art, for example, COCCIVAC.

In some embodiments, administration is by way of injection or infusion. In one embodiment, the composition is administered to a cow by way of intra-mammary infusion.

The strains disclosed herein demonstrate certain phenotypic properties. Without wishing to be bound by theory, it is believed that these phenotypic properties at least contribute to increasing animal health.

In some embodiments, the isolated strains secrete at least one of cyclic dipeptides (cyclo(his-phe) and cyclo (phe-pro), short chain fatty acids (2-hydroxy-3-methylvalerate and alpha-hydroxyisocaproate), betaine, dimethylglycine, essential amino acids (e.g., allo-threonine, phosphothreonine, histidine, lysine, phenylalanine, tryptophan, leucine, isoleucine, and cysteine s-sulfate), nucleotides (e.g., adenosine 5'-monophosphate (AMP), uridine 5'-monophosphate (UMP), cytidine 5'-monophosphate (5'-CMP), and cytidine 2'3'-cyclicmonophosphate), myo-inositol, and indolin-2-one. Some of the aforementioned molecules provide beneficial characteristics to the host, including increased weight, pro-inflammatory effects, and antibiotic effects.

In some embodiments, the composition including the isolated first *Lactobacillus reuteri* strain (strain 3632) and the isolated second *Lactobacillus reuteri* strain (strain 3630) in combination, will secrete certain beneficial molecules in larger quantities than when individually cultured. See for example, FIGS. 12-19.

In some embodiments, the animal administered the composition exhibits a shift in the microbiome content of the gastrointestinal tract. For example, there may be an increase in the amount of bacteroidaceae bacteria in the gut of an animal that has been administered the composition described herein, as compared to an animal that was not administered the composition.

In some embodiments, the invention provides a method of treating, ameliorating the effects of, or preventing necrotic enteritis in an animal by administering a composition disclosed herein to an animal in need thereof.

In some embodiments, the invention provides a method of treating, ameliorating the effects of or preventing bovine mastitis. The method includes administering a composition disclosed herein to an animal in need thereof.

As used herein, "isolated" means that the subject isolate has been separated from at least one of the materials with which it is associated in a particular environment.

Thus, an "isolate" does not exist in its naturally occurring environment; rather, it is through the various techniques described herein that the microbe has been removed from its natural setting and placed into a non-naturally occurring state of existence. Thus, the isolated strain or isolated microbe may exist as, for example, a biologically pure culture in association with an acceptable carrier.

As used herein, "individual isolates" should be taken to mean a composition, or culture, comprising a predominance of a single genera, species, or strain, of microorganism, following separation from one or more other microorganisms. The phrase should not be taken to indicate the extent to which the microorganism has been isolated or purified.

However, "individual isolates" can comprise substantially only one genus, species, or strain, of microorganism.

In certain aspects of the disclosure, the isolated *Lactobacillus reuteri* strain exist as isolated and biologically pure cultures. It will be appreciated by one of skill in the art, that an isolated and biologically pure culture of a particular *Lactobacillus reuteri* strain, denotes that said culture is substantially free (within scientific reason) of other living organisms and contains only the individual *Lactobacillus reuteri* strain in question. The culture can contain varying concentrations of said isolated *Lactobacillus reuteri* strain. The present disclosure notes that isolated and biologically pure microbes often necessarily differ from less pure or impure materials.

In embodiments of the present invention, the composition includes a combination of two isolated *Lactobacillus reuteri* strains.

As used herein, "carrier", "acceptable carrier", or "pharmaceutical carrier" refers to a diluent, adjuvant, excipient, or vehicle with which the compound is administered. Such carriers can be sterile liquids, such as water and oils, including those of petroleum, animal, vegetable, or synthetic origin; such as peanut oil, soybean oil, mineral oil, sesame oil, and the like. Water or aqueous solution saline solutions and aqueous dextrose and glycerol solutions are preferably employed as carriers, in some embodiments as injectable solutions. Alternatively, the carrier can be a solid dosage form carrier, including but not limited to one or more of a binder (for compressed pills), a glidant, an encapsulating agent, a flavorant, and a colorant. The choice of carrier can be selected with regard to the intended route of administration and standard pharmaceutical practice. See Hardee and Baggo (1998. Development and Formulation of Veterinary Dosage Forms. 2nd Ed. CRC Press. 504 pg.); and E. W. Martin (1970. Remington's Pharmaceutical Sciences. 17th Ed. Mack Pub. Co.).

As used herein, "delivery" or "administration" means the act of providing a beneficial activity to a host. The delivery may be direct or indirect. An administration could be by an oral, nasal, or mucosal route. For example without limitation, an oral route may be an administration through drinking water, a nasal route of administration may be through a spray or vapor, and a mucosal route of administration may be through direct contact with mucosal tissue. Mucosal tissue is a membrane rich in mucous glands such as those that line the inside surface of the nose, mouth, esophagus, trachea, lungs, stomach, gut, intestines, and anus. In the case of birds, administration may be in ovo, i.e. administration to a fertilized egg. In ovo administration can be via a liquid which is sprayed onto the egg shell surface, or an injected through the shell.

As used herein, the terms "treating", "to treat", or "treatment", include restraining, slowing, stopping, reducing, ameliorating, or reversing the progression or severity of an existing symptom, disorder, condition, or disease. A treatment may also be applied prophylactically to prevent or reduce the incidence, occurrence, risk, or severity of a clinical symptom, disorder, condition, or disease.

Unless expressly stated to the contrary, "or" refers to an inclusive "or" and not to an exclusive "or". For example, a condition A or B is satisfied by any one of the following: A is true (or present) and B is false (or not present), A is false (or not present) and B is true (or present), and both A and B are true (or present).

Any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment." In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any one, two, three, or four of the members, e.g., a and c; a, d, and e; b, c, d, and e; etc.

Throughout this specification, quantities are defined by ranges, and by lower and upper boundaries of ranges. Each lower boundary can be combined with each upper boundary to define a range. The lower and upper boundaries should each be taken as a separate element. Two lower boundaries or two upper boundaries may be combined to define a range.

```
SEQUENCE LISTING
mersacidin-E1 cDNA
                                                                    SEQ ID NO: 1
    1 atggacaaag aagaattaga aaaaattgta ggtaataact ttgaggaaat gagtttacaa 61 aaaatgacag aaattcaagg tatgggtgaa taccaagtgg attcaacacc agcagcttct 121 gcgatttcac gggcaacaat tcaagtatca cgtgcatctt ctggaaaatg tctaagttgg 181 ggtagtggtg cagcatttag tgcttatttt actcataaaa gatggtgcta g mersacidin-E1 amino acid (natural)
                                                                    SEQ ID NO: 2
    1 MDKEELEKIV GNNFEEMSLQ KMTEIQGMGE YQVDSTPAAS AISRATIQVS RASSGKCLSW

61 GSGAAFSAYF THKRWC mersacidin-E2 cDNA
                                                                    SEQ ID NO: 3
    1 atggaagaaa aagaattaga aggtgtaata gggaattcgt ttgaaagtat gactgtagag 61 gaaatgacaa aaattcaagg tatgggtgaa tatcaagtag attcgacgcc tggatatttt
```

-continued

```
121 atggaaagtg ctgccttttc agctcttaca gccaatataa caagacatgc tatgcatcat 181 cattaa
``` mersacidin-E2 amino acid (natural)
SEQ ID NO: 4
```
  1 MEEKELEGVI GNSFESMTVE EMTKIQGMGE YQVDSTPGYF MESAAFSALT ANITRHAMHH

61 H
```

Capreomycidine synthase (natural).
SEQ ID NO: 5
```
  1 MVEIAHFGVE AWLNKWEKSA TYDISQSTIA SLSMHDLLNL DGNNGEEFYE MLDKQQMNYG

61 WIEGSPEFKE EVAKLYHHVD PENILQTNGA TGANILALYA LINPGDHVIA EYPSYQQLYD

121 IPKSLGADVD YWHIHEEDNW YPRIDDLKAM VKPNTKMICL NNANNPTGTV LDKEFLEQVV

181 EIAKSVDAYV LVDEVYLPLD HPEKFAQIID LYDKGISTNS LSKTYSVPGV RIGWTATNAE

241 VADIFRKFRD YTMICGGVFN DQLATYVLRH RDQVLARNRK LVLGNLAIYK DWIDHEDRAS

301 VIMPQAVSTS FPKLDVPVDI HTFCENLLHD EGVLLVPGDA FDTPGHVRLG YCAPEATLKE

361 GLKRLSKYMH QYD
```

Colicin V production protein (natural).
SEQ ID NO: 6
```
  1 MILTTFIILI LMGCFINGHR RGLLTMTLML GTYIVAWIVA RQGAQLIGGW LKSLLPSIGT

61 PATFSESLLA NVNSNLFFYN GIAFMIIFTI VSILCHWGIR QLNWIKRIPV VGTVDKIAGG

121 LISFLIGYLI IYVVLLIMQL FPAGWWQMQI ANSELARFMI NQTPGIAHLV IDTLVQGG
```

Agglutinin receptor precursor-1 (ARP-1) (natural)
SEQ ID NO: 7
```
  1 MNEYNAEMAK LNQGANAPVI TTNSVNQALS LKPENNATVD IEALNPRITF KRVEEGTKYA

61 GYQIFDKNNA YVNNIDGEFL RVTYTNLKNS TYKGSKISKI VVTYSDSTPT GNRITQSGLN

121 AVTEGANDNF LVVFEDPVRG DMHSTTVTAT YQYYDANGNL IDFSGTNNAW LSVGSLNFDQ

181 GNDYQGGKNE GNPTSGISEG VKLISGAQIK QLAGSSISVH DDGWAYAGFN NYSGTGMNNG

241 INTDNGGSGW DMDGSPNAYY GAIVFQLTGS SVSLRQGLVS WGGADIASQY NNQFLNNAWF

301 TAGTTLPETQ IKQPIRKTSE THYHYNPSVI RL
```

Agglutinin receptor precursor-2 (ARP-2) (natural)
SEQ ID NO: 8
```
  1 MAQKLMSANS TDKNFKMYKS KKSWVFAYST TLALAAVAGI TLSTTNVHAD TTNGGDNQVN

61 ATAVTQNTTS NTVDQIAANT AQTDNTSTSI NIRSLMDDLA SGDDTSSSQN GQEQSQNYAS

121 SNQNSQTQQE NGTTGQSTAS QNGTTSDQTN SDQSDKNYYV ISTRDLDKNG NVNYLTQKNY

181 TSIKGQEVAD GTVVTWPLSV SALPANRAQD LKSHVISETL DPHLEYLHYR AYLTNTDGTV

241 TDVTNHVNLN RSGQTLIFTD DNYLLSIYNN NRYRVQNLPV IKLVTKANGN GYIIPNAFKS

301 SYVFNDGSHD VSFTTTSNNV QIKTFNPGNS KDVEIGGNVQ GDPSGTINGQ VVADGSVVTW

361 PMSVGDLPAN RAQDVLSHIE TDTLYNGLNY EGYHAYLPQA DGSFQDVSSH INVQQNGQDL

421 TFIADDYLIG LYNQDKSTAF KMPIIDLITS VHGTSIIAPN KFNSQLAFKD GNGQTVINNT

481 SNQVQISTYH PTNTKDVELG GNVQGDTPNS INDKVVANGA IVTWPMASSE LPANRVQDLQ

541 SRVISETLDS HLQYQGYKAW LQNADGKYTD VTSHVKLTQD GQNLTFADDE YLLNLYNSNK

601 GTAYKLPIID LVTKVNGAGI TAPNSYTTKY VYSDGDGNTT INVTSNTVKI STFNPTTNKD

661 VELGDNIHGD TESSIAGKLV SEGTIVTWPL STSDLPANRA QDVVSHTAVD ALEPTLQYIS

721 YTAWLPDSNG QLQDVTSHVK MTRDGQKLTF TDDDYLIGLY NQNKDIALKM PIIDLVTKAT

781 GNTKLLPNSF DSQFVYNDVD GNTIINVSSN KPTVETFDPT VHKDVELGGN NVQGDTPNSI

841 DGKIVAQGTV VTWPMSTSDL PANRTQDVVS HSTSETLNQN LQYVGYHAYM PDANGKLQDV

901 TSHVQLQQNG QNLVFTDDSY LINLYNQDKS LAFKMPIIDL MTKAISDSAT IPNTFESQYV
```

-continued

```
 961 FNDGNGNTTF KSTSNTVQII TYKPKTTKDV ELGDNIHGDT NASIAGQMIT DGTVVTWPMS

1021 TSDLPANRTQ DLQQHVVTDN LNDNLIFQGY TAWLPTANGL VDVTNHIELT RDGQNLTFTD

1081 DAYLLNLYNQ NKDTAYKLPI IDLVTKANGN TKLIPNNFDS MFVYNDGDQQ TTVNVTSNTV

1141 NISTYDPTAT KDVELGDDIE GDTADTINNL MVQIGTKMTY PLTVSDLPAN RADEITAHQS

1201 VDTLSDYLEY QGYKAYLPDA DGKLQDITEH VNLKREGQKL SFNDDDYLIN LYNNSKATKQ

1261 ALPVIDLVAK VTGSNDGKKV HIIPNHFDST ITTKDGKINT TSNTVVINSN DPEAVKDVEL

1321 GDNVVGDTPN SVTGTTVADG TIVTWPMSVG SLGANRAQNV IKHTETENLD SGLTYLSFKA

1381 YLPDADGKMQ DITEHINIQQ DGQKLVFTDD DYLISLYNKD KSQRFALPVI DLVTRVNGDN

1441 KIIPNTFVSQ FTFNDGKGNT ITSVTSNQVN VSTFKSNPEK HVTLGTDIEG DDAENADGTV

1501 VAQGSEVTWP LSDKSPLPAN RSQDVKSHTL VDKLDDNLQY NSYKAYLKGT DGKLQDVTDH

1561 IKLTRDGQNL TFIDDDYLLD LYNKDKSTAF NLPIIDLVTT VVGNDKLIPN KFDSNFVFSD

1621 GNKDTSMKTT SNEVSISTYT PVTNKDAELG DNVVGDTSDS IANETVPDGT IVTWPLSVSS

1681 LPANRSQDVF KHVIEDILDG NLTYNSFKAY LKDAAGNLQE VTDHVKLAQE GQHLTFTDDD

1741 YLINLYNSSK NKEQSLPIID LVTTVHGDSK LIPNEFDNVF VFKDGKGQTT VKTTSNKVTI

1801 KTASLPTPTK EETDDQGNNI NGNEVKAGEH VNYTLNWDLS NDKDVKATPE MIKKGFFFID

1861 PIDSRALSVD DLSKAKVVDQ NGNKVDGISF HLYNSLSEVP EFIQEQVKAN NLQDKITGPF

1921 VVAQADDLQA FFDKYVKTGA KLKVTIPTIV KSGFTGEFSN TAYQFGFGKA TPTNTVTNYV

1981 KPMHKPASPE TPAAIAPQVI SATAQPMTSD APVTPSEKTA KLPQTGNADE GALLGLAAVS

2041 LVGSLGLAAL GLKQNRNDD
```

Xylulose-5-phosphate phosphoketolase promoter (natural)
SEQ ID NO: 9
```
  1 TTAAAGTATT AAAATAGATG TAAAATTTAT TTTTTTCAAA AGAAATTTTA ATTGTACACT

61 GTTGGTATTG AACGGGGTTA AACAAAGGTA AATTAGCATT TCTGCGGATT AAGATAAATA

121 GAAAAATGTT AAAGAACACC TTAAAAAGAT TAATTTTTTA TAATTGGACC GTATCAATTT

181 GTAAAAAGGT TGACTTTTTG AAAAAAAAGT TTATCATTAA CATTGTAAAT TTAATGATTT

241 ACGTTATGTT GTTATAGAGC ACAGGACGTA TTGATTTATA TAGAAGGAGT GTTTATTAGA
```

Elongation factor TU promoter (natural)
SEQ ID NO: 10
```
  1 ATGAATGGAC AGATGTTTTA ATCGCTAGAA TAGAAGGAAA GAAAGTCGCA ACAAATACGG

61 TTTCTAGTAC GTGGCAGGAA CGACTAGGTA AGCAGATTGA CGAATTAATA GAAAAACATT

121 AGTCAAATAC ATTTACAAAT GAACAGATAG TTGATATTAT ATTTAAGAAT CTTCTTCAG

181 AGCCTAAGAT TAAAGCTTTC AATTGGCGAA AGAAGTTGT ACAATATGTA TAAAGGTATG

241 TCAGTCACCG AATCAGATGA TCTGGCATTA TACTTGTAAA TTATCAGGAG GTTTTCATTA
```

Glyceraldehyde-3-phosphate dehydrogenase promoter (natural)
SEQ ID NO: 11
```
  1 ATCTCACGTG CGATCCATTA CACTAAGGGC GCGTCAACAA ATATTATACT ATCTTAAATA

61 AGAATGAATT GCAAGCATTA TTTGAAAATT TTAATTAAAA TAACGCTTAC ATCAGAAAAA

121 TGTTGTGATT GAATAGACAA TTTTTTTGAA GATGGTATCA TAAGTATCGT AGGAGTTGTA

181 TTATTGCTTA GACCTTACCA CTGCGTCACT TACAATGGTT GAGAGTTGCG ATGCTGATGT

241 AATGTGATAA ACTAAGCAAG TACACTAATT ATGTTTTTTC CTAAAGGAGG AATTTGCAGT
```

Glucose-6-phosphate dehydrogenase promoter (natural)
SEQ ID NO: 12
```
  1 TTGTTTAAGA TATCTTTCAA AGCTGCGGAA TTTTTCCCAG CTTTTTTAGT TAGTTTTGTT

61 TTCATAAGCT ATAATTTTAA CCGATTCCAA ATTTCTTTTA AAAGTTTTTT TGATCTAGAC
```

```
121 CATTAATTGA TAAACGCTTA CCAAAGACTA ATCAACAAGC CATTTAGCGG TAGTGGTCCA

181 TTTTAACTTT CTAAGACATC TTCTCAGAAA ACGTTTCCTT TGATAGTGCA GATTGTGCTT

241 TAAGAGTATA TAATTGTCAC GGTATAAGAA TTTTCTGAAA TTTCAGAAGG AGTGAACATT
```

L-lactate dehydrogenase promoter (natural)

SEQ ID NO: 13

```
  1 CTCCTCTATT ATTATTCCTG ATCAATTTTA AATTAATCTC CCTAGATAGG TATATTTTAG

61 CACAGGTCAC CAACGTTCCA AAGTTTAATC TATGTTTAAA CTTTAATTTT CAAAAAAATG

121 CTATACTATG TTCACGATAC TTTAAGGAAA GGTGATTACA ATAGTGAGTC TCTTAATTGC

181 TATTCTTATC TGCTGGTTGC TATGGAAGAT TGGGGGTTTA ACGGTTAAGT TCATTGGTCT

241 AATCCTTCTT ATTCTATTAA TCGGGACATT AATTCATGTT TTACTTTGGC CAGCGATCCT

301 TTTAGCAGTT ATTATCTTAG GAGCAGGTTT ATTCACTAAC TAATTTATCT ATAAAATCTT

361 ATAGTAATTT TTCTGCGGAA TGTTATAATC ATTACTGTGA GAGAAATCTC AAATAATGTA

421 TACATAAGAT GAAAGGGAGA CTGTTTATT
``` tuf promoter (natural)

SEQ ID NO: 14

```
  1 ACAAATACGG TTTCTAGTAC GTGGCAGGAA CGACTAGGTA AGCAGATTGA CGAATTAATA

61 GAAAAACATT AGTCAAATAC ATTTACAAAT GAACAGATAG TTGATATTAT ATTTAAGAAT

121 TCTTCTTCAG AGCCTAAGAT TAAAGCTTTC AATTGGCGAA AAGAAGTTGT ACAATATGTA

181 TAAAGGTATG TCAGTCACCG AATCAGATGA TCTGGCATTA TACTTGTAAA TTATCAGGAG

241 GTTTTCATTA
```

C protein alpha-antigen precursor (natural)

SEQ ID NO: 15

```
   1 MVSKNNHQFY QQKHAERKQR WGIRKLSVGV ASVLLGTTFM LYGNHAVLAD TVTSPSDDVT

61 RSTTTQGGNK DKVTEGTTEG TTSTPQTSGD STDKQANGQN VNQQVPTTDT EEATNHQDTP

121 QGQDTTQNTT NVDKKDTEVT PANDATTPTT QKITAKFTTA KFTTAKFTAA KFKVLAARPV

181 MKVAGTASLP ISNQDIKLDS QPMLTEIINK PTDNWVYNNL KWYQDTSTEK IKEILQNHTA

241 NDESGRYYFA GVANYNEHYH AIYLLARSNN LNDNSLYVTI LHTGLGKNIQ EAVVAPGESK

301 KVEYSGTTHT PIFTNYDGTS ASIDLDGIEK GDNIYGMVVG FAYGHNTGIK GDPASMGNGF

361 VMTPIPTKMT TTIHYIDQAT GDEIAVPKSF EGVAYQKYTI TGEAPTIDGY TLKKSPETTG

421 YISPYKVGES YDFRLDKHVV IKQTVIDAQG LVRVTAYYDG EVLNNTTRYL GNKLNVNDRM

481 SFISHGKWYT YINQITSTND GIVYYYAKDG SEDKSEVRVH YIDVTGSKNS IFVPGDGEEV

541 ATDKISGKLG ENYNYDVNLP TDYNLATNQA NTVNGTYTID HHDEYVYVVK KTSAELDPTV

601 PAKTKVDNPT SLTADEKKTI EDKIVEANKD KFPEGTGVTV ANDGKATITY PDKSVDTIEG

661 NQLVEEKTSA EKLDPTVPAK TKVDNPTSLT ADEKKTIEDK IVEANKDKFP EGTGVTVAND

721 GKATITYPDK SVDTIEGNQL VEEKTSAEKL DPTVPAKTKV DNPTSLTADE KKTIEDKIVE

781 ANKDKFPEGT GVTVANDGKA TITYPDKSVD TIEGNQLVEE KTSAEKLDPT VPAKTKVDNP

841 TSLTADEKKT IEDKIVEANK DKFPEGTGVT VANDGKATIT YPDKSVDTIE GNQLVEEKTS

901 AEKLDPTVPA KTKVDNPTSL TADEKKTIED KIVEANKDKF PEGTGVTVAN DGKATITYPD

961 KSVDTIEGNQ LVEEKTSAEK LDPTVPAKTK VDNPTSLTAD EKKTIEDKIV EANKDKFPEG

1021 TGVTVANDGK ATITYPDKSV DTIEGNQLVE EKTSAEKLDP TVPAKTKVDN PTSLTADEKK

1081 TIEDKIVEAN KDKFPEGTGV TVANDGKATI TYPDKSVDTI EGNQLVEEKT SAEKLDPTVP

1141 AKTKVDNPTS LTADEKKTIE DKIVEANKDK FPEGTGVTVA NDGKATITYP DKSVDTIEGN

1201 QLVEEKTSAE KLDPTVPAKT KVDNPTSLTA DEKKTIEDKI VEANKDKFPE GTGVTVANDG

1261 KATITYPDKS VDTIEGNQLV EEKTSAEKLD PTVPAKTKVD NPTSLTADEK KTIEDKIVEA
```

```
-continued

1321  NKDKFPEGTG VTVANDGKAT ITYPDKSVDT IEGNQLVEEK TSAEKLDPTV PAKTKVDNPT

1381  SLTADEKKTI EDKIVEANKD KFPEGTGVTV ANDGKATITY PDKSVDTIEG NQLVEEKTSA

1441  EKLDPTVPAK TKVDNPTSLT ADEKKTIEDK IVEANKDKFP EGTGVTVAND GKATITYPDK

1501  SVDTIEGNQL VEEKTSAEKL DPTVPAKTKV DNPTSLTADE KKTIEDKIVE ANKDKFPEGT

1561  GVTVANDGKA TITYPDKSVD TIEGNQLVEE KTSAEKLDPT VPAKTKVDNP TSLTADEKKT

1621  IEDKIVEANK DKFPEGTGVT VANDGKATIT YPDKSVDTIE GNQLVEEKTS AEKLDPTVPA

1681  KTKVDNPTSL TADEKKTIED KIVEANKDKF PEGTGVTVAN DGKATITYPD KSVDTIEGNQ

1741  LVEEKTSAEK LDPTVPAKTK VDNPTSLTAD EKKTIEDKIV EANKDKFPEG TGVTVANDGK

1801  ATITYPDKSV DTIEGNQLVE EKTSAEKLDP TVPAKTKVDN PTSLTADEKK TIEDKIVEAN

1861  KDKFPEGTGV TVANDGKATI TYPDKSVDTI EGNQLVEEKT SAEKLDPTVP AKTKVDNPTS

1921  LTADEKKTIE DKIVEANKDK FPEGTGVTVA NDGKATITYP DKSVDTIEGN QLVEEKTSAE

1981  KLDPTVPAKT KVDNPTSLTA DEKKTIEDKI VEANKDKFPE GTGVTVANDG KATITYPDKS

2041  VDTIEGNQLV EEKTSAEKLD PTVPAKTKVD NPTSLTADEK KTIEDKIVEA NKDKFPEGTG

2101  VTVANDGKAT ITYPDKSVDT IEGNQLVEEK TSAEKLDPTV PAKTKVDNPT SLTADEKKTI

2161  EDKIVEANKD KFPEGTGVTV ANDGKATITY PDKSVDTIEG NQLVEEKTSA EKLDPTVPAK

2221  TKVDDPTKLT NDEKKEVEDN IRDHNTGLPE GTKIAVGDNG DTTITYPDKS VDTIEGNQLV

2281  EEKTSAEKLD PTVPAKTKVD DPTKLTNDEK KEVEDNIRDH NTGLPEGTKI AVGDNGDTTI

2341  TYPDNSVDTI PGDKVVEGKS DAAKNEPKVP GDKVKVDDPN KLTEDEKSEV VKAVEDANKD

2401  ENGKSTLPEG SKVTVGDNGD VTVTYPDGSK DTIPGDKVVE GKGTEGQTDA DKNEPKVPGD

2461  KVKVDDPNKL TEDEKSEVVK AVEDANKDEN GKSTLPEGSK VTVGDNGDVT VTYPDGSKDT

2521  IPGDKVVEGK GTEGQTDADK NEPKVPGDKV KVDDPNKLTE DEKSEVVKAV EDANKDENGK

2581  STLPEGSKVT VGDNGDVTVT YPDGSKDTIP GDKVVEGRGT EGQTDADKNE PKVPGDKVKV

2641  DDPTKLTEDE KSDVEQAIKD ANKDENGKST LPEGSKVTVG DNDDVTVTYP DGSKDTIPGD

2701  KVVEGKGTEG QTDADKNEPK VPGDKVKVDD PNKLMEDEKS DVEQAIKDAN KDENGKSTLP

2761  EGSKVTVSDN GDVTITYPDG SKDTIPGDQV IEGKSDADKN TPNVPGGDKV KVDDPTKLTD

2821  NEKNAVKDKV DEANSNLPDG TKVTVGDDGT TTITYPDGST NTISGHDLVT GKTDADKYPL

2881  NPGQAVNVVD PNHLTQAEQD QVKEAIQTTN PTAPIATITV DTAGNVQVTF ADGSTTTLQA

2941  NLHKHVTEAT TGSAIKPGVG TNGGQTKGAT STNQTATKQQ AQQHLPQTGD QPATWAMLSG

3001  LGVAFLGLLG LKKKRED

Arabinogalactan endo-1,4-beta-galactosidase (natural)
                                                                         SEQ ID NO: 16
   1  MEIKKHFKLY KDGKKWCCAA IATTVLGIGL AIGSPSVLAD ADTITSTSDA NNSLVKNDNT

61  SDTDSNSEST FTDTNKNSTN EKEINENKNI DSSQQINQEQ TKSNNSEEQT TPVNVKAENT

121  DIKDSIPEKS TPNSFKEING STYYYGENGD LYRNQFYNNW GRTYYFQANG ARLDNGFYNN

181  WGRTYYFGSD GARWDNRFYN NWGRTYYFQN DGSRLDNSFY NNWGRTYYFG VDGARWDNRY

241  MVKWGRAYYF GNDGALLQNQ LKSINGINYW INNEGIIPLK NQFLTANENQ LFYFDGNGSL

301  VVNKFYHNWG HTYYFGSDGA RYTDQFLNRD GKVYYFDNQG IMYQDQYYKN WGHTYYFGSD

361  GARYTDQFLN RDGKVYYFDN QGIMYQDQYY KNWGHTYYFG SDGARYTDQF LNRDGKVYYF

421  DNQGIMYQDQ YYKNWGHTYY FGSDGARYTD QFLNRDGKVY YFDNQGIMVT NQVRVIDGKG

481  YEFNDNGEAT ETSDMGQTRD TVAKEVAQAL TNQGIKGVKY DWRNTNNDYQ ELALHDIAQE

541  VAQGDTNPDK NVIEKKLQAN NLLSGKVLVV YSTDFTNDDP QKITNTFMNS YDFTNADNSV
```

```
601  LGVGADLNKN KLVIILFKPG EKAEQPQATS TISASISDIF KKAGVNVDVD NGLTKGSVVN

661  SADLGNALTN GTAELLKGDK GTIISQEVLK AIFAAFAGNT SAVEGTKNYY NGNDAYHYEF

721  WLEGQSADDK LNNFLALNKG AKYGDQLKVN YTATLVFGQE TGTNSNESKV PASERTDEQL

781  DLAYKTGTDT GLRYDSVKVE KIPGMTDDMV RGVDVSSYQA LINAGVKFYD FNGQESNLFK

841  ILKDSGVNWV RLRVWNDPYN AQGQPYAGGD NNEENLIKMA KEASDNGLKL LIDFQYSDFW

901  TDPAQQILPK AWRNLSHGEM SQEVYLYTSK ILNDLQKAGA SVKMVQIGNE ITNGAFGLYT

961  GRNGGGNWAS LWETSDGDQV AKYIQAGSSA VRRIDPTIKV AIQLETPEIN KYRGIMNVLK

1021 KNNVDYDYLG TSYYPFWSTT QGNGWYDNVD LGYGANTPVN LEAIEKMAWN EFGKRTVILE

1081 SGWLNNTNDA DGTHNSVGEN NETTNIDRYS ADPQGQVDEI EDMYNAIIAQ KGLGAFYWEP

1141 AWIPVKAGWN NWQYNKLMSN IYGSGWASQY AKGYAPDSVL YYDGKEAWGG SSWDNISLFD

1201 DHGHPLQSLN VYNGMLNGYE SPKNVKSSLS TQLVKIWNET DVIPNDGLTE GTKLSTDLFG

1261 TTQLSGNDGQ SIGNAELTKL AGRLKDGISS KVYTAANGAR YHYIYWLEGG NNKVNTFVSA

1321 NKDAKYGQPL IANYSATVVV DSEPGTQVAT SPLQIKISQV WNTVNNEEIK IDNPLKQGDL

1381 ITDKSDNAFS GILNSKDIKE ALTGEKGKDV SESTVNDVKS LLPKEVKGSK TYTTADGNQY

1441 YYDFWLASVE TSNVNYGEPI IVNYTASLKW LG

Chromosome segregation protein (natural)
                                                    SEQ ID NO: 17
   1 MEKTMKKKAL VATTAVAGIT LVGEVTTVHA ADNVQQPVNE QNVNQSSQEE KQAAQNLQNA

61 QSDVNTATEA NSNAQDNLAS ANNNLSNAKK AVSDQAAKVA DATKAQSDAS TKVDNDNKVV

121 ADAQQKADQA TPANIENAKQ AIEGQNKVID QDNENIKYSN TDQDKAQNTL NNAQSNEDKA

181 NATLSNKKSS QASAQNNVKQ AEDALNGTHL VEAQNAFNQA QSNVENAQSK YDQANNQLSD

241 AQKKVTTNQN DLTAKNKALD NINNQVDTDQ NNVNSNQATA DSASSATQVA QNAVDQTKQS

301 LDKVIEELNG FSENTIKVPA GAQEAYEAFI DAVDNNADQS QLDSLAKKMY DTLHQGQGTN

361 GINHFNSSKY DQNQLVDVDH LTTDQLNELT QFAADMINSA RKAWGSDKNA GTLIPTQGVS

421 EMAQQIAKGY VSDNWHISQG HDVKRVTAAA GLIGLNDAGQ FYEDASEGYV HAWPWEKDSY

481 TMDNLKEAVY DSILGMLFAD DNSGNGHMTD LLGLHVNRKE DHQYFGLSTN MCPGSYMGQL

541 HFIIVENDPA YIKDPQTFNA KGGTTKIEYI DPKVQLNQQK DILTTTLSTQ QADLATKQDA

601 LNKANQNLAN AKKQLSEDQD LQTVAQQNRD SAQKALNDAT AKVSNLQATV NSLSQDLNSA

661 KATLDQAKKT LESYTADHKA KLDNYNNAKA ALDDANKAVA EAQSAVDTAV NETKIAQNNL

721 DQKKQAVTDA QNKLANDQEY LATLKQNLAD LQNAPQNLQK AKDQLAKDQI ALDNANKDLQ

781 NQKDSLDELN KKLEDAQVKV NEAQSAANVT KATLDQAQAK LSDAEATWKE LHNDAHRYGN

841 VVKVTPITME AGTSLPDPVI ENGFTVNTGT NQLFVSLAAI DSSNNNIPQG TKASWANRSK

901 ALTDSQNAGS YSEDILITFP DNSTVTPVD LTVTAKKITE DQKATEGGYH IVNGSVVDKQ

961 NNLVSGWTVK NGQMVDPEGN VIKTTMSTAQ GVTIEKNNSK SGNTKTNMIQ TSLTIANNKA

1021 TTNKDNQLPQ TGNYNNNTKV LGLAGIALAS ALTMFGYKKR QHN

D-gamma-glutamyl-meso-diaminopimelic acid endopeptidase Cwls (natural)
                                                    SEQ ID NO: 18
   1 MKSTTKKILA SSLGVAGAMA MGTVTAKADT TVTVNAGDSL NGIAQKYNVS ADDIATANHL

61 QNKELIFVGQ KLTIPTKDKN ETPANNAEKK DQASKNSQSL QDSVNKAMSY LGTPYVWGGN

121 KPGGFDCSGL VQYCYGIPQR TTYEQQALGP HIHDNVLNAP YGALVFYGSD DAPYHVAISL

181 GDGRIIQAPN ENETVKITDQ QYFPGNYYVV MH
```

-continued

N-acetylmuramoyl-L-alanine amidase sle1 precursor (natural)
SEQ ID NO: 19

```
   1 ATGCGTAATC AATTCATCGA TGTTTCAAGT TATCAACCAG ATACGTTGC CTTTTTCCAA
  61 GCTGCTAAAG CTCAGGGTGC ATTAGGGGTC GTTGTTAAGT TAACGGAAGG GTCCGAAGAT
 121 GGTTCGGCTT ATGTTAATCC ACGTGCGGCC GCTCAAATTC GTAATGCCTT AGCGGTTGGC
 181 TTGCGCGTTT CCTGTTACCA CTTTGCTCGT TATACATCAG TGACTGATGC ACAAAATGAA
 241 GCTCGATTCT TCGTTAAAAT CGCTAAGCAA TTTGGTATGT ATGACGATAC TTTGATGATT
 301 GATGATGCGG AAGTTCATTC AACTGCAGAT TATCAATCAG TATCCTTAGC CTTTCTTCAA
 361 GAAGTAGAAG CTCTTGGTTA CAAGAATACT GGGATTTACT CCATGAAGTC CTTCTTCACT
 421 GGCGGTATTC TTAATTCACA TGGCTTTGAT TCCCGGAAGA TTTGGATTGC TGGCTATGGT
 481 GTGACTGAAC TGGGGATTGA TAATGCAAGT GCTTGGCAAT ATTCTGATCA TAGCATCATG
 541 GGAATTGATA CTAGTTATGA CTTTGACGGT GCCTTTACGA CTGGTTTAGT ATCAGGCAAT
 601 GTTCCGCAAG CTGTTATTCC AGCACCACAG CCGGTTCAAC ATATTGGTCA CCCAGCTACT
 661 GGAACCTACA TTGTTCAGCC GGGCGATACA TTGAGTGGAA TTGCAGAAAA ATACGGGACT
 721 ACTTATCAGA ACCTAGCAGC AATCAATGGT ATTGGTAATC CAAACCAGAT CAATGTCGGC
 781 CAAGTCCTCA AAGTCACCGG AAAAGTATCA AACGAAAATA CTTACTTTGT TCAATCAGGC
 841 GATACGTTAT CCGGAATTGC CACCAAATTC GGCACCACTG TCTCAGACCT CGTAAGCCGT
 901 AATCACATTA CTAACCCGAA TGTGATCTAC GTTGGGCAAA ACTCTACTT AGCCGGCAAC
 961 GGACAATCCA ATGCTTATAC TGTCCAAGCA GGGGACACAC TAAGCGGAAT TGCGGCTAAG
1021 TTTGGCAAGA CCTGGCAAGC ATTAGCTCAA AAGAATGGCA TCGCAAATCC TAATATGATT
1081 TTCATTGGTC AAACAATTCA GATTTAA
```

Peptidase family M23 (natural)
SEQ ID NO: 20

```
   1 GTGTACCGAA TTATTGGTTA TAATGAACCA ACAGATAAAG CAGGATTTAT TGTACTGGAT
  61 CCCCGAGTTA ATCGTCATAT TAGTTCGGGA AAACTCACGC TTAAAGAATC TAATATTGAT
 121 GATTTGACTA TTACGGTTAA TCAAGCAAGT CCATTATGGG ACAACGTAAG GCCTTATCAT
 181 ACTCATGTTA ACGTTTATGA TGATAATGAA CTTATTTTTC GTGGACGAGC TATCAAACCT
 241 AAAAAGTCGA TGGAAGAAAG CGGACAATTC ATTCGTGAAT ATGTTTTTGA AGATATTGAA
 301 GCATATCTCA TGGATAGCAC CCAAAGATTT TATGAAGGTG TTGGTCAAAC GCCCAAAGAA
 361 TTTTTACAAA CTTTAATCGA TGTTCATAAT TCACAGGTTC CTGACTATAA AAAGTTTCAA
 421 GTCCGGAATG TAAATGTCAC TAATAATAAG GATGACCAAT ATCGACAAAT TGATTATCCC
 481 AAAACTAGCG ATGCTATTAA TGATAAATTA GTTAAATCTC TTGGTGGTTA TATTGTGACT
 541 ACTTACAACG CTAACGGAAT AAACTACATT GACTACTTAA CGGATATTGG GGTTGATCAT
 601 AAAGATGATA CTCCTATTCA GTTAGCTAAA AATATGAAGT CTGCAAGTAT GCAAATTGAT
 661 CCTACTAAGG TGATTACAAG ACTGATTCCA CTGGGAAAGA CACTAGAACC ATCAAAAGTT
 721 GATGTAAGTG ATGATGATGG AGAGGGCGGT TCTGGATCAT TAGATAGCCC TGAAGAATTT
 781 TGTAAATCAG AAATTAATGC TACTTGGGGT AGTGATATTA ATAATATGAA ACAAGATTTT
 841 GCCGCTCGTT CTTCGAGAGT TCGGGCTTGG GGAGTGGACG TTAATCGTTT ATATGATGTG
 901 GTGAAAAATG CTGGAGTAAG TCCTGAATGG TTCTTTGCTT ATGAACTTCA AGAACAAGGA
 961 ACTTACTATG GATGGCTTAA CCATACTTAT CGACACGGTG ATGCGTATAG TGATGCGCAA
1021 TCTGTTTGTG AGTGGATTAA AAATTGTTCA AATAGTAATT CCATTAATCC AGCATGGAGC
1081 GCACCGGAAG GATCAATGGC GCCGAATCAA GCATTAGCGG ATAAATGAA TCAAGAGTTT
1141 GGAAAAGGTA CTATTGGCCG CGTTTATTTA CAAGGGACTG CCGCTGCTGT TTGGGATTTA
```

-continued

```
1201 GCTGGTCAAA CGCCTAATCC AGCTATTGGA AAGCCAATTA GTGGATGCAT TTCTTGTATT

1261 AAACGTTGGG GTGGTCATTC TAATGCAGCT GGTGGTACAT GGGGATGGCC TTTTCCTGAT

1321 GTTGGGGAAG GTCATTTTTC TCAAGTTCAG AGTTTCGGAA ATGATGGCGG ATATCGTCAA

1381 AATAGTTATC ACGATGGTGT GGATTTTGGA TCAATAGATC ATCCTGGTAG AGAAGTGCAT

1441 TGTATTCATG GTGGAACGGT AACTATCAAA TCAGCTATGG GTGGCTTAGG TAATTTTGTG

1501 GTTATTCATA CGCCGGAAGG ATTCAATATC GTTTATCAAG AAGCTTTTAG TTCTCCCTCT

1561 AATATTATTG TTAGTGTTGG GCAAAAAGTA AAAACTGGTG ATGTAATTGG ATATCGTGAT

1621 ACAGACCATG TTCATATTGG CGTAACTAAG CAAGATTTTT ATCAAGCAGT TCGAAATTCT

1681 TTTTCTCCTG CAGGTGGTTG GCTAGATCCA GTAAAACTAA TTAAAGAAGG TGGCGATGGG

1741 TCTAAACCAC AAGAAGGAAA GAAAGATCAA ACTGTTGATA ATAGTAATGC TGCACGTCCT

1801 AAATTAACCA TTACTACTGT CAATAACGGT AGAGACTATA TTGATATTCC TGATTTACAA

1861 AAAGAATTCG GTATTATTGA GGGAACTGTT GAATTGATA ATGTAGATGA TCCGAATGTT

1921 TTAATGCAAC AAGCTCAAAC ATGGATAAAG GCTCAAAGAA TACCTCAAAG TTGGGAAGTT

1981 ACAGCTTTAG AATTACATAT GACAAACTTC AAATCTTTTA AGGTTGCTGA TAGGTACATG

2041 TTTATTAATC AAATGTTGC AAAACCCCAA TTATTACGAA TTACTCAAAA AGAAATTGAT

2101 TTACTAAAGC CCCATGCGTC TTCATTAACG ATTGGTGATA AGACGATGGG GCTTACTGAT

2161 TATCAGTTAG AAAATCAAGT CAATTTTCAA CAATTTAAGG AAATTCGAGT GATGGTTAAT

2221 CAGGTTGTCC AAACCCAAGA GCAATCTGCT AATAACAATA TAAGGTTAT GCAAAATTTT

2281 GCTAGTAGTG CTGATCTTGC ACAAATGAGA CAGGATCTAA GAAATCTTCA AGATGATAAC

2341 GATCGTGCTC GCAAAGGAAT GGTTTCCTTA GAAGAATTCA ATAAACTAAA GGAACAAGTA

2401 GAAAAACTAA CAACAGGAGG CGATGATAAT GGCAAGTGA
```

Chromosome Partition Protein Smc (natural)
SEQ ID NO: 21
```
  1 MNKANQKVAD DTTAYNNKQT DVNNAAEEAKK NADEALKNAN DAQTSAQKNK DAKQAIADEA

61 SVALADANTA VKDAQAKVDA INDKLANFNT ITLPAGYKDD LIAYYNYFGN SNYNQDEANN

121 LAQDLLKYRD QAMSQNKFKD NLSDDRVVDI DNLNSTDRAE LSQFVASLIN QVRTQMGTNL

181 VISSPAADDY AEQVSQNYNK DNWNSADNGK HDQSALNNAT DQLNISWNGE NMGLDQSIFT

241 TDYTVLTDGT KLPTGNKQTI NDLKHLIYDD FISMMFDDAD SAWGHATNFA GIDNFAAEKQ

301 AVGFSLDKFY NTHYDLVEAN QKVEENSYTL PSINALTQKL ADAKDDLSIK QTDQASKQKA

361 NDDAQNALSS ANQVLVAAQN DVKDKTATAQ EANDNLTTAQ NDLATLQNQL SADQANQKQA

421 QTTFDSFDAD LATKQANLQK ATDSLKAEQG RLAIAQADLD NANKALSDAN NNLAQKKQVV

481 ENDNETLKVD NDKLVQLQNN LSDLQNAPKL LAAAKEQVAT AQKALADAQE AYNVANDKLT

541 SLKQTAAGTT TNVSKAQQAL AEAKNNEDAA KEVLDQAQQA LTELRQKEAL AKQVAEEQAK

601 LAAEKEAKDN GYHIENNQVV DAKGNSVNGW TVKGNQIVSP TNATVDPAVS VTTNVNVDSK

661 GQVQPQTSVT ANSVKTVAAT ESANPVATTT VQTREQYKQQ LKSNNQLPQT GNNDSAVLSL

721 AGVALAAMLS LFGIKKREY
```

Cwls endopeptidase promoter (natural)
SEQ ID NO: 22
```
  1 AAATTAAAAG GCTGGATTTT TTCGGCCTTT TTTTAGTGCA AATAATTATT TTTTACGTAT

61 TTATATTATA GGGCTAATCA CTAAACTAAT AATTAGTGGT TGAAGCGCTG AAAATTTTCT

121 GCTATTTTAT TAATAGTTTG ATAATAAAAT AATGATATTT AATATAAAGA GGGATAAACG

181 AAATA
```

-continued chromosome segregation protein promoter (natural)

SEQ ID NO: 23

```
  1 GAAGTACAAA GTTACTTTAA CTATAATGAA AAACAAGACA ATATAAAGAA AACAACATAT
 61 AAGGTTCAGT TCATAACTGA TTAGATTTAT AATAAATATT GTAAATCGGA CAAAAATAAA
121 TTAATTTTCA ATTAATTCAA AAAAACCATA TTTTTTTCGT TTTGGCATAT TTGGATTTGC
181 TACACTAAAG ATGATCAAGA AAGGGGAAAA GATAATCTTC AATCTTGTGT ACTTAGTTTG
241 TTAATTAATT TATAAATTTA GGGAGGAAAC CTATC
```

Chromosome Partition Protein Smc promoter (natural)

SEQ ID NO: 24

```
  1 GCAATGCACA AGATGCTGAA ACAAAGGCAC AACAAAATGC AGATCAAGCT TCACCAGCTA
 61 ATATTCAAAA GGCACAAGAT GCTATTGCTA ATCAAGAAAC TCAAATTAGT AAAGACACCG
121 ATGCTATTAA TGACGCTAAC AAAGCCGTTA GCGATGCACA AGCACAGTT GATGCAGCGC
181 AAAAAAGTT AATGATGCAA CTACTGCTCG TGACAATCAA CAAAAGAATG TTGATACTGC
241 TAGTGATGCA GTTAAGAATG CTCAAGCTAT TCTTGACAAC AGTGATCAGG CTAAAAAGGA
301 AGCCCAAGAT GCT
```

*Lactobacillus reuteri* 3630 F1 16S

SEQ ID NO: 25

```
  1 GCCGCGGGTG CCTATACATG CAGTCGTACG CACTGGCCCA ACTGATTGAT GGTGCTTGCA
 61 CCTGATTGAC GATGGATCAC CAGTGAGTGG CGGACGGGTG AGTAACACGT AGGTAACCTG
121 CCCCGGAGCG GGGGATAACA TTTGGAAACA GATGCTAATA CCGCATAACA ACAAAAGCCA
181 CATGGCTTTT GTTTGAAAGA TGGCTTTGGC TATCACTCTG GGATGGACCT GCGGTGCATT
241 AGCTAGTTGG TAAGGTAACG GCTTACCAAG GCGATGATGC ATAGCCGAGT TGAGAGACTG
301 ATCGGCCACA ATGGAACTGA GACACGGTCC ATACTCCTAC GGGAGGCAGC AGTAGGGAAT
361 CTTCCACAAT GGGCGCAAGC CTGATGGAGC AACACCGCGT GAGTGAAGAA GGGTTTCGGC
421 TCGTAAAGCT CTGTTGTTGG AGAAGAACGT GCGTGAGAGT AACTGTTCAC GCAGTGACGG
481 TATCCAACCA GAAAGTCACG GCTAACTACG CCCCCCACCA GCCCCAA
```

*Lactobacillus reuteri* 3632 F1 16S

SEQ ID NO: 26

```
  1 TGCTGGGGTT TGCCTATACA TGCAGTCGTA CGCACTGGCC CAACTGATTG ATGGTGCTTG
 61 CACCTGATTG ACGATGGATC ACCAGTGAGT GGCGGACGGG TGAGTAACAC GTAGGTAACC
121 TGCCCCGGAG CGGGGGATAA CATTTGGAAA CAGATGCTAA TACCGCATAA CAACAAAAGC
181 CACATGGCTT TGTTTGAAA GATGGCTTTG GCTATCACTC TGGGATGGAC CTGCGGTGCA
241 TTAGCTAGTT GGTAAGGTAA CGGCTTACCA AGGCGATGAT GCATAGCCGA GTTGAGAGAC
301 TGATCGGCCA CAATGGAACT GAGACACGGT CCATACTCCT ACGGGAGGCA GCAGTAGGGA
361 ATCTTCCACA ATGGGCGCAA GCCTGATGGA GCAACACCGC GTGAGTGAAG AAGGGTTTCG
421 GCTCGTAAAG CTCTGTTGTT GGAGAAGAAC GTGCGTGAGA GTAACTGTTC ACGCAGTGAC
481 GGTATCCAAC CAGAAAGTCA CGACTAACTA CGCCCCACAC CCCAGCCGCA A
```

*Lactobacillus reuteri* 3630_00184

SEQ ID NO: 27

```
  1 ATGGATATGA AAATAAAAAA AGAACCACCA CAACAAGTAA AATTAGTTGA AGTAATTCAG
 61 GTTATAACCT CTCGTGGAGC TGGAACAAAG GAGGATCCGA TAAGAAAGAT TATTCAGTAT
121 TGGAGCAAAG AAGGCACATT ATTAGCAGAA AGTTTTGGAA ACTAA
```

*Lactobacillus reuteri* 3630_00491

SEQ ID NO: 28

```
  1 ATGGCTGGTA TCAAAAGTAT CGCAAAAGCG GTAATGACCC AGAATCACTT CGTGATCGCC
 61 GAGGCAAAGC TAAGCCAGAA GAGAAGTGGA CGGAAGTTGA CCGACTCAAG GCAGAAAATC
121 GCTTATTAA
```

*Lactobacillus reuteri* 3630_00497

SEQ ID NO: 29

```
  1 ATGGCTAAAT ACACTGTTGA ATTAAGTGAA GAAGATATCC AAATGATCAA GGATTGTCAT
 61 TCAAAGAATC CTTCTATCAT GAAGGCAATG AACGACGCTA AAAAGTTGA AGATTAA
```

*Lactobacillus reuteri* 3630_00533

SEQ ID NO: 30

```
   1 GTGGATGCGG ATTCGCTGGC ACTCGTTGAT GCACTTTCAC TTGCGCTCGT TGATGCCGAT
  61 TCACTGGCAC TCGTTGATGC ACTTTCGCTA GCACTAGTAG AAGCTGACTC ACTTGCACTT
 121 GTCGATGCCG ATTCGCTTGC ACTTGTCGAT GCTGATTCGC TTGCGCTCGT TGAGGCTGAT
 181 TCGCTAGCAC TAGTAGAAGC TGATTCACTG GCACTCGTTG AGGCACTTTC ACTTGCGCTT
 241 GTTGAAGCCG ACTCACTTGC GCTCGTTGAT GCACTTTCGC TGGCACTTGT CGATGCCGAT
 301 TCACTTACGC TCGTTGAGGC CGATTCGCTG ACACTCGTTG ATGCACTTTC ACTTACGCTC
 361 GTTGAGGCCG ATTCGCTGAC ACTCGTTGAT GCACTTTCAC TTACGCTCGT TGAGGCCGAT
 421 TCGCTGACAC TCGTTGATGC ACTTTCGCTG GCACTTGTCG AGGCACTTTC ACTTACGCTC
 481 GTTGAGGCCG ATTCACTTAC GCTCGTTGAG GCCGATTCAC TTGCGCTTGT GGATGCGGAC
 541 TCACTTGCAC TCGTTGAGGC ACTTTCACTT GCACTTGTCG ATGCAGATTC GCTGGCACTC
 601 GTTGATGCAC TTTCACTTGC ACTCGTTGAT GCACTTTCAC TTGCACTTGT CGATGCGGAT
 661 TCACTTGCAC TTGTTGAAGC GGATTCGCTA GCACTTGTCG ATGCGGATTC ACTTGCGCTT
 721 GTTGAAGCGG ATTCGCTGGC GCTTGTTGAA GCCGACTCAC TTGCACTCGT TGAGGCTGAT
 781 TCACTTGCAC TCGTTGAGGC ACTTTCGCTG GCGCTCGTTG ATGCAGATTC GCTGGCACTC
 841 GTTGAGGCCG ATTCGCTGGC GCTTGTTGAG GCCGATTCGC TTGCACTTGT CGATGCTGAT
 901 TCACTTGCAC TGGTTGAAGC AGATTCGCTG GCACTCGTTG AGGCACTTTC GCTGGCACTC
 961 GTTGAGGCCG ATTCACTTGC GCTTGTTGAA GCTGATTCAC TTGCACTTGT CGATGCTGAT
1021 TCACTTGCGC TAGTAGATGC CGATTCGCTG GCACTCGTTG AAGCAGATTC ACTTGCGCTT
1081 GTTGAAGCCG ATTCACTTGC GCTTGTTGAA GCCGACTCAC TTGCACTCGT TGAGGCACTT
1141 TCGCTGGCGC TCGTTGAAGC AGATTCGCTG GCACTCGTTG AAGCAGATTC GCTGGCGCTT
1201 GTTGAGGCCG ATTCGCTTGC ACTTGTCGAT GCTGATTCAC TTGCACTGGT TGAAGCAGAT
1261 TCGCTGGCAC TCGTTGAGGC ACTTTCGCTG GCACTCGTTG AGGCCGATTC ACTTGCGCTT
1321 GTTGAAGCTG ATTCACTTGC ACTTGTCGAT GCTGATTCAC TTGCGCTAGT AGATGCCGAT
1381 TCGCTGGCAC TAGTAGAAGC AGATTCACTT GCGCTTGTTG AAGCCGATTC ACTTGCGCTT
1441 GTTGAAGCCG ACTCACTTGC ACTCGTTGAT GCCGATTCAC TTGCACTTGT GGATGCGGAC
1501 TCACTTGCAC TCGTTGATGC ACTTTCACTT GCACTTGTGG ATGCGGATTC GCTGGCACTC
1561 GTTGATGCAC TTTCACTTGC GCTCGTTGAT GCCGATTCAC TGGCACTCGT TGATGCACTT
1621 TCGCTAGCAC TAGTAGAAGC TGACTCACTT GCACTTGTCG ATGCCGATTC GCTTGCACTT
1681 GTCGATGCTG ATTCGCTTGC GCTCGTTGAG GCTGATTCGC TAGCACTAGT AGAAGCTGAT
1741 TCACTGGCAC TCGTTGAGGC ACTTTCACTT GCGCTTGTTG AAGCCGACTC ACTTGCGCTC
1801 GTTGATGCCG ATTCACTGGC ACTCGTTGAG GCACTTTCAC TTGCGCTTGT TGAAGCCGAC
1861 TCACTTGCGC TCGTTGATGC ACTTTCGCTG GCACTTGTCG ATGCCGATTC ACTTGCGCTT
1921 GTGGATGCGG ACTCACTTGC ACTCGTTGAA GCCGATTGGC TTGCACTAGT AGAAGCTGAT
1981 TCACTGGCGC TCGTTGAGGC TGATTCGCTG GCGCTCGTTG AGGCTGATTC ACTGGCACTC
2041 GTTGAGGCCG ATTCGCTGGC GCTCGTTGAT GCAGATTCGC TGGCACTAGT AGAAGCTGAT
2101 TCACTGGCGC TCGTTGATGC CGATTCACTT GCACTTGTCG ATGCGGACTC ACTTGCACTC
```

-continued

```
2161 GTTGATGCAC TTTCGCTTGC ACTTGTGGAT GCGGATTCGC TGGCACTCGT TGATGCACTT
2221 TCGCTAGCAC TTGTCGATGC CGATTCACTT GCACTCGTTG ATGCACTTTC GCTAGCACTC
2281 GTTGATGCAC TTTCACTTGC ACTTGTGGAT GCGGATTCGC TGGCACTTGT TGATGCGGAC
2341 TCACTTGCAC TTGTTGAAGC CGATTCACTG GCGCTCGTTG ATGCCGATTC ACTTGCACTT
2401 GTCGATGCCG ATTCACTGGC GCTTGTTGAT GCGGACTCAC TTGCACTCGT TGATGCACTT
2461 TCACTTGCAC TTGTGGATGC GGATTCGCTG GCACTAGTAG AAGCTGACTC ACTTGCACTT
2521 GTCGATGCCG ATTCACTGGC ACTCGTTGAA GCACTTTCAC TTGCGCTTGT TGATGCGGAC
2581 TCACTTGCAC TCGTTGAAGC CGATTCGCTA GCACTTGTCG AAGCTGATTC ACTGGCGCTC
2641 GTTGATGCTG ATTCACTGGC GCTTGTTGAA GCCGACTCAC TTGCGCTCGT TGATGCACTT
2701 TCACTTGCGC TCGTTGATGC CGATTCACTA GCACTAGTAG AAGCTGATTC ACTGGCGCTT
2761 GTTGATGCAG ATTCGCTGGC ACTTGTCGAT GCCGATTCGC TAGCACTAGT AGAAGCTGAT
2821 TCACTGGCGC TTGTTGATGC AGATTCGCTG GCACTTGTCG ATGCCGATTC GCTAGCACTA
2881 GTAGAAGCTG ATTCACTTGC ACTTGTCGAT GCCGATTCAC TGGCGCTCGT TGATGCCGAT
2941 TCGCTGGCAC TAGTAGAAGC TGACTCACTT GCACTTGTCG ATGCCGATTC ACTGGCACTC
3001 GTTGATGCAC TTTCGCTAGC ACTTGTAGAT GCGGATTCAC TTGCACTCGT TGATGCACTT
3061 TCACTGGCAC TCGTTGATGC ACTTTCGCTA GCACTCGTTG AAGCACTTTC ACTTGCGCTT
3121 GTTGATGCGG ATTCGCTGGC ACTCGTTGAT GCACTTTCAC TTGCGCTCGT TGATGCCGAT
3181 TCACTTGCGC TTGTGGATGC GGACTCACTT GCACTCGTTG ATGCACTTTC GCTTGCACTT
3241 GTGGATGCGG ATTCGCTGGC ACTAGTAGAA GCAGATTCAC TTGCGCTCGT TGATGCCGAT
3301 TCACTTGCGC TTGTGGATGC GGACTCACTT GCACTCGTTG ATGCACTTTC ACTTGCACTT
3361 GTGGATGCGG ATTCGCTGGC ACTAGTAGAA GCTGACTCAC TTGCACTCGT TGAAGCACTT
3421 TCACTTGCGC TTGTGGATGC GGACTCACTT GCACTTGTCG ATGCTGATTC GCTAGCACTA
3481 GTAGAAGCTG ATTCACTTGC ACTCGTTGAT GCACTTTCAC TTGCGCTTGT TGAAGCCGAC
3541 TCACTTGCGC TCGTTGATGC CGATTCACTT GCACTCGTTG AGGCACTTTC ACTTGCGCTT
3601 GTTGAAGCCG ACTCACTTGC GCTCGTTGAT GCACTTTCGC TGGCACTTGT CGATGCCGAT
3661 TCGCTGGCAC TAGTAGATGC GGACTCACTT GCGCTCGTTG AAGCCGATTG GCTTGCACTA
3721 GTAGAAGCTG ATTCACTGGC GCTCGTTGAG GCTGATTCAC TGGTACTCGT TGATGCACTT
3781 TCGCTAGCAC TCGTTGAAGC ACTTTCACTT GCGCTTGTGG ATGCGGACTC ACTTGCACTA
3841 GTAGAAGCAG ATTCACTTGC GCTCGTTGAT GCCGATTCAC TTGCACTTGT CGATGCCGAT
3901 TCACTTGCGC TTGTGGATGC GGACTCACTT GCACTCGTTG ATGCACTTTC GCTTGCACTT
3961 GTGGATGCGG ATTCGCTGGC ACTAGTAGAA GCAGATTCAC TGGCGCTCGT TGATGCCGAT
4021 TCACTTGCAC TTGTCGATGC CGATTCACTT GCACTCGTTG ATGCACTTTC ACTGGCACTC
4081 GTTGATGCAC TTTCGCTAGC ACTCGTTGAA GCACTTTCAC TTGCGCTTGT TGATGCGGAC
4141 TCACTTGCAC TTGTTGAAGC CGATTCACTG GCGCTCGTTG ATGCACTTTC ACTTGTGCTT
4201 GTTGAAGCCG ACTCACTTGC GCTCGTTGAT GCACTTTCAC TTGCGCTCGT TGATGCCGAT
4261 TCACTAGCAC TAGTAGAAGC TGATTCACTG GCGCTTGTTG ATGCCGATTC GCTGGCACTT
4321 GTCGATGCCG ATTCGCTAGC ACTAGTAGAA GCTGATTCAC TGGCACTTGT CGATGCCGAT
4381 TCACTGGCGC TCGTTGATGC CGATTCGCTG GCACTAGTAG AAGCTGACTC ACTTGCACTT
4441 GTCGATGCCG ATTCACTGGC ACTCGTTGAT GCACTTTCGC TAGCACTCGT TGATGCACTT
4501 TCGCTAGCAC TCGTTGATGC ACTTTCACTT GCGCTCGTTG ATGCAGATTC GCTAGCACTA
4561 GTAGAAGCTG ACTCACTTGC ACTTGTCGAT GCCGATTCAC TGGCACTCGT TGATGCACTT
```

```
4621 TCGCTAGCAC TCGTTGATGC ACTTTCACTT GCGCTTGTTG AAGCCGACTC ACTTGCGCTC

4681 GTTGATGCAG ATTCGCTAGC ACTAGTAGAA GCAGATTCAC TTGCGCTCGT TGATGCCGAT

4741 TCACTTGCGC TTGTGGATGC GGACTCACTT GCACTCGTTG ATGCACTTTC ACTTGCACTT

4801 GTGGATGCGG ATTCGCTGGC ACTAGTAGAA GCTGACTCAC TTGCACTCGT TGAAGCACTT

4861 TCACTTGCGC TTGTGGATGC GGACTCACTT GCACTTGTCG ATGCTGATTC GCTAGCACTA

4921 GTAGAAGCTG ATTCACTTGC ACTCGTTGAT GCACTTTCAC TTGCGCTTGT TGAAGCCGAC

4981 TCACTTGCGC TCGTTGATGC CGATTCACTT GCACTCGTTG AGGCACTTTC ACTTGCGCTT

5041 GTTGAAGCCG ACTCACTTGC GCTCGTTGAT GCACTTTCGC TGGCACTTGT CGATGCCGAT

5101 TCGCTGGCAC TAGTAGATGC GGACTCACTT GCGCTCGTTG AAGCCGATTG GCTTGCACTA

5161 GTAGAAGCTG ATTCACTGGC GCTCGTTGAG GCTGATTCAC TGGTACTCGT TGATGCACTT

5221 TCGCTAGCAC TCGTTGAAGC ACTTTCACTT GCGCTTGTGG ATGCGGACTC ACTTGCACTA

5281 GTAGAAGCAG ATTCACTTGC GCTCGTTGAT GCCGATTCAC TTGCACTTGT CGATGCCGAT

5341 TCACTTGCGC TTGTGGATGC GGACTCACTT GCACTCGTTG ATGCACTTTC GCTTGCACTT

5401 GTGGATGCGG ATTCGCTGGC ACTAGTAGAA GCAGATTCAC TTGCGCTCGT TGATGCCGAT

5461 TCACTTGCAC TTGTCGATGC CGATTCACTT GCACTTGTTG AAGCAGATTC ACTTGCGCTC

5521 GTTGAGGCCG ATTCGCTGGC ACTCGTTGAT GCCGATTCGC TAGCACTAGT AGAAGCTGAT

5581 TCACTTGCGC TCGTTGATGC CGATTCACTT GCACTTGTCG ATGCCGATTC ACTGGCGCTT

5641 GTGGATGCGG ACTCACTTGC ACTCGTTGAT GCACTTTCAC TTGCACTTGT GGATGCGGAT

5701 TCGCTGGCAC TTGTCGATGC CGATTCACTG GCGCTTGTTG ATGCGGACTC ACTTGCACTC

5761 GTTGATGCAC TTTCACTTGC ACTTGTGGAT GCGGATTCGC TGGCACTAGT AGAAGCTGAC

5821 TCACTTGCAC TTGTTGAAGC CGATTCACTG GCGCTCGTTG ATGCACTTTC ACTTGTGCTT

5881 GTTGAAGCCG ACTCACTTGC GCTCGTTGAT GCACTTTCAC TTGCGCTCGT TGATGCCGAT

5941 TCACTAGCAC TAGTAGAAGC TGATTCACTG GCGCTTGTTG ATGCAGATTC GCTGGCACTT

6001 GTCGATGCCG ATTCGCTAGC ACTAGTAGAA GCTGATTCAC TTGCGCTCGT TGATGCCGAT

6061 TCGCTAGCAC TTGTCGAAGC TGATTCACTG GCACTCGTTG ATGCACTTTC ACTTGCACTC

6121 GTTGATGCCG ATTCGCTAGC ACTTGTCGAA GCTGATTCAC TTGCGCTCGT TGATGCTGAT

6181 TCACTGGCGC TTGTTGAAGC CGACTCACTT GCGCTCGTTG ATGCACTTTC ACTTGCGCTC

6241 GTTGATGCCG ATTCACTAGC ACTAGTAGAA GCTGATTCAC TGGCGCTTGT CGATGCCGAT

6301 TCGCTAGCAC TTGTCGAAGC TGATTCACTT GCACTCGTTG ATGCTGATTC ACTTGCACTT

6361 GTCGATGCTG ATTCACTTGC GCTCGTTGAT GCTGATTCGC TGGCACTTGT CGATGCCGAT

6421 TCACTTGCGC TTGTTGAAGC TGATTCACTT GCGCTTGTTG ATGCGGATTC GCTTGCACTC

6481 GTTGATGCAC TTTCACTTGC GCTCGTTGAT GCCGATTCGC TGGCGCTCGT TGATGCACTT

6541 TCACTTACGC TCGTTGATGC ACTTTCACTT ACGCTCGTTG ATGCACTTTC ACTTACGCTC

6601 GTTGATGCAC TTTCACTTAC GCTCGTTGAT GCACTTTCAC TTACGCTTTT TGATGCCGAT

6661 TCGCTGGCAC TCCTCGTTGA AGCGGATTCG CTGGCACTCC TCGTTGAAGC GGATTCACTT

6721 ACGCTCGTTG ATGCGCTAGT CGAAGTACTC GTCGAGGTGG ATTCCTGTTC ACTCTTACTC

6781 GTCAATTGA
```

-continued

*Lactobacillus reuteri* 3630_00804

SEQ ID NO: 31

```
  1 ATGGAGATAT TGGTAACGTT ATTTGATTTG GTGTTTTTTA TTACGTTTAT AGTCGCAATT
 61 GTCTATGGTA TTAGGTGGTT TAAAGGAAGA AAAGATAAAG AAAATGAATC TCTTAAGAAA
121 CGCCGTTTGT AA
```

*Lactobacillus reuteri* 3630_00827

SEQ ID NO: 32

```
  1 ATGATTAACT TAAACTTAGC AGGCTTAGAT TTTGTAATGA CGGCACTTTT TATTGTGTTG
 61 TTTACAGAAC AGTTGAAAAA TGCCCGAACT CAGCGTGATG CTCTGATTGG TTTAGCATTT
121 GCAATTATTT GTTTACTATT TTGCAACAAG AATGTTTTTC TATTAGTGAC ATTAGTAACA
181 CTTGTCGCAC TGTTTTCATT AAATTACTTA ATCACGAGGA GAAAAATGA CATTAACTGA
```

*Lactobacillus reuteri* 3630_00947

SEQ ID NO: 33

```
  1 ATGTCAGAGA TGAAAAATCG CGTAATTAAT TTTCGGAATG ATAACTTAGC CAAACTTATA
 61 GTCAATTATT ATGGAAATAG TCAATTAAGT GTGCATATTA CTAATAATAT GTTTTTTGAA
121 TGA
```

*Lactobacillus reuteri* 3630_01261

SEQ ID NO: 34

```
  1 ATGAAACGCA AAATTGCATT AGCTCAACTT GATATTCAAT TAGGAAATCC TGCCGAAAAT
 61 TATCAAAAAG CTAAACAAGC GATTGAAGAA GCTGCTAGTC ACCATGCAGA TATCGTTGTC
121 TTGCCGGAGA TGTGGAATGC TGGCTATGCC TTAGATCAAT TAGCAGAATT GGCAGATGAA
181 AACGGTCAAA AGACACAAAA ATTTCTTAGT GAGTTAGCGT TAGAAAATCA AATTAACATT
241 GTCGGTGGTT CAGTAGCGGT GAGATGTGGA CAATCTTTTT TCAATACAAC CTATGTTTAT
301 GATCAAAAGG GAAATCTAAT TAGCAGTTAC GAGAAGGTGC ATTTATTTGG ACTAATGAAT
361 GAAGACCGAT ATCTAAAAGC CGGGCAAAAA GAAATCACT TTGAATTAGC TGGGGTTCCG
421 AGTGCAAGTT TTATTTGTTA TGATTTGCGA TTCCCTGAAT GGATTAGAAC AGTCACTCGT
481 TATGGAACTG ATATCTTATA TTTTTCGGCA GAATGGCCAA GCAAACGGAT TAAACAATGG
541 AAAATAATGC TTCAGTCACG GGCAATTGAA AATCAAGCCT TTGTAGTCGC GGTCAATCGT
601 GTTGGGACGG ATTTAGAGAA TAGCTTTAAT GGTCATTCGT TAGTAATAGA TCCGCTTGGG
661 CAGATTATCC ATGATGCAGG AGAAGTTGAA CAAGTAAGTT ATGCAGAAAT TGACTTAGCG
721 CAGTTAGCAC AGGTTCGGGG GCCGATTCCG GTGTTTAAGG ATCGCCGACC AAGTCTTTAT
781 CATTAA
```

*Lactobacillus reuteri* 3630_01695

SEQ ID NO: 35

```
  1 ATGCAAAATA AGATGCTTG TACATCAATT ATGGTCGGTA AAAAGGCTTC TCTCGACGGT
 61 GCTAATTATA TTGCTCGTAA TGAAGATCGC GTAAAAGCAA TTGAACCCAA GCGATTTTTA
121 GTAAAACCGG CAGTAAAAGG ACGCCACGAA ACCTACGTAT CACCTTACAA TAAAGTAACT
181 GTAGCTTTGC CGGAAGAGAG AATGCGTTAT ACTTCTACGC CTACCCTTGA TCAAACAGCC
241 GGACCTAATG AAGAAGATGG AATTAATGAA GCAAATGTGG CAGCTTCCTT TACTGAGAGT
301 GTTTATGCAA ATGATCGGGT GTTAGCATAT GATCCATACG TAAAAAATGC CCTGGCAGAA
361 GACTCACTTT GTACTTTAGT ATTACCGTAT ATTCATTCTG CCCGTGAAGG AGTTGAATAT
421 ACTGGAAAAT TAATTGCTGA ATTGGGCTCT GCTGAGGGAA ATGGAATGCA ATTTGCAGAT
481 GCAGATGATA TTTGGTATAT GTAA
```

*Lactobacillus reuteri* 3630_01889

SEQ ID NO: 36

```
  1 ATGAATTATT TTATCGGTGT TGATGTTGGA ACTACTTCTA CAAAGGCAGT TCTATATGAC
 61 CAAAATGCAA CTGTGTTAGA TCAATTTAGC CAAGGTTATT CCCTTTACCG CGATGCTAGT
```

-continued

```
 121 GGAATGGCTG AACAAAACCC AACTGCAATT GTCGAAGCAG TCGAAAAAGT TATTCATGAT
 181 GCAGCACAAA AAGCAGATTT AACAAATGGA AAATTGTTAG CGGTATCATT TTCTAGTGCT
 241 AACCAAAGTG TGATTATGCT CGACAAGAAT TTCAATCCCC TTTCACGGGT CATCACTTGG
 301 GCTGATACCC GTGCACGTGA TGTCGCCAAC GAATTAAAGA ATAGTCCTGC TGGTCAGCAA
 361 ATCTATGCTA AAACAGGTAC ACCTATTCAT CCAATGTCCC CATTGACCAA GATTATGTGG
 421 CTCAATAAGA CACAAGCAGA TAAGGTTGCT CAAACTGCAT ATTTTGGCGA TATCAAATCC
 481 TACCTCTTCC ACCAGTTTTT CAATACATTT AAGGTTGATG TTTCCATCGC TTCATGTACC
 541 GGAATGATGA ATGTCAATAC GTGTGACTGG GACGATCAAG CATTGGAACT CGCTAACGTC
 601 GACTGTTCCC AATTACCAGA ATCGTGAAC GGAACAACCC AAGCGATTGG CCTAACAGCA
 661 GCGGCGCAAG CAAAAATGGG TATCCCCGCT GACACGCCAT TTGTCTATGG TGCCTTTGAC
 721 GGTGCTTTAT CTAATTTAGG TGTGGGGGCA ATTAAGCAAA ATACTGTTGC CATTACGATT
 781 GGAACTTCGG CTGGTGTTCG GTAGTAACT GACCATCCAG TGATCGATCC TCAGCAACGA
 841 CTCTTCTGTT ACGCCGTGGA TAAAGGTTTA TGGGTCATCG GCGGTCCGCT TAATAATGGT
 901 GGCGATGTCT ATCAGTGGGC CGTTGAACAC TTAGTTGACG CTAGTGCAGT TAAAAATGAA
 961 AATATTGATC CCTACACTCT TGCTAACCGA GTTATTGAAG GTGTTCCCGC CGGAGCTCAC
1021 GGTTTGCTCT TCCACCCATT CCTTGGCGGT GAACGGGCAC CATTATGGGA CGCTAATGCG
1081 CGCGGTAGTT TCTTTGGACT TTCCCACATT CATACTCGTG CCGATATGCT GCGCTCAGTA
1141 ATGGAAGGAA TTTGTATGAA TATTGCAACT GTTTTCCAAG CGGTTCGTGA TCTTGTTGGT
1201 AATCCTGCAA GCGTAACTGC AACTGGCGGT TTTGCGCGAG CTGAAGTTTG GCGGCAAATG
1261 TTAGCAGATG TCTTGAACTG TCCGGTCAAT ATCCCGAACT CATTTGAATC TGGTTGTCTC
1321 GGTGCAATCA CCATGGCAAT GAAGAGTTTA GGAATGATTG AAAACTATGA AATCATTAAA
1381 ACATTAGTTG GTGATATCAG TTCTTATCAG CCAAATCAAG ATGCGGTTAA TGTTTATCAA
1441 AATTACTTAC CACTTTTTAA GCAGGTCGAA GGATTATTAA CACCAGCCTA TTCGACCATC
1501 GCTAAATTAC AACAACAATC TACTACTCAT TAG
```

*Lactobacillus reuteri* 3630_01932

SEQ ID NO: 37
```
   1 ATGACAACAT CAATGATCCA CAGTAGAAGT ATGTTGGCGA AAGTGATTGC AGAATCACCT
  61 TCACCTTTTA TTATACCAAT TTTTTGTCCT AATGTAATAA AGATTATCTT TTTATCTATA
 121 AATTATTTTA TGAAAAGAGT GGAAAAGGCA AGAAGAGCAA TCAAAAAGCC AATTTTAACA
 181 ATTTTATTAA GTTGA
```

*Lactobacillus reuteri* 3630_02243

SEQ ID NO: 38
```
   1 ATGAGCAAAC TATTACTTGA TGAAAGACCG TTACAAGTTC AGGCATCGTT AGCTGGAGCG
  61 TTGAAAAGCT TAGACGAAGC TGTTATTCTC CAGCAGCTTC ACTATTGGCT TCAACGTTCT
 121 AATACAGTAA GAGACAATCA CAAATGGGTC TATAACAGCA TGGCTGATTG AATAAACAG
 181 TTCCCTTGGC TTTCTAGAAA GGCTCTATCG AACCACTTTA AGAAATTAGA AAAACGAGGA
 241 CTAATTATTA CAGGCAACTA TAATAAATTA TCTTTTGACA AAACAAAGTG GTATCGAATT
 301 GACTATGACG CATTTTCCCA TTTGGAACAA CGATTGGGTA GAAACTACCC AACGAATGGG
 361 AAGAATCTAC CCAATGGAGA CGGTAAAAAC TGCCCAATCG GAGAGGAAGA ATCTACCCAA
 421 CCAATACCAA TAGACTACCA AGAGACTACA CAAAGACTA CTACAAGAGA TAAAGGGCAG
 481 GCACAGCCAG CCCAACCTTC CATTGCTGCA CAGCGGCGAG AAGTTGTTGA ATATCTCAAT
 541 CAAAAAAACT GGCAAGCACT TCAAGCCTGA
```

-continued

*Lactobacillus reuteri* 3630_02365

SEQ ID NO: 39

```
  1 TTGAATAATT TTCAAAAGGC AATTTTCTTG TTGCAGAATA TCGACAAGCT TAAACAGCTT
 61 AATGGTAAAG CGATGACTCT TACTGAGTTC TCTAAAATAA CTGATGTTTC ACGGCCAACG
121 TTGTATAAAT ACATTCAGCA TCCAGAAACA ATGAGTAGTT CGTTTGTAAA TAAAGCGGCC
181 ATGCTCTACG ACAAGGTTGT TAAATTTCAA GATATTCTTG ATACAGTTCA GCGTGAAGAT
241 AAACAATTTA AGACTACCAG GCAGGAATTG ATTAAGCTTT TAGAGTCTAA TGTAGCTAAT
301 ATTGAAGTTA CAGATTATAC AAAAGCAATC GCGACAGTAA TTATTAGTGA CTTAAAAGAA
361 GAAAATTCAA GTCTGCTAAA AGCGTTAAGT AAGCAATTAC CATTTAAACC AAATTTAAAT
421 GATAATTTGT CAAAATAG
```

*Lactobacillus reuteri* 3630_02435

SEQ ID NO: 40

```
  1 GTGAAGATGA ATAGTATGAC AAACAACCAA AAAGAAAGTT GGAACGTTGG CAACTATAAA
 61 ATCAATGTAT TACCAGATGA TGAGTTCCAG CAATTGTTAA AGAACCAACG CCAACTTCAA
121 CAGATCATTG AAAGTATGCC ACTACCAACC GACCCCAATG TTGATCTAGT TAAAAAGATT
181 CATTCCCAAC TCCCTATTAC AAACTGGGCT TGGGAATTAA CTAAACAACG AGAACATGAG
241 GAAAAGTTAA AGAAACAAAA GCAGCGAATT GCACAGCAAT CGCTTAACTA TCCAACAAAC
301 CTCAAGAAAC CGGATAATGG CCTTTCCCTA TAA
```

*Lactobacillus reuteri* 3630_02436

SEQ ID NO: 41

```
  1 ATGAATTCTA ATTTGAAAAA GAATTTGATT ATCGCAAATG GATTTCTACT ACTAATAATA
 61 ATATTTTATG TTTTATTACA TATGGGTCCA TTAAATATGA AAGTCTTATT AGTAGGATTG
121 GTATTAATGA ATCTGACAGT AATATTTAAA TAA
```

*Lactobacillus reuteri* 3630_02437

SEQ ID NO: 42

```
   1 ATGGATAAAT TAACATTGAA AAAACTAATT ATTATTACAT TAGGCATGCT AATGGTATTT
  61 CTTTTAGGTA TGCACCTTCA TCAAAAGACA CACTTTAACA AAAACGTGAA GATTAATAAT
 121 ATTCCAGTCG GAGGTCTTAC TGTTCAACAG GCATATAATA AAGTAAGTAA TACTAAAAGA
 181 AAATCAAAAA TCTACATTAA CAAAAAGTTA GTTTATTCAG GTAAAAGTAC TGACTCAGGT
 241 TTTAAGTTAT CTGATAAAGA AAGATTTAGT AAGGCGTTAC ATTACCAATA CACTTTTTTT
 301 CCCTCACGAA AACATGAAAA TTTGCTAGTT GAGCCAGCTG ATTTAGATAA GTCAGCGTTA
 361 AATAATATTG ATTCGGCAAT AGTAGCTAGG ATTCATCAGC TCAATATAGG CAGAAAGGCC
 421 CCACGTGATG CATACGCCGT TTACCAGAAT AATAAAGTTT CAGTTATTCC AGCAATTGAT
 481 GGGACACGAT ATAGTGAACA AGGACTTTGT AATATTGCTA ATAAGGAATT TGTTAATGGG
 541 ACAATTCATT TAACTCCTAA GGTTATTACT CCTTTATCGG CAAACAGTAA AGTAGTTCAA
 601 GATGAAAAGA AACACCTGAG TAAACTACAA AATCGATCGG TTGTTTATCA GGTTCAGAAA
 661 ACAAAATATA ATTTTAAAGC GTCTAATGTC ATTTCTAAAG CAACTTATCA GCATGGGAAA
 721 TACCATTTTG AAACTGACAA CGTTAAATCC AAGATTGCCA ATATAAATAA TAAGCAAGCA
 781 ACATTAGGAA AGAGCTTTAA ATTTAGAACT GATTCTGGAA AAGTTATTTC TACATCTAAT
 841 CAGGGAACAT ATGGTTGGAA ATAAGTAGC AAGCAGGCAG GACAAACACT CTCTAAAGCG
 901 TTAGCTAATA ATGTTAAGAG CGTTAATGCC GAAATGATA TTTACGGTAA AGGCTATAGT
 961 CATCTTGGTA CTGGATATTC GGCTGTGAAT AATCATGGGC TTGGTAATAC TTATGTGGCT
1021 GTATCATTAG CTAAACAGCA TGCTTGGTTT TATAAAAATG GAAAATGTGT ACTGAGTACA
1081 GATATTGTTA GTGGATCAGA TGACGCTAAT AATAGGACTC CTAAAGGTGT TTGGTATATC
1141 ATGTATCAAC AAACGCCATC AGTTTTACGT GGGACTAATG ATGATGGTTC CAAGTATAGT
```

-continued

```
1201 AGTCCTGTTC AGTATTGGTC TCCGTTTACT TTATCAGGGT GTGGCTTTCA TGATGCTAGT

1261 TGGAGGCATA ATTGGTCTAA AACAGCTTAT AAACAGACTC ATGGTGGCTC ACATGGCTGT

1321 ATTAACATGC ATCCGGAAAA TGCAGGAGAC GGTTTCCATG CCCTTACTAA AGGAGAACCG

1381 GTAATAATTT ATTAG
```

*Lactobacillus reuteri* 3630 02438

SEQ ID NO: 43

```
   1 ATGCAATTAA ACCATAAATT AGGAGTTTTC TTGGCAGCGC CATTTGCTCT ACTGGTTTTA

61 TCAGCTACAA ACGTGCATGC CGATAACATT CAAAGTAATA GTAACCAGAC AATCAGTAAT

121 ATGAGTTTGC AAACTAATGA CACAAAGACT CAACAAAATG TTGTAATGTC AAACGATGCA

181 AAAGCTCAAA TTACTGTAAA TCCTAGTTCT AATGCTAATT CTAGTTCTGT AGCAAAGATA

241 AATGAAAAGA ATAATGTAAA ATCGGATACT GACAATACTA ATGTCGAATC AAATGCTGAT

301 AATATTGGGA ACATTGCTTC TAGCGATTCC ACGGCAGTGG CTAATTCTGC TAGTTCCGAT

361 AATATTCAGT CATTTAACGT AAATACGCAG GAACAGCCTG CAATAAATGT ATCTGAACTA

421 ACAACCGAAG AGTATGTTAC GAATTACACT CAACAACAGA TCAATAATGC GACGACTATT

481 CATGATTACT TTATAAATCA AGGATGGACA CCAAATGCTA TTGCTGGAAT GCTTGGTAAC

541 TTTGTTTCAG AGTCAGGTTT AATCCCAGAC TTACATCAAT ATGGTGGTGG GCCTGGTTAT

601 GGGTTAGCTC AATGGCCATT TAATAGTGTA GTAAATTGGT GTCGTAATAA TGGATATGAT

661 TATCGTACTT TGCAAGGACA ATGTGCATAT ATTGAATATC AAATGACTCA TGGACAGCAG

721 TATTATCCAT CAGCTTACTC TAGAATGACC GCTAATGAAT ATATGCATAG TTATGCTTCA

781 GCATATACTT TAGGTATGAT TTGGCTTAAT AACTTTGAGC GACCTGCAAA TAGGAATCAG

841 CCAGCTCGTG GTCAACAGGC TCAATACTGG TATCAGTATT TCCAAAGTCA TGGTTCTACA

901 TCAGCACCGG TACAACAAAA TCCTAGTACA CCAGCAACAA CTCCTAGCTC AAGTCGAATG

961 AGTCAACACG GGACATTCAA AGTTGCTTAT GGATTAAATG TACGCCAAGC ACCAAGTACA

1021 TCGGCAGCTA TTGTAACGTA TTACAATGGT GGTCAAAGCT TTACATATGA TTCAAAGATT

1081 GAAGCTAACG GGTATCTTTG GTATCATAC ATGAGTTATA GTGGCGTACG TCGTTATGTT

1141 GCAATTAAGA ATTTGAATAA TGGAACGACT TACGGTTATG ATTCGAATAA CTTCTCATAC

1201 AGTGCTCCTG CATCTTCAAC ACCATCTACT AATGTGCCAA GTACGCCAGC ACCAAGTACA

1261 TCTACTTCAT CAACTGAGAA GCAATATGGA ACATTCAAAG TTGCTTATGG ATTAAATGTA

1321 CGCCAAGCAC CAAGTACATC GGCAGCTATT GTAACGTATT ACAATGGTGG TCAAAGCTTT

1381 ACATATGATT CAAAGATTGA AGCTAATGGG TATCTTTGGG TATCATACAT GAGTTATAGT

1441 GGCGTACGTC GTTATGTTGC GATTAAGAAT TTGAGTAATG AACAACTTA CGGTTACGAT

1501 TCAAATAACT TTTCATTTAA TGGGACTCCA GTAACATCAA ATAATAATCC TTCTAGTACT

1561 CCGGCAGTTC CGCAAGGTAA TAAGGGCCAA CAAGTTGTTG CTCTTGCACG TCAACAAATA

1621 GGTAAACCTT ATGTTTGGGG AGCAACCGGT CCTAATTCGT TTGATTGTTC AGGACTCGTG

1681 CAGTATGTTT ATCGTCAAGT TGGTGTTAAC TTACCACGGA CTACAACTCA ACAAGAATAT

1741 TGTGGACATG CTGTAAGCTT TAATAATCTT CAACCTGGAG ATCTAATGTT CTGGGGAAAG

1801 TATGGTAGTG CATATCACGT TGGAATCTAT ACCGGAAACG GTAATGTTTT ATTTGCACCG

1861 CAACCTGGTC AAACAGTTAA GGAACAACCA ATGCGCTATT ACATGCCTGC CTTTGCAAGA

1921 AGAGTATTGT AA
```

The present disclosure in ay be better understood with reference to the examples, set forth below. The following examples are put forth so as to provide those of ordinary skill in the art with a complete disclosure and description of how the compounds, compositions, and/or methods claimed herein are made and evaluated, and are intended to be purely exemplary and are not intended to limit the disclosure.

Example 1. *L. reuteri* Strain Identification

Seven *Lactobacillus reuteri* (*L. reuteri*) strains were isolated from older birds at the Research Center, Hannover from the cecal contents received from the Poultry Clinic, University of Hannover. All the seven strains are identified to be *L. reuteri* by 16S rRNA sequencing.

While only limited growth is observed for most strains under aerobic conditions in MRS broth and agar (de Man, J. D., Rogosa, M.; and Sharpe, M. E."A Medium for the Cultivation of Lactobacilli". *J Appl Bact.* 3: 130-135 (1960)), all isolates show very good growth on MRS agar and MRS broth under anaerobic conditions at 39° C. Culturing the bacterial strains on blood agar under anaerobic conditions results mostly in limited growth. None of the strains is able to grow in Mueller Hinton broth under anaerobic conditions. For all further analysis, bacterial strains are grown in MRS medium under anaerobic conditions at 39° C.

Antimicrobial susceptibility of bacterial isolates were tested using the AVIPRO® PLATE. All strains are resistant against colistin, doxycycline, enrofloxacin, erythromycin, neomycin, oxacillin, penicillin G, trimethroprim-sulfamethoxazole, tetracycline, tilmicosin and tylosin. All strains are resistant to streptomycin except strain 3632, and to tiamulin except strain 2098. In addition, resistance to cefpodaxime-proxetil is observed with strains 2091, 2095, 2097 and 3630; resistance to cefotaxime is observed with strains 2091, 2095 and 2097; and resistance to lincomycin is observed with strains 3630 and 3632. No strain was found to be resistant against amoxicillin, ceftiofur, erythromycin D, lincomycin-spectinomycin, and rifampicin under tested concentrations.

Example 2. *L. reuteri* Strain Selection and Anti-Infective Activity

To select the best strain for further use as a priobiotic, the *L. reuteri* isolates were tested for various desirable probiotic anti-infective properties, such as growth kinetics, ability to produce hydrogen peroxide, autoaggregation, enzyme profile, survival in the presence of ox bile and pancreatic enzymes, and sensitivity to heat shock and pH changes. The *L. reuteri* strains are also tested for safety using a haemolytic assay.

In general, all strains behave very similar in terms of probiotic properties, including growth kinetics and ability to produce hydrogen peroxide, except for strain 3632, which shows some unique properties, including the ability to autoaggregate in liquid media (comparable to that of the well-characterized human probiotic strain *L. reuteri* ATCC 23272). In addition to autoaggregation, *L. reuteri* 3632 also appears to produce an orange pigment, which resembles beta carotene in color. None of the other strains, including the human *L. reuteri* strain ATCC 23272 and *L. acidophilus*, produced orange colored pigment. None of the strains is found to be hemolytic on blood agar plates, suggesting that these isolates are less likely to be pathogenic to humans.

Whole-genome sequencing was performed for *L. reuteri* strains 2091, 3632, 3630, and an independently isolated *L. reuteri* strain 170331 of European origin, using PACBIO® sequencing (Amplicon Express). Sequencing, assembly and annotation statistics are summarized in TABLE 1. Genomic structures and organization differs among the tested strains.

TABLE 1

| Strain | 170331 | 2091 | 3632 | 3630 |
| --- | --- | --- | --- | --- |
| Genome size | 2,090,596 bp | 2,231,245 bp | 2,482,713 bp | 2,399,045 bp |
| Contigs | 9 | 11 | 7 | 5 |
| Coding Sequences (ORFs) | 2,154 | 2,280 | 2,595 | 2,467 |
| Ribosomal Binding Sites | 2,231 | 2.354 | 2,680 | 2,467 |
| Transcription Terminators | 1,123 | 1,123 | 1,375 | 1,339 |
| Operons | 452 | 472 | 541 | 475 |
| tRNA | 75 | 61 | 77 | 73 |
| rRNA | 18 | 19 | 13 | 18 |
| Other RNAs | 39 | 99 | 89 | N/A |
| CRISPR | 1 | 0 | 0 | 0 |
| Prophages | 7 | 1 | 8 | 5 |
| Islands | 30 | 22 | 24 | 9 |
| Bacteriocins | 0 | 1 | 4 | 3 |

Example 2.5. Colonization of *L. reuteri* 3632 in 16-Day Old Embryos

The goal of this study was to test if *L. reuteri* 3632 colonizes the intestine of 16-day old embryos. To this end, 16 day-old embryos were obtained from Charles River and inoculated with 10^8 CFU/embryo of *L. reuteri* 3632 by air cell, yolk sac and allantoic routes. Embryos were sacrificed on 18 days and the intestines were harvested and plated on MRS agar plates. An un-inoculated group was included as a control. *L. reuteri* was recovered from the intestines of the majority of the embryos, suggesting that *L. reuteri* 3632 colonizes the intestine of 16-day old embryos. *L. reuteri* 3632 was not recovered from any of the control (uninoculated) embryos, even after 2-days of enrichment in liquid culture.

Example 3. Co-Culture of *L. reuteri* and *C. perfringens* in Brain Heart Infusion (BHI) Broth

Figure 9:
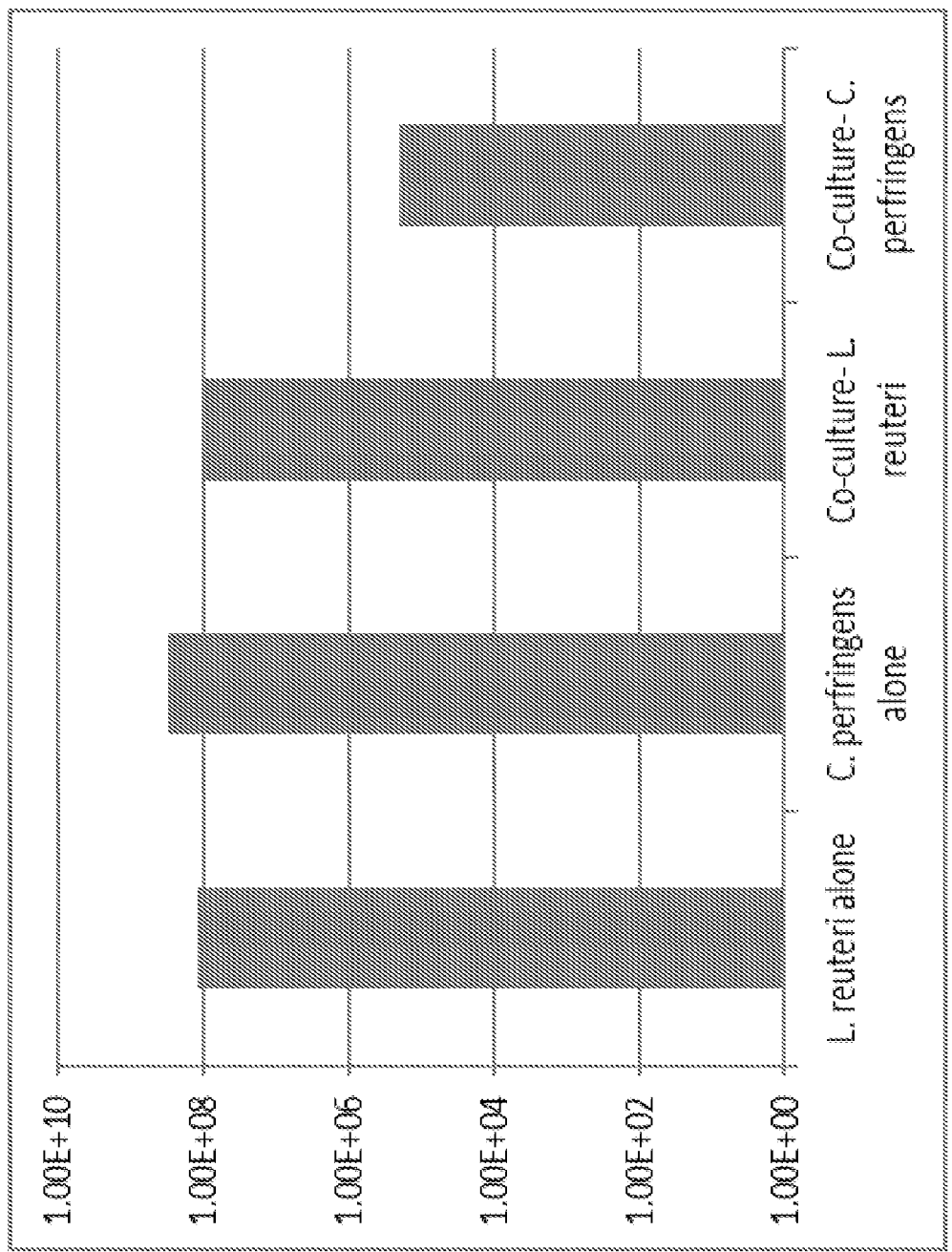
FIG. 9 depicts quantification of in vitro kill effect of *L. reuteri* strain 3632 on *Clostridium perfringens*. In a co-culture experiment, *L. reuteri* appears to inhabit *C. perfringens* growth almost by 4 logs. CFU counts were determined 24 hours after coculture in BHI broth. *L. reuteri* were enumerated on MRS agar plates and *C. perfringens* was enumerated on OPSP plates. This data is from one representative experiment of 3 replicates. Co-culture-*L. reuteri*, *L. reuteri* recovered from co-cultured sample using *L. reuteri*-specific media. Co-culture-*C. perfringens*, *C. perfringens* recovered from co-culture sample using *C. perfringens*-specific media.

*L. reuteri* and *C. perfringens* were cultured in BHI broth. CFU counts were determined 24 hours after coculture in BHI broth. *L. reuteri* were enumerated on MRS agar plates and *C. perfringens* was enumerated on OPSP plates. This data is from one representative experiment of 3 replicates. Co-culture-*L. reuteri*, *L. reuteri* recovered from co-cultured sample using *L. reuteri*-specific media. Co-culture-*C. perfringens*, *C. perfringens* recovered from co-culture sample using *C. perfringens*-specific media. See FIG. 9.

Example 4. In Vivo Effects of *L. reuteri*

Birds were vaccinated with CocciVac on day 0 and fed with *L. reuteri* in feed from day 0 to day 42 @ 10^7 CFUs/Kg of feed. A separate group of birds were fed with feed supplemented with bacitracin methylene disalicylate (BMD_55).

Figure 1:
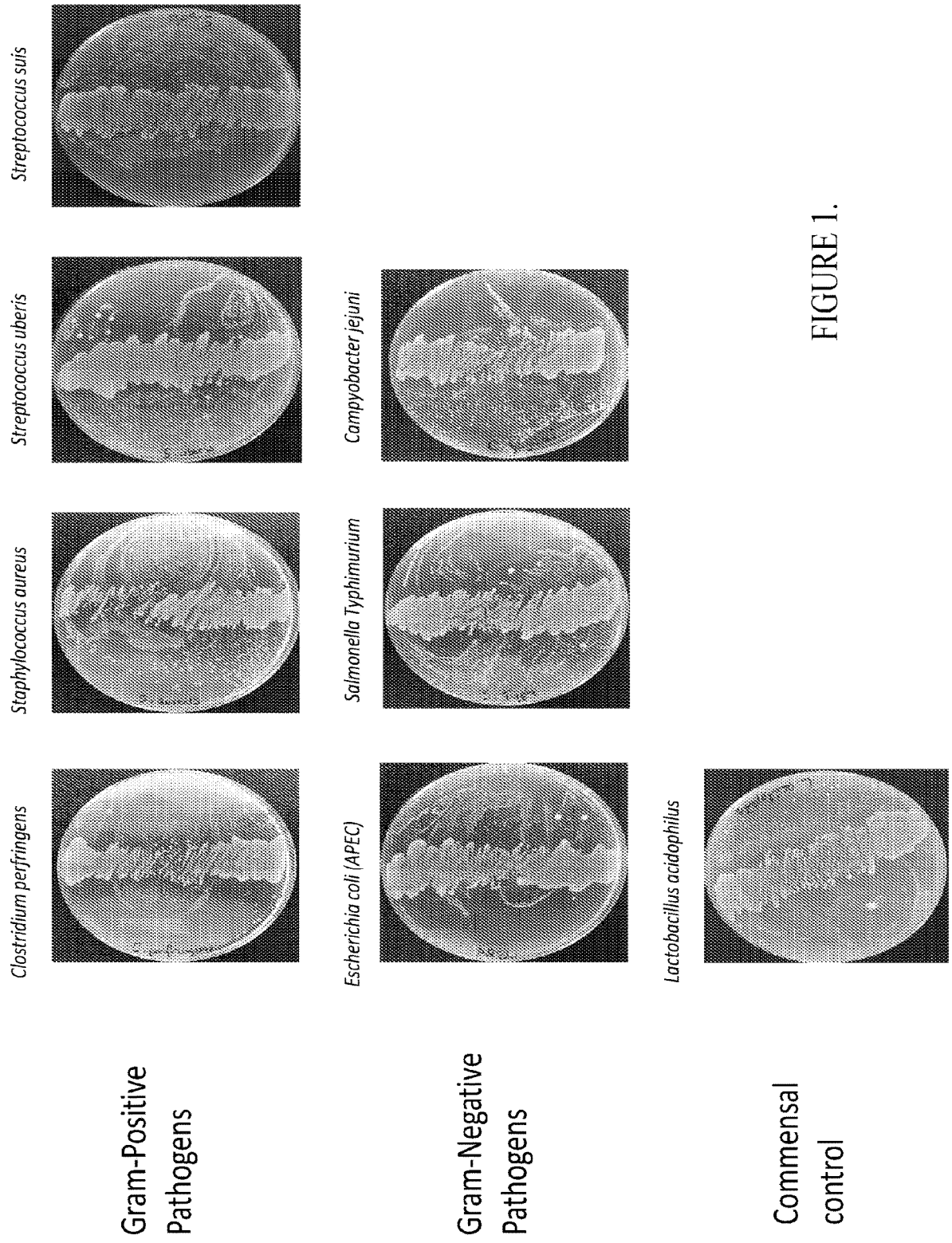
FIG. 1 depicts antimicrobial effect of *L. reuteri* strain 3630. Pathogenic bacteria, but not nonpathogenic *Lactobacillus acidophilus* are killed by *L. reuteri* strain 3630, as evidenced by a clear "halo" surrounding strain 3630. Pathogenic bacteria shown are gram-positive pathogens *Clostridium perfringes, Staphylococcus aureus, Streptococcus uberis, Streptococcus suis*; gram negative pathogens are *Escherichia coli, Salmonella Typhimurium*, and *Campylobacter jejuni*.
Figure 2:
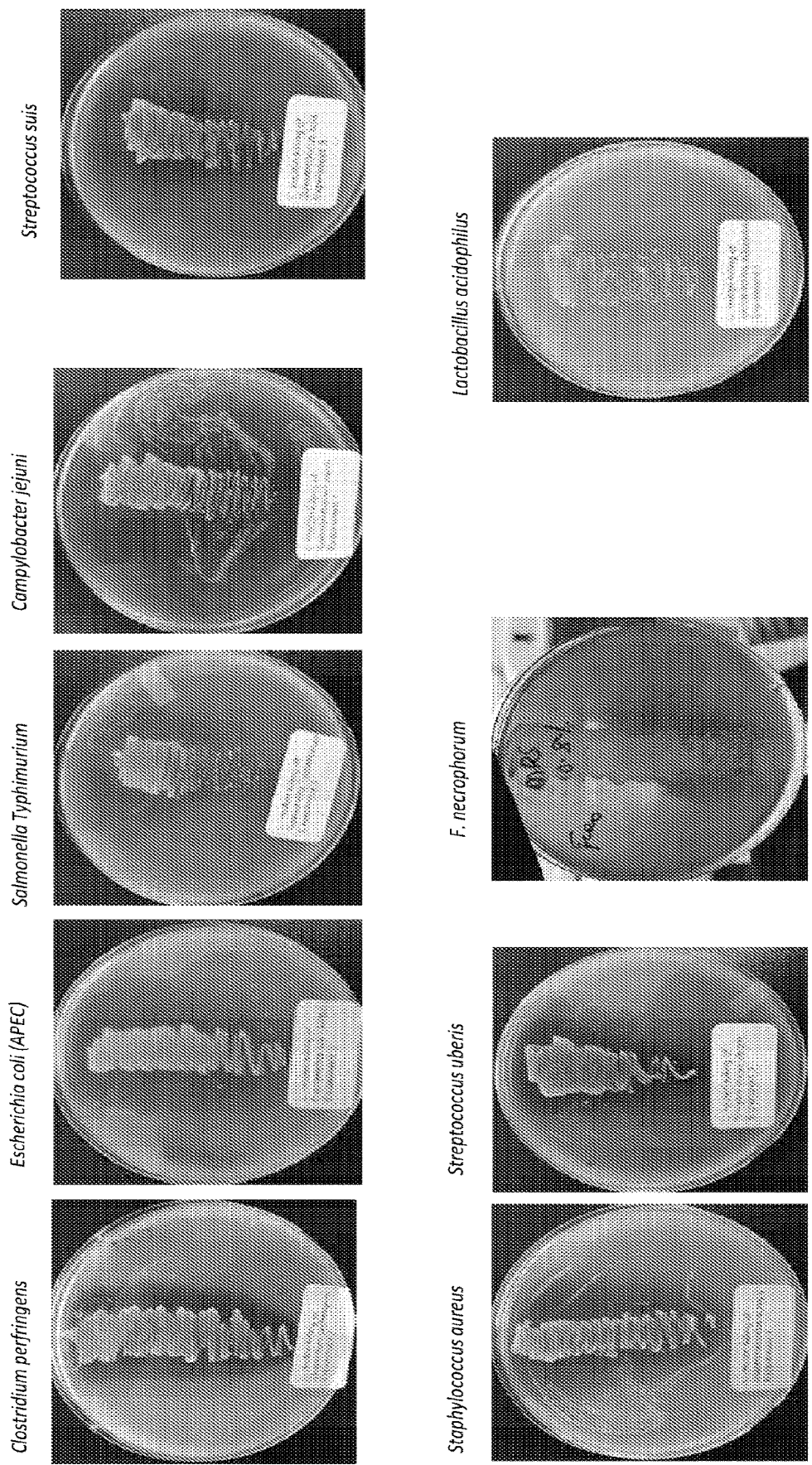
FIG. 2 depicts antimicrobial effect of *L. reuteri* strain 3632. Pathogenic bacteria, but not nonpathogenic *Lactobacillus acidophilus* are killed by *L. reuteri* strain 3632, as evidenced by a clear "halo" surrounding strain 3632. Pathogenic bacteria shown are *Clostridium* perfringes, *Staphylococcus aureus, Streptococcus uberis, Streptococcus suis, Escherichia coli, Salmonella Typhimurium, F. necrophorum*, and *Campylobacter jejuni*.
Figure 3:
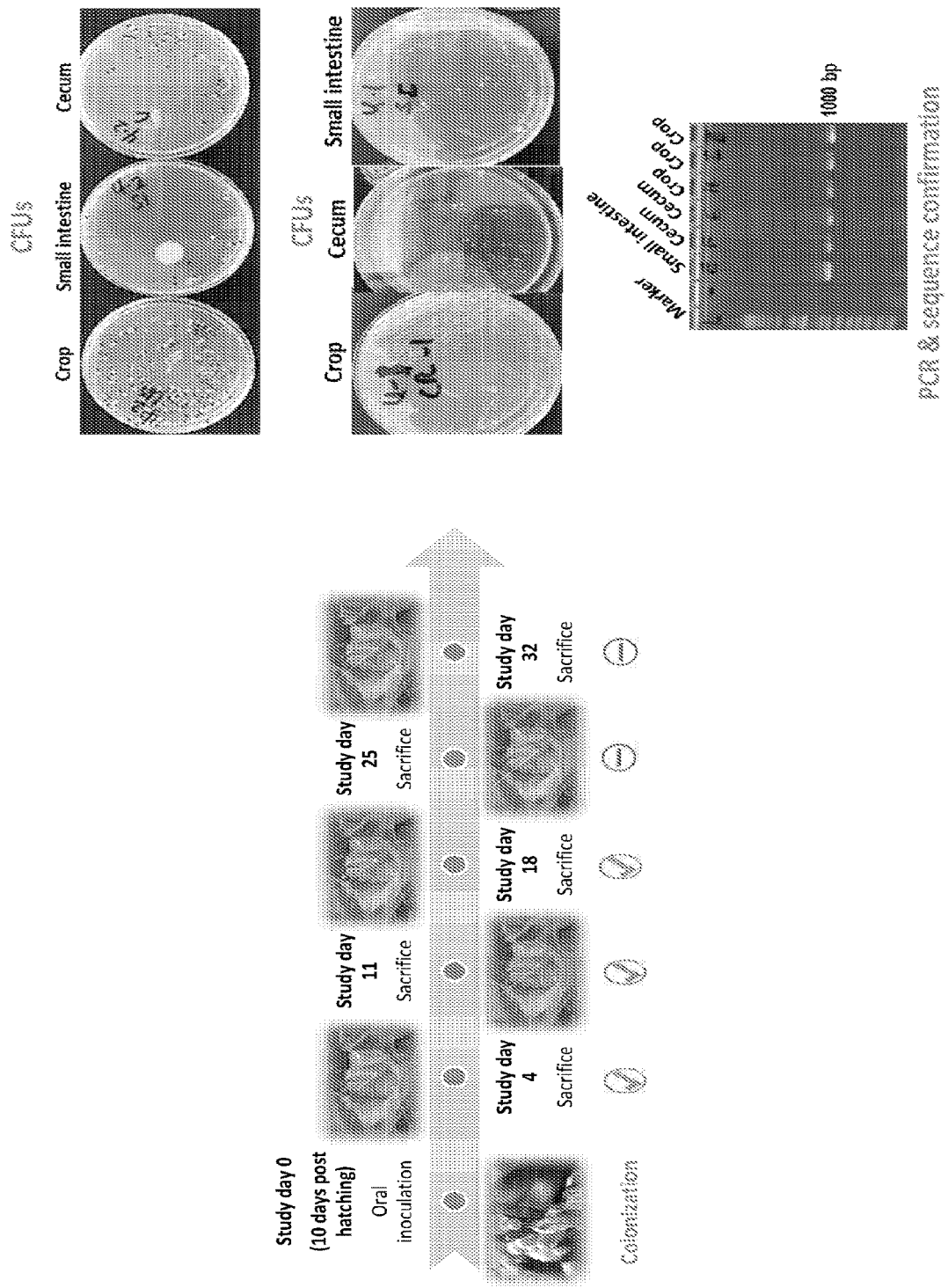
FIG. 3 depicts colonization of *L. reuteri* strain 3632 in chickens, via oral administration route. Left shows the experimental timeline. Right shows colony formation and PCR & sequence confirmation.
Figure 4:
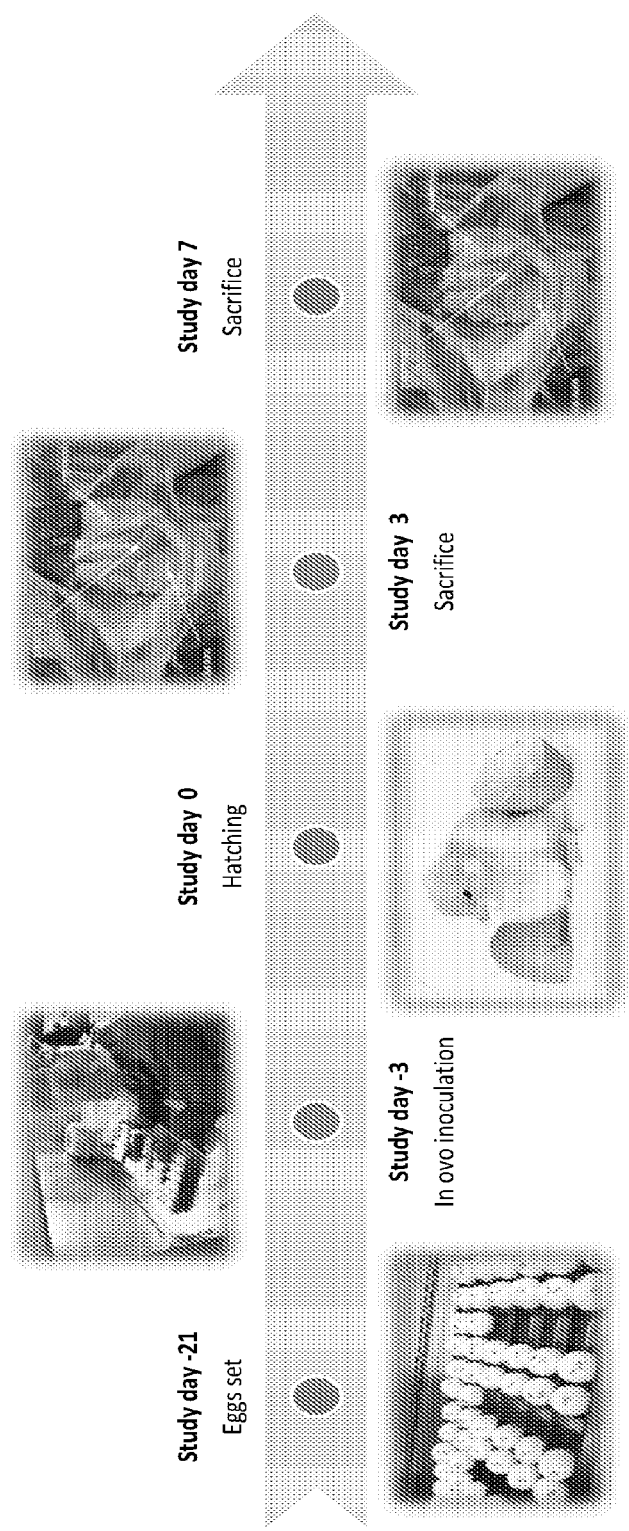
FIG. 4 depicts experimental timeline to determine colonization of *L. reuteri* strain 3632 in chickens, via in ovo administration route. Chicks were harvested at day 3 and day 7, and the strain is characterized.
Figure 5:
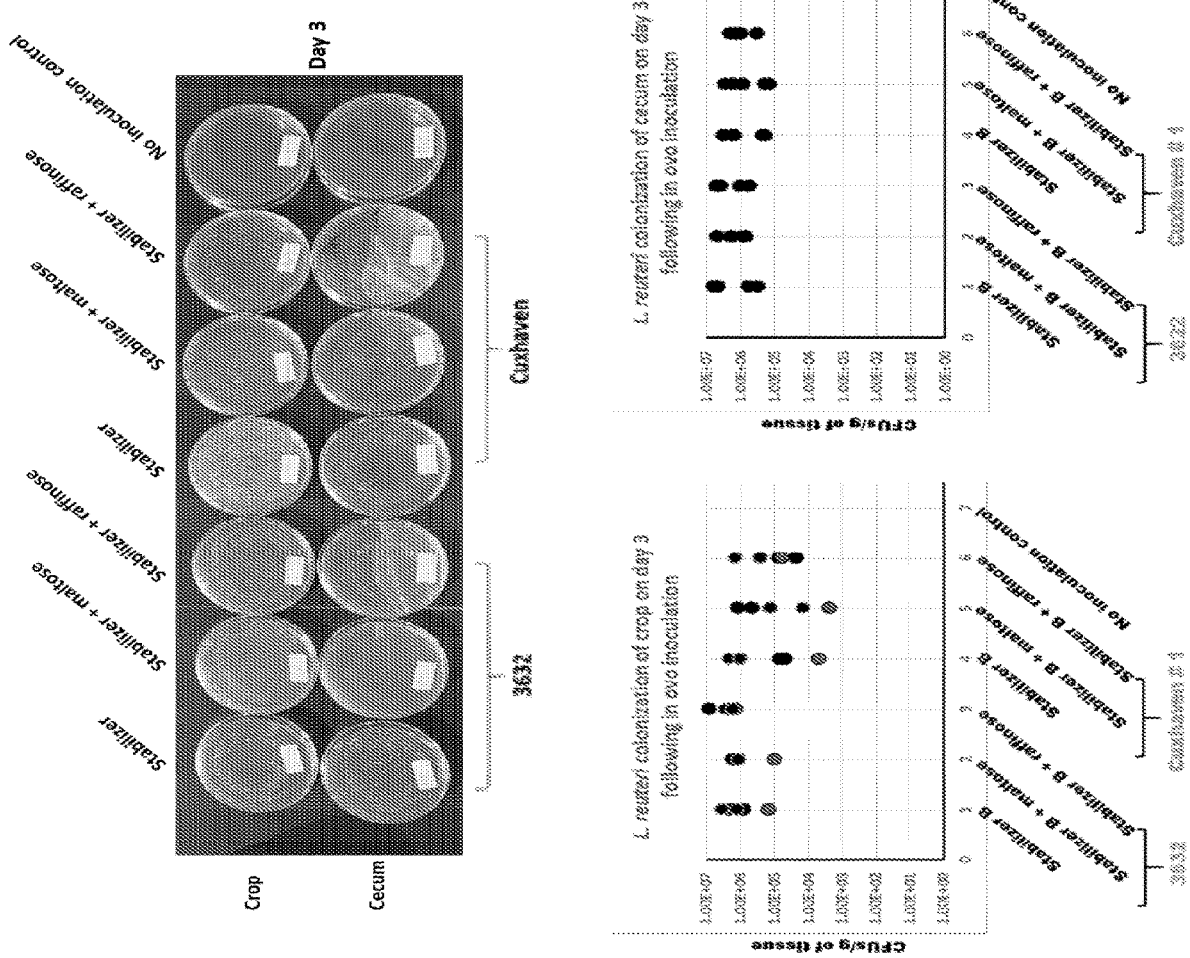
FIG. 5 depicts colonies from chicks sacrificed at day 3. Strain 3632 is found in the tissues of chicks at 3 days post hatching, while colonization of a control strain declines after day 3.
Figure 6:
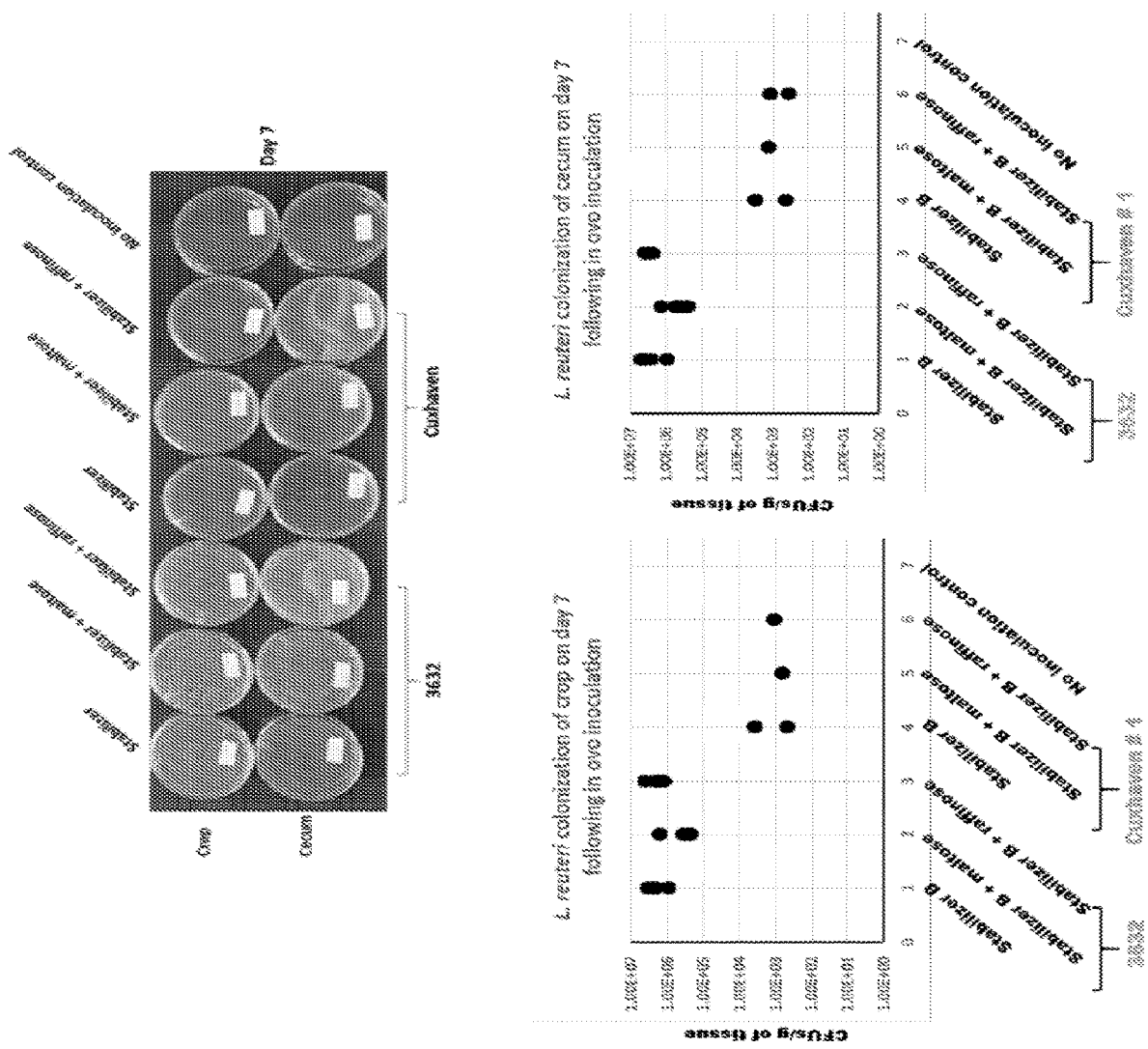
FIG. 6 depicts colonies from chicks sacrificed at day 7. Strain 3632 is found in the tissues of chicks at 7 days post hatching, while colonization of a control strain declines after day 7.
Figure 7:
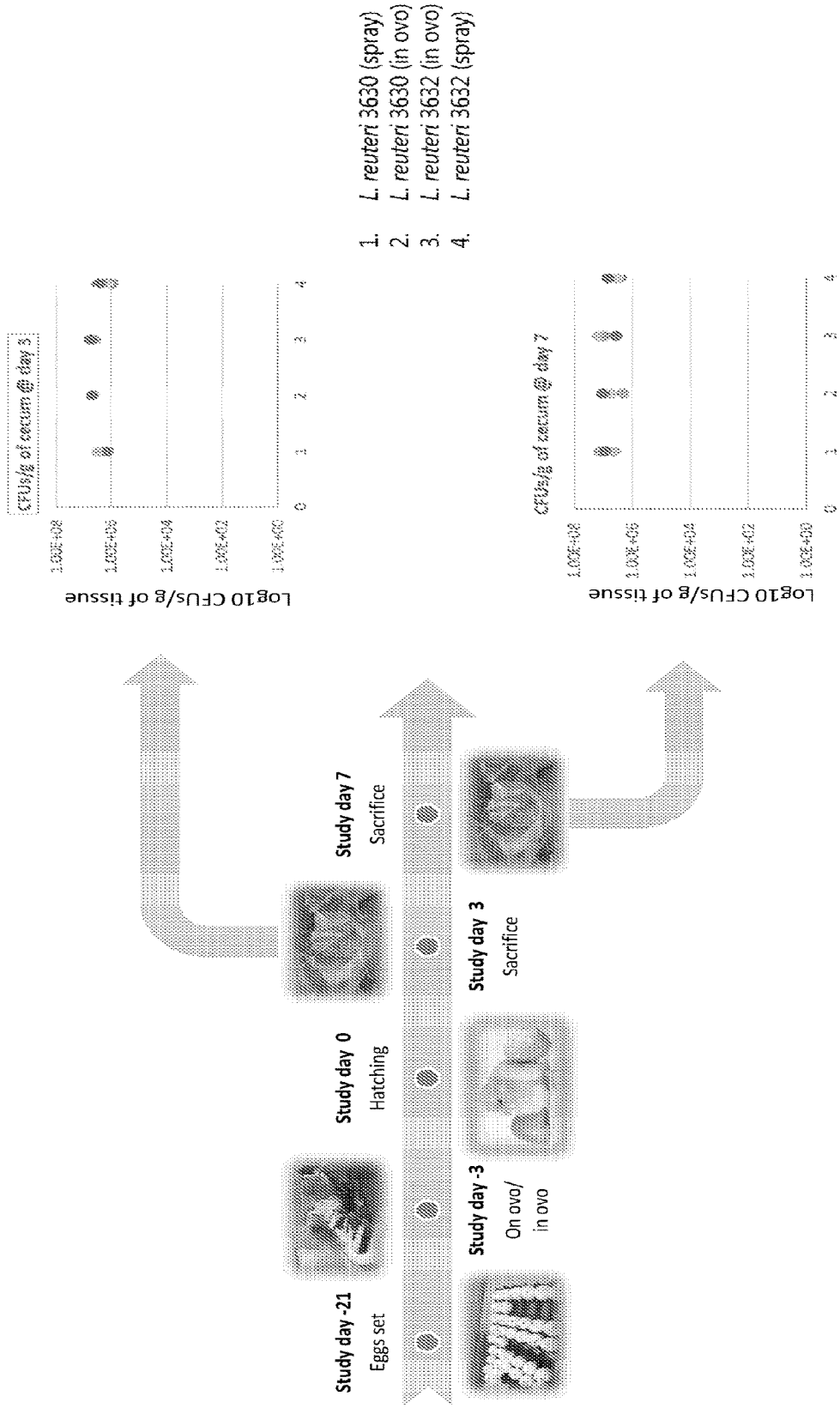
FIG. 7 depicts characterization of *L. reuteri* strain 3630 and 3632 colonization in chicks via on ovo(spray) and in ovo administration route. Left shows the experimental timeline. Right shows CFU of *L. reuteri* strains 3630 and 3632 of chicks sacrificed at 3 days and 7 days.
Figure 8:
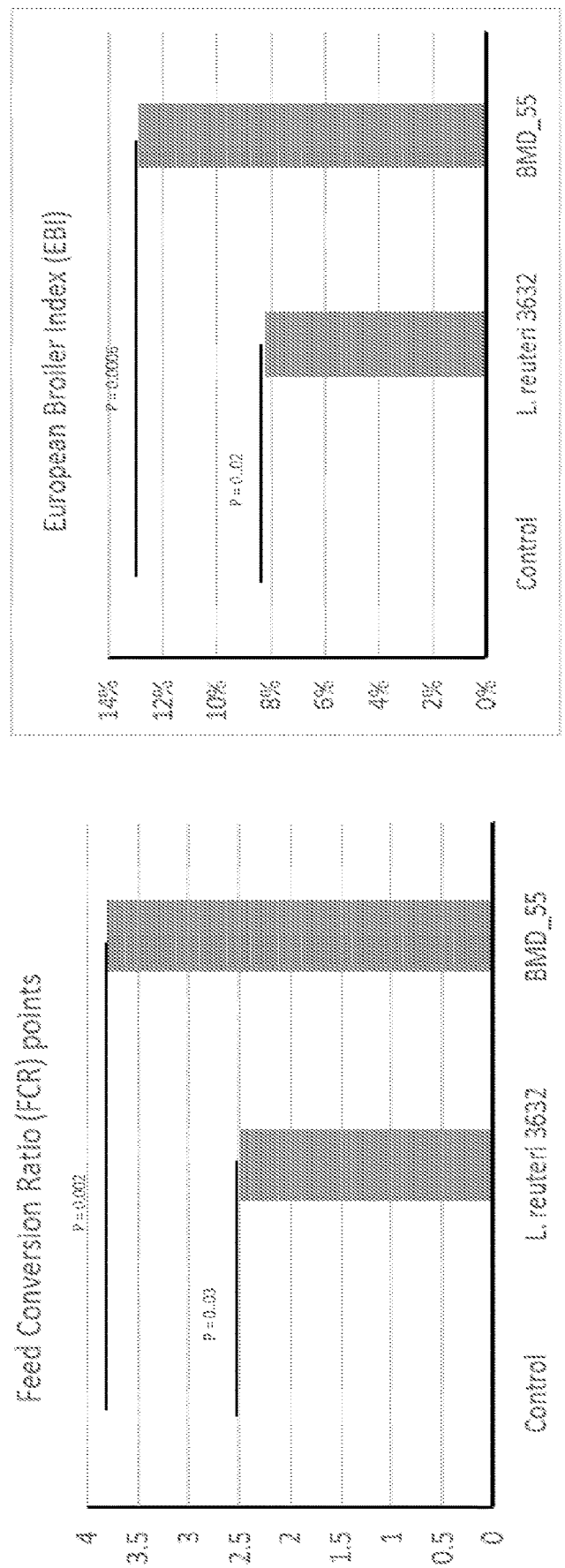
FIG. 8 depicts data from birds vaccinated with coccidiosis vaccine on day 0 and fed with *L. reuteri* in feed from day 0 to day 42 @ 10^7 CFUs/Kg of feed or with BMD_55. Top Feed conversion Ratio (FCR) of chickens administered *L. reuteri* 3632, as compared to chickens administered BMD_55 (bacitracin methylene disalicylate).

Feed conversion ratio and European Broiler index were calculated. Birds that were fed *L. reuteri* demonstrated a reduction in feed conversion ratio and European Broiler index as compared to those fed BMD 55. See FIG. 8.

Example 4. The Effect of Prebiotics on the Growth of *Lactobacillus reuteri*

*L. reuteri* strains 3630 & 3632 were grown individually and in combination, in the presence of several different prebiotics, including fructooligosaccharides (FOS), arabinoxylan oligosaccharides (AXOS), mannan-oligosaccharides (MOS), or galacto-oligosaccharides (GOS).

Figure 10:
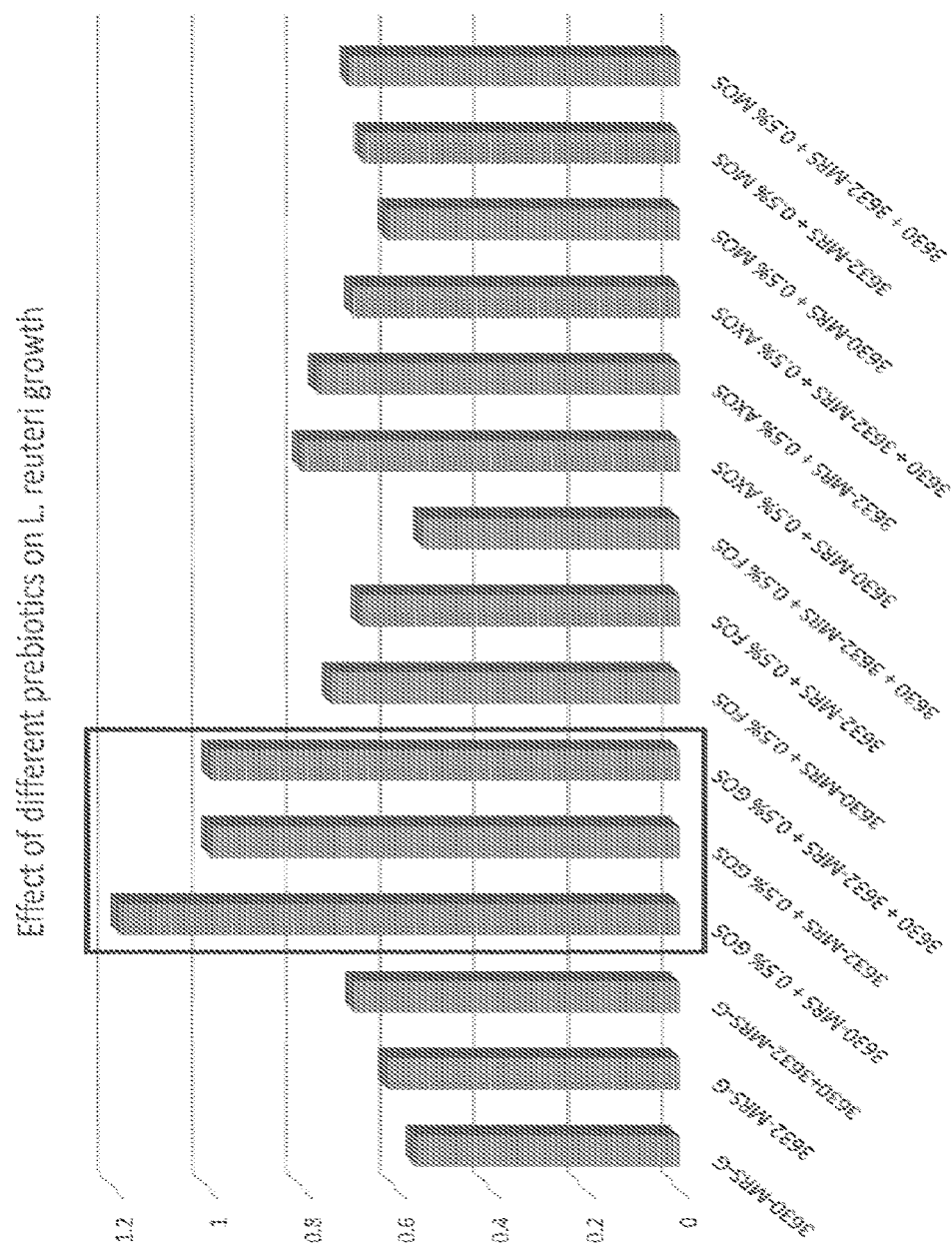
FIG. 10 depicts the effect of prebiotics on the growth of *Lactobacillus reuteri* strains 3630 & 3632. The prebiotics tested include fructooligosaccharides (FOS), arabinoxylan oligosaccharides (AXOS), mannan-oligosaccharides (MOS), or galacto-oligosaccharides (GOS). Increased growth is observed with GOS.
Figure 11A:
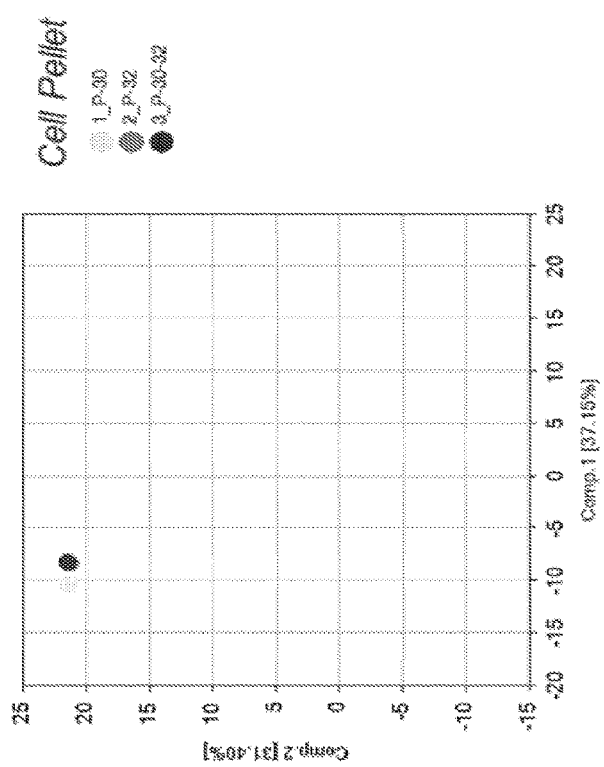
FIGS. 11A-11B depict biochemical metabolic profile of two *Lactobacillus reuteri* strains. The figure represents metabolic data obtained by principal component analysis (PCA) of two strains of *Lactobacillus reuteri* that were cultured individually and together.
Figure 11B:
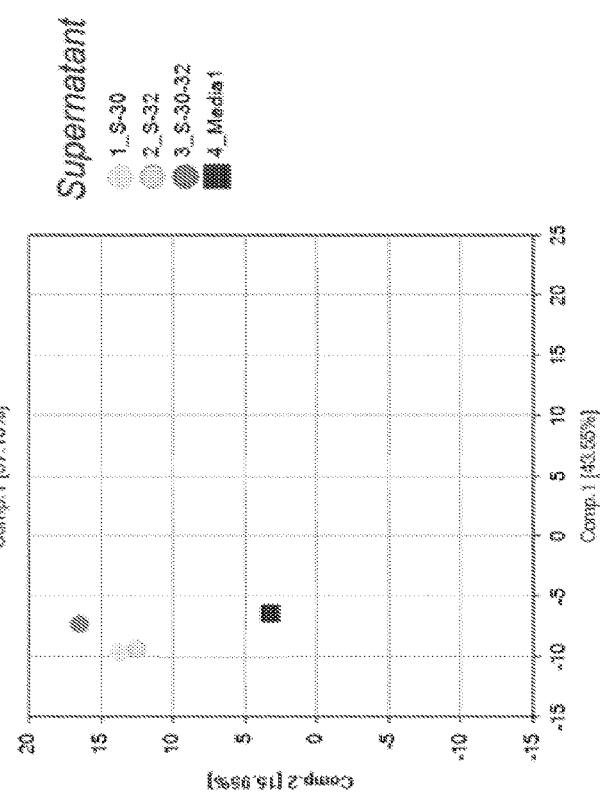

As shown in FIG. 10, strains grown in the presence of GOS demonstrated increased growth as compared to strains grown in the presence of FOS, AXOS, or MOS.

Example 5. In Vivo Effects of *L. reuteri*

An identified strain can effectively function as a direct feed microbial only if the strain is able colonize the host gastrointestinal tract. The ability of *L. reuteri* strains to colonize chickens is assessed following different routes of administration.

*L. reuteri* is administered orally to 10-day old chicks. At various times post inoculation, chicks are sacrificed and the presence of *L. reuteri* is measured in the crop, small intestine, and cecum. Strain 3632 is able to colonize all three tissues and remain detectable for at least 18 days.

*L. reuteri* is administered by in ovo inoculation (i.e. injection into the egg) 3 days before hatching. Strain 3632 is found in the tissues of chicks at 3 and 7 days post hatching, while colonization of a control strain declines after day 3.

*L. reuteri* is administered in ovo by spraying a liquid containing bacteria onto the egg surface. Again, Strains 3630 and 3632 are able to colonize and remain present in chicks 3 and 7 days post hatching. Inoculation by spray is just as efficient as in ovo injection but requires less manipulation of the incubating egg.

Table 2 shows quantifies the effect of *L. reuteri* 3632 treatment on survival. The difference score between strain 3632 and the control is 3.3 and the difference between BMD and control is 2.5. Strain 3632 provides increased survival over BMD treated chics.

TABLE 2

| Treatment conditions | | Difference Score |
|---|---|---|
| Lr_3632 | Ctrl | 3.333333 |
| BMD_55 | Ctrl | 2.5 |

Example 6. Necrotic Enteritis Model

*L. Reuteri* administered in ovo and in drinking water daily @ 10^8 CFU/bird. The birds were orally gavaged with *E. maxima* on day 14. The birds were orally gavaged with *C. perfringes* on day 18, 19, and 20 with 10^8 CFUs/bird.

TABLE 3

Summary of intestinal lesion score, total mortality percent (d15-d28), and necrotic enteritis mortality percent.

| Treatment | No. Cages | Lesion Score Mean (SE) | Total Mortality Percent (SE) | NE Mortality Percent (SE) |
|---|---|---|---|---|
| T1. Unchallenged, untreated | 4 | $0.25^a$ (0.25) | $0.0^a$ (3.4) | $0.0^a$ (2.5) |
| T2. E. maxima alone | 4 | $0.50^a$ (0.25) | $4.2^a$ (3.4) | $0.0^a$ (2.5) |
| T3. E. maxima + C. perfringens | 4 | $0.50^a$ (0.25) | $20.8^b$ (3.4) | $20.8^b$ (2.5) |

TABLE 3-continued

Summary of intestinal lesion score, total mortality percent (d15-d28), and necrotic enteritis mortality percent.

| Treatment | No. Cages | Lesion Score Mean (SE) | Total Mortality Percent (SE) | NE Mortality Percent (SE) |
|---|---|---|---|---|
| T4. *Lactobacillus reuteri* alone (in ovo + oral) | 5 | $0.20^a$ (0.22) | $0.0^a$ (3.0) | $0.0^a$ (2.3) |
| T5. E. maxima + L. reuteri (in ovo + oral) | 5 | $0.20^a$ (0.22) | $3.3^a$ (3.4) | $0.0^a$ (2.3) |
| T6. E. maxima + C. perfringens + L. reuteri (in ovo + oral) | 5 | $0.20^a$ (0.22) | $6.7^{a,b}$ (3.0) | $6.7^a$ (2.3) |
| T7. E. maxima + C. perfringens + L. reuteri (spray + oral) | 1 | $0.0^a$ (0.50) | $16.7^{a,b}$ (6.8) | $16.7^{a,b}$ (5.1) |
| †P-value | | 0.881 | 0.003 | <0.001 |

†Lesion scores and cage-level mortality percentages tested by one-way ANOVA. Within columns, means and percentages with a superscript in common do not differ with a level of significance of 5% over all comparisons.

Example 7. Global Metabolomics Analysis

A global metabolomics analysis of *L. reuteri* strains 3632 and 3630 were conducted. The strains were grown individually and in combination, and various molecules were analyzed in the cell pellet and the supernatant of the cultures. The strains were grown in AOF-MRS media control with no glucose but 0.5% GOS. The molecules in the supernatant represent molecules that are secreted by the cell.

Samples were subject to global untargeted metabolic profiling. Welch t-test and Principal Component Analysis (PCA) were used to analyze the data. Principal component analysis (PCA) is a mathematical procedure that reduces the dimensionality of the data while retaining most of the variation in a dataset. This approach allows visual assessment of the similarities and differences between samples. Populations that differ are expected to group separately and vice versa.

The data is shown in FIGS. 12-19.

Embodiments of the Invention

1. A composition comprising at least one of: an isolated first *Lactobacillus reuteri* strain and an isolated second *Lactobacillus reuteri* strain;
   wherein said composition increases animal health when an effective amount is administered to an animal, as compared to an animal not administered the composition.
2. The composition according to embodiment 1, wherein the first *Lactobacillus reuteri* strain comprises at least one of:
   a nucleic acid sequence having at least 95%, at least 96%, at least 97%, at least 98%, or at least 99% sequence identity with SEQ ID NO:26,
   a nucleic acid sequence having at least 95%, at least 96%, at least 97%, at least 98%, or at least 99% sequence identity with SEQ ID NO: 1,
   a nucleic acid sequence having at least 95%, at least 96%, at least 97%, at least 98%, or at least 99% sequence identity with SEQ ID NO: 3, and
   a nucleic acid that encodes for an amino acid sequence having at least 95%, at least 96%, at least 97%, at least 98%, or at least 99% sequence identity with SEQ ID NO: 8;

wherein the isolated second *Lactobacillus reuteri* strain comprises at least one of:
a nucleic acid sequence having at least 95%, at least 96%, at least 97%, at least 98%, or at least 99% sequence identity with SEQ ID NO:25,
a nucleic acid sequence having at least 95%, at least 96%, at least 97%, at least 98%, or at least 99% sequence identity with SEQ ID NO: 27,
a nucleic acid sequence having at least 95%, at least 96%, at least 97%, at least 98%, or at least 99% sequence identity with SEQ ID NO: 28, and
a nucleic acid sequence having at least 95%, at least 96%, at least 97%, at least 98%, or at least 99% sequence identity with SEQ ID NO: 29.

3. The composition according to any one of embodiments 1-2, wherein the isolated first *Lactobacillus reuteri* strain comprises a nucleic acid sequence having at least 95%, at least 96%, at least 97%, at least 98%, or at least 99% sequence identity with SEQ ID NO: 26.

4. The composition according to any one of embodiments 1-3, wherein the isolated second *Lactobacillus reuteri* strain comprises a nucleic acid sequence having at least 95%, at least 96%, at least 97%, at least 98%, or at least 99% sequence identity with SEQ ID NO: 25.

5. The composition according to any one of embodiments 1-4, wherein the composition comprises an isolated first *Lactobacillus reuteri* strain comprising a nucleic acid sequence having at least 95%, at least 96%, at least 97%, at least 98%, or at least 99% sequence identity with SEQ ID NO: 25; and a nucleic acid sequence having at least 95%, at least 96%, at least 97%, at least 98%, or at least 99% sequence identity with SEQ ID NO: 1, 6. The composition according to any one of embodiments 1-5, wherein the isolated first *Lactobacillus reuteri* strain comprises a nucleic acid sequence having at least 95%, at least 96%, at least 97%, at least 98%, or at least 99% sequence identity with SEQ ID NO:26; and
wherein the isolated second *Lactobacillus reuteri* strain comprises a nucleic acid sequence having at least 95%, at least 96%, at least 97%, at least 98%, or at least 99% sequence identity with SEQ ID NO:25.

7. The composition according to any one of embodiments 1-6, wherein at least one of the first *lactobacillus* strain and a second *lactobacillus* strain secrete at least one of cyclic dipeptides, short chain fatty acids, betaine, dimethylglycine, essential amino acids, nucleotides, myoinositol, and indolin-2-one.

8. The composition according to any one of embodiments 1-7, wherein the composition comprises a ratio of isolated first *Lactobacillus reuteri* strain to isolated second *Lactobacillus reuteri* strain of 0.75-1.5:1.

9. The composition according to any one of embodiments 1-8, wherein the composition comprises about equal amounts of the isolated first *Lactobacillus reuteri* strain and the isolated second *Lactobacillus reuteri* strain.

10. The composition according to any one of embodiments 1-9, wherein the composition is formulated as animal feed, feed additive, food ingredient, water additive, water-mixed additive, consumable solution, consumable spray additive, consumable solid, consumable gel, injection, or combinations thereof 11. The composition according to any one of embodiments 1-10, wherein the composition comprises animal feed.

12. The composition according to embodiment 11, wherein the composition comprises the isolated first *Lactobacillus reuteri* strain in an amount of about $10^2$-$10^8$ CFU/kg of the composition, about $10^4$-$10^7$ CFU/kg of the composition, or about $10^3$-$10^5$ CFU/kg of the composition.

13. The composition according to any one of embodiments 10-12, wherein the composition comprises isolated second *Lactobacillus reuteri* strain in an amount of about $10^2$-$10^8$ CFU/kg of the composition, about $10^4$-$10^7$ CFU/kg of the composition, or about $10^3$-$10^5$ CFU/kg of the composition.

14. The composition according to any one of embodiments 10-13, wherein the composition comprises the isolated first *Lactobacillus reuteri* strain in an amount of about $10^7$ CFU/kg of the composition.

15. The composition according to any one of embodiments 10-14, wherein the composition comprises isolated second *Lactobacillus reuteri* strain in an amount of about $10^7$ CFU/kg of the composition.

16. The composition according to any one of embodiments 1-15, wherein the composition comprises water.

17. The composition according to any one of embodiments 1-16, wherein the animal is bird, poultry, a human, or a non-human mammal.

18. The composition according to any one of embodiments 1-17, wherein the animal is poultry and increases poultry health comprises at least one of: decreasing feed conversion ratio, increasing weight, increasing lean body mass, decreasing pathogen-associated lesion formation in the gastrointestinal tract, decreasing colonization of pathogens, and decreasing mortality rate.

19. The composition according to embodiment 18, wherein increases poultry health comprises decreasing feed conversion ratio by at least 1%, at least 5%, at least 25%, or at least 50%.

20. The composition according to any one of embodiments 17-19, wherein increases poultry health comprises increasing poultry weight by at least 1%, at least 5%, at least 25%, or at least 50%.

21. The composition according to any one of embodiments 17-20, wherein increases poultry health comprises decreasing pathogen-associated lesion formation in the gastrointestinal tract by at least 1%, at least 5%, at least 25%, or at least 50%.

22. The composition according to any one of embodiments 17-21, wherein increases poultry health comprises decreasing mortality rate by at least 1%, at least 5%, at least 25%, or at least 50%.

23. The composition according to any one of embodiments 18-22, wherein the pathogen comprises at least one of *Salmonella, Clostridium, Campylobacter, Staphylococcus, Streptococcus*, and *E. coli* bacterium.

24. The composition according to any one of embodiments 18-23, wherein the pathogen comprises at least one of *Salmonella typhimurium, Salmonella infantis, Salmonella Hadar, Salmonella enteritidis, Salmonella Newport, Salmonella Kentucky, Clostridium perfringens, Staphylococcus aureus, Streptoccus uberis, Streptococcus suis, Escherichia coli, Campylobacter jejuni*, and *Fusobacterium necrophorum*.

25. The composition according to any one of embodiments 17-24, wherein administered comprises in ovo administration.

26. The composition according to any one of embodiments 17-25, wherein administered comprises spray administration.

27. The composition according to any one of embodiments 17-26, wherein the poultry is a chicken.

28. The composition according to any one of embodiments 17-27, wherein the poultry is a broiler chicken.

29. The composition according to any one of embodiments 17-27, wherein the poultry is an egg-producing chicken.
30. The method according to any one of embodiments 1-29, wherein the animal administered the composition, further exhibits at least one improved gut characteristic, as compared to an animal not administered the composition; wherein improved gut characteristics includes:
    increased cyclic dipeptides, increased short chain fatty acids, increased betaine, increased dimethylglycine, increased essential amino acids, increased nucleotides, and increased myo-inositol.
31. The composition according to any one of embodiments 1-30, wherein the animal administered the composition exhibits a shift in the microbiome content of gastrointestinal tract.
32. The method according to embodiment 31, wherein the shift comprises an increase in the amount of Bacteroidaceae bacteria.
33. The composition according to any one of embodiments 1-32, wherein administered comprises administration of a vaccine.
34. The composition according to any one of embodiments 1-33, wherein the animal is poultry and the poultry is administered a vaccine prior to the administration of the composition.
35. The composition according to any one of embodiments 1-34, wherein the animal is poultry and the poultry is administered a vaccine concurrently with the administration.
36. The composition according to any one of embodiments 33-35, wherein the animal is poultry and the poultry is administered a vaccine, wherein said vaccine comprises a vaccine that aids in the prevention of coccidiosis.
37. The composition according to any one of embodiments 1-36, wherein administered comprises administration of galacto-oligosaccharides (GOS).
38. A composition according to any one of embodiments 1-37 for use in therapy.
39. A composition according to any one of embodiments 1-38 for use in improving animal health.
40. A composition according to any one of embodiments 1-39 for use in reducing colonization of an animal by a pathogenic bacterium.
41. A composition according to any one of embodiments 1-40 for use in the manufacture of a medicament for reducing colonization of an animal by a pathogenic bacterium.
42. A method for increasing animal health, the method comprising:
    administering to an animal an effective amount of a composition according to any one of embodiments 1-41.
43. The method according to embodiments 42, wherein the animal is poultry.
44. The method according to any one of embodiments 42-43, wherein increasing animal health includes decreasing pathogen-associated lesion formation in the gastrointestinal tract, decreasing colonization of pathogens, and decreasing mortality rate.
45. A method of treating, ameliorating the effects of, or preventing necrotic enteritis in poultry by administering a composition according to any one of embodiments 1-29 to a poultry in need thereof.

The invention claimed is:

1. A method for increasing animal health, the method comprising administering to an animal an effective amount of a composition comprising at least one *Lactobacillus reuteri* strain selected from:
   (a) an isolated first Lactobacillus reuteri strain comprising a nucleic acid sequence having at least 99% sequence identity with SEQ ID NO:26, and further having a nucleic acid sequence having at least 99% sequence identity with SEQ ID NO: 1, a nucleic acid sequence having at least 99% sequence identity with SEQ ID NO: 3, and a nucleic acid that encodes for an amino acid sequence having at least 99% sequence identity with SEQ ID NO: 8; and
   (b) an isolated second *Lactobacillus reuteri* strain comprising a nucleic acid sequence having at least 99% sequence identity with SEQ ID NO:25, and further having a nucleic acid sequence having at least 99% sequence identity with SEQ ID NO: 27, a nucleic acid sequence having at least 99% sequence identity with SEQ ID NO: 28, and a nucleic acid sequence having at least 99% sequence identity with SEQ ID NO: 29;
   wherein said composition increases animal health when an effective amount is administered to an animal, as compared to an animal not administered the composition.

2. The method according to claim 1, wherein the animal is bird, poultry, a human, or a non-human mammal.

3. A method of treating, ameliorating the effects of, or preventing necrotic enteritis in poultry by administering to a poultry in need thereof a composition comprising at least one *Lactobacillus reuteri* strain selected from:
   (a) an isolated first *Lactobacillus reuteri* strain comprising a nucleic acid sequence having at least 99% sequence identity with SEQ ID NO:26, and further having a nucleic acid sequence having at least 99% sequence identity with SEQ ID NO: 1, a nucleic acid sequence having at least 99% sequence identity with SEQ ID NO: 3, and a nucleic acid that encodes for an amino acid sequence having at least 99% sequence identity with SEQ ID NO: 8; and
   (b) an isolated second *Lactobacillus reuteri* strain comprising a nucleic acid sequence having at least 99% sequence identity with SEQ ID NO:25, and further having a nucleic acid sequence having at least 99% sequence identity with SEQ ID NO: 27, a nucleic acid sequence having at least 99% sequence identity with SEQ ID NO: 28, and a nucleic acid sequence having at least 99% sequence identity with SEQ ID NO: 29.

4. The method according to claim 1, wherein the animal administered the composition further exhibits at least one improved gut characteristic, as compared to an animal not administered the composition; wherein improved gut characteristics includes: increased cyclic dipeptides, increased short chain fatty acids, increased betaine, increased dimethylglycine, increased essential amino acids, increased nucleotides, and increased myo-inositol.

5. The method of claim 1, comprising:
administering to an animal an effective amount of a composition comprising a combination of the isolated first *Lactobacillus reuteri* strain and the isolated second *Lactobacillus reuteri* strain.

6. The method according to claim 5, wherein the animal is bird, poultry, a human, or a non-human mammal.

7. The method of claim 3, comprising administering to a poultry in need thereof a composition comprising a combination of the isolated first *Lactobacillus reuteri* strain and the isolated second *Lactobacillus reuteri*.

8. The method according to claim 7, wherein the poultry administered the composition further exhibits at least one improved gut characteristic, as compared to poultry not administered the composition;
wherein improved gut characteristics includes: increased cyclic dipeptides, increased short chain fatty acids, increased betaine, increased dimethylglycine, increased essential amino acids, increased nucleotides, and increased myo-inositol.

9. The method of claim 3, wherein the composition is formulated as animal feed, feed additive, food ingredient, water additive, water-mixed additive, consumable solution, consumable spray additive, consumable solid, consumable gel, injection, or combinations thereof.

10. The method of claim 3, wherein the composition comprises a combination of the isolated first *Lactobacillus reuteri* strain and the isolated second *Lactobacillus reuteri* strain at a ratio of isolated first *Lactobacillus reuteri* strain to isolated second *Lactobacillus reuteri* strain of 0.75-1.5:1.

11. The method of claim 3, wherein the composition comprises a combination of the isolated first *Lactobacillus reuteri* strain and the isolated second *Lactobacillus reuteri* strain in an amount of about $10^2$-$10^8$ CFU/kg of the composition, about $10^4$-$10^7$ CFU/kg of the composition, or about $10^3$-$10^5$ CFU/kg of the composition.

12. The method of claim 3, wherein the composition is formulated for oral administration, nasal administration, or in ovo administration.

13. The method of claim 3, wherein the composition comprises the isolated first *lactobacillus reuteri* strain and the isolated second *lactobacillus reuteri* strain for in ovo administration in an amount of $10^2$-$10^8$ CFU/embryo.

14. The method of claim 13, wherein the probiotic composition comprises the isolated first *lactobacillus reuteri* strain for in ovo administration in an amount of $10^8$ CFU/embryo and the isolated second *lactobacillus reuteri* strain for in ovo administration in an amount of $10^8$ CFU/embryo.

15. The method of claim 3, wherein the probiotic composition comprises the isolated first *lactobacillus reuteri* strain and the isolated second *lactobacillus reuteri* strain for administration to a poultry bird in an amount of $10^2$-$10^8$ CFU/bird.

16. The method of claim 15, wherein the probiotic composition comprises the isolated first *lactobacillus reuteri* strain for administration in an amount of $10^8$ CFU/bird and the isolated second *lactobacillus reuteri* strain for administration in an amount of $10^8$ CFU/bird.

17. The method of claim 3, wherein the poultry is administered a vaccine, wherein said vaccine comprises a vaccine that aids in the prevention of coccidiosis.

18. The method of claim 1, wherein increasing animal health comprises at least one of decreasing feed conversion ratio, increasing weight, increasing lean body mass, decreasing pathogen-associated lesion formation in the gastrointestinal tract, decreasing colonization by a pathogenic bacterium, and decreasing mortality rate.

19. The method of claim 18, wherein the pathogen comprises at least one of *Salmonella, Clostridium, Campylobacter, Staphylococcus, Streptococcus* and *E. coli* bacterium.

20. The method of claim 19, wherein the pathogen comprises at least one of *Salmonella typhimurium, Salmonella infantis, Salmonella Hadar, Salmonella enteritidis, Salmonella Newport, Salmonella Kentucky, Clostridium perfringens, Staphylococcus aureus, Streptoccus uberis, Streptococcus suis, Escherichia coli* and *Campylobacter jejuni*.

21. The method of claim 1, wherein at least one of the first *Lactobacillus* strain or the second *Lactobacillus* strain secrete at least one of cyclic dipeptides, short chain fatty acids, betaine, dimethylglycine, essential amino acids, nucleotides, myo-inositol, and indolin-2-one.

22. The method of claim 1, wherein the animal is selected from chickens, turkey, dogs, cats, cattle and swine.

23. The method of claim 1, wherein the composition comprises a combination of the isolated first *Lactobacillus reuteri* strain and the isolated second *Lactobacillus reuteri* strain at a ratio of isolated first *Lactobacillus reuteri* strain to isolated second *Lactobacillus reuteri* strain of 0.75-1.5:1.

24. The method of claim 1, wherein the composition comprises a combination of the isolated first *Lactobacillus reuteri* strain and the isolated second *Lactobacillus reuteri* strain in an amount of about $10^2$-$10^8$ CFU/kg of the composition, about $10^4$-$10^7$ CFU/kg of the composition, or about $10^3$-$10^5$ CFU/kg of the composition.

25. The method of claim 1, wherein the composition is formulated as animal feed, feed additive, food ingredient, water additive, water-mixed additive, consumable solution, consumable spray additive, consumable solid, consumable gel, injection, or combinations thereof.

26. The method of claim 1, wherein the composition is formulated for oral administration, nasal administration, or in ovo administration.

27. The method of claim 1, wherein the composition comprises the isolated first *lactobacillus reuteri* strain and the isolated second *lactobacillus reuteri* strain for in ovo administration in an amount of $10^2$-$10^8$ CFU/embryo.

28. The method of claim 27, wherein the probiotic composition comprises the isolated first *lactobacillus reuteri* strain for in ovo administration in an amount of $10^8$ CFU/embryo and the isolated second *lactobacillus reuteri* strain for in ovo administration in an amount of $10^8$ CFU/embryo.

29. The method of claim 1, wherein the probiotic composition comprises the isolated first *lactobacillus reuteri* strain and the isolated second *lactobacillus reuteri* strain for administration to a bird in an amount of $10^2$-$10^8$ CFU/bird.

30. The method of claim 29, wherein the probiotic composition comprises the isolated first *lactobacillus reuteri* strain for administration in an amount of $10^8$ CFU/bird and the isolated second *lactobacillus reuteri* strain for administration in an amount of $10^8$ CFU/bird.

31. The method of claim 1, wherein the animal is poultry and the poultry is administered a vaccine, wherein said vaccine comprises a vaccine that aids in the prevention of coccidiosis.

\* \* \* \* \*

SEQUENCE LISTING

```
<160> NUMBER OF SEQ ID NOS: 43

<210> SEQ ID NO 1
<211> LENGTH: 231
<212> TYPE: DNA
<213> ORGANISM: Artificial Sequence
<220> FEATURE:
<223> OTHER INFORMATION: Based on Lactobacillus reuteri sequence

<400> SEQUENCE: 1
atggacaaag aagaattaga aaaaattgta ggtaataact ttgaggaaat gagtttacaa      60
aaaatgacag aaattcaagg tatgggtgaa taccaagtgg attcaacacc agcagcttct     120
gcgatttcac gggcaacaat tcaagtatca cgtgcatctt ctggaaaatg tctaagttgg     180
ggtagtggtg cagcatttag tgcttatttt actcataaaa gatggtgcta g             231

<210> SEQ ID NO 2
<211> LENGTH: 76
<212> TYPE: PRT
<213> ORGANISM: Artificial Sequence
<220> FEATURE:
<223> OTHER INFORMATION: Based on Lactobacillus reuteri sequence

<400> SEQUENCE: 2

Met Asp Lys Glu Glu Leu Glu Lys Ile Val Gly Asn Asn Phe Glu Glu
1               5                   10                  15

Met Ser Leu Gln Lys Met Thr Glu Ile Gln Gly Met Gly Glu Tyr Gln
            20                  25                  30

Val Asp Ser Thr Pro Ala Ala Ser Ala Ile Ser Arg Ala Thr Ile Gln
        35                  40                  45
```

```
Val Ser Arg Ala Ser Ser Gly Lys Cys Leu Ser Trp Gly Ser Gly Ala
 50                  55                  60

Ala Phe Ser Ala Tyr Phe Thr His Lys Arg Trp Cys
 65                  70                  75

<210> SEQ ID NO 3
<211> LENGTH: 186
<212> TYPE: DNA
<213> ORGANISM: Artificial Sequence
<220> FEATURE:
<223> OTHER INFORMATION: Based on Lactobacillus reuteri sequence

<400> SEQUENCE: 3
atggaagaaa aagaattaga aggtgtaata gggaattcgt ttgaaagtat gactgtagag    60
gaaatgacaa aaattcaagg tatgggtgaa tatcaagtag attcgacgcc tggatatttt   120
atggaaagtg ctgccttttc agctcttaca gccaatataa caagacatgc tatgcatcat   180
cattaa                                                              186

<210> SEQ ID NO 4
<211> LENGTH: 61
<212> TYPE: PRT
<213> ORGANISM: Artificial Sequence
<220> FEATURE:
<223> OTHER INFORMATION: Based on Lactobacillus reuteri sequence

<400> SEQUENCE: 4

Met Glu Glu Lys Glu Leu Glu Gly Val Ile Gly Asn Ser Phe Glu Ser
  1               5                  10                  15

Met Thr Val Glu Glu Met Thr Lys Ile Gln Gly Met Gly Glu Tyr Gln
                 20                  25                  30

Val Asp Ser Thr Pro Gly Tyr Phe Met Glu Ser Ala Ala Phe Ser Ala
             35                  40                  45

Leu Thr Ala Asn Ile Thr Arg His Ala Met His His
         50                  55                  60

<210> SEQ ID NO 5
<211> LENGTH: 373
<212> TYPE: PRT
<213> ORGANISM: Artificial Sequence
<220> FEATURE:
<223> OTHER INFORMATION: Based on Lactobacillus reuteri sequence

<400> SEQUENCE: 5

Met Val Glu Ile Ala His Phe Gly Val Glu Ala Trp Leu Asn Lys Trp
  1               5                  10                  15

Glu Lys Ser Ala Thr Tyr Asp Ile Ser Gln Ser Thr Ile Ala Ser Leu
                 20                  25                  30

Ser Met His Asp Leu Leu Asn Leu Asp Gly Asn Asn Gly Glu Glu Phe
             35                  40                  45

Tyr Glu Met Leu Asp Lys Gln Gln Met Asn Tyr Gly Trp Ile Glu Gly
         50                  55                  60

Ser Pro Glu Phe Lys Glu Glu Val Ala Lys Leu Tyr His His Val Asp
 65                  70                  75                  80

Pro Glu Asn Ile Leu Gln Thr Asn Gly Ala Thr Gly Ala Asn Ile Leu
                 85                  90                  95

Ala Leu Tyr Ala Leu Ile Asn Pro Gly Asp His Val Ile Ala Glu Tyr
                100                 105                 110

Pro Ser Tyr Gln Gln Leu Tyr Asp Ile Pro Lys Ser Leu Gly Ala Asp
```

```
            115                 120                 125
Val Asp Tyr Trp His Ile His Glu Glu Asp Asn Trp Tyr Pro Arg Ile
            130                 135                 140

Asp Asp Leu Lys Ala Met Val Lys Pro Asn Thr Lys Met Ile Cys Leu
145                 150                 155                 160

Asn Asn Ala Asn Asn Pro Thr Gly Thr Val Leu Asp Lys Glu Phe Leu
                165                 170                 175

Glu Gln Val Val Glu Ile Ala Lys Ser Val Asp Ala Tyr Val Leu Val
            180                 185                 190

Asp Glu Val Tyr Leu Pro Leu Asp His Pro Glu Lys Phe Ala Gln Ile
            195                 200                 205

Ile Asp Leu Tyr Asp Lys Gly Ile Ser Thr Asn Ser Leu Ser Lys Thr
210                 215                 220

Tyr Ser Val Pro Gly Val Arg Ile Gly Trp Thr Ala Thr Asn Ala Glu
225                 230                 235                 240

Val Ala Asp Ile Phe Arg Lys Phe Arg Asp Tyr Thr Met Ile Cys Gly
                245                 250                 255

Gly Val Phe Asn Asp Gln Leu Ala Thr Tyr Val Leu Arg His Arg Asp
                260                 265                 270

Gln Val Leu Ala Arg Asn Arg Lys Leu Val Leu Gly Asn Leu Ala Ile
            275                 280                 285

Tyr Lys Asp Trp Ile Asp His Glu Asp Arg Ala Ser Val Ile Met Pro
        290                 295                 300

Gln Ala Val Ser Thr Ser Phe Pro Lys Leu Asp Val Pro Val Asp Ile
305                 310                 315                 320

His Thr Phe Cys Glu Asn Leu Leu His Asp Glu Gly Val Leu Leu Val
                325                 330                 335

Pro Gly Asp Ala Phe Asp Thr Pro Gly His Val Arg Leu Gly Tyr Cys
                340                 345                 350

Ala Pro Glu Ala Thr Leu Lys Glu Gly Leu Lys Arg Leu Ser Lys Tyr
                355                 360                 365

Met His Gln Tyr Asp
        370

<210> SEQ ID NO 6
<211> LENGTH: 178
<212> TYPE: PRT
<213> ORGANISM: Artificial Sequence
<220> FEATURE:
<223> OTHER INFORMATION: Based on Lactobacillus reuteri sequence

<400> SEQUENCE: 6

Met Ile Leu Thr Thr Phe Ile Ile Leu Ile Leu Met Gly Cys Phe Ile
1               5                   10                  15

Asn Gly His Arg Arg Gly Leu Leu Thr Met Thr Leu Met Leu Gly Thr
            20                  25                  30

Tyr Ile Val Ala Trp Ile Val Ala Arg Gln Gly Ala Gln Leu Ile Gly
        35                  40                  45

Gly Trp Leu Lys Ser Leu Leu Pro Ser Ile Gly Thr Pro Ala Thr Phe
    50                  55                  60

Ser Glu Ser Leu Leu Ala Asn Val Asn Ser Asn Leu Phe Phe Tyr Asn
65                  70                  75                  80

Gly Ile Ala Phe Met Ile Ile Phe Thr Ile Val Ser Ile Leu Cys His
                85                  90                  95

Trp Gly Ile Arg Gln Leu Asn Trp Ile Lys Arg Ile Pro Val Val Gly
```

```
                        100                 105                 110
Thr Val Asp Lys Ile Ala Gly Gly Leu Ile Ser Phe Leu Ile Gly Tyr
                115                 120                 125

Leu Ile Ile Tyr Val Val Leu Leu Ile Met Gln Leu Phe Pro Ala Gly
        130                 135                 140

Trp Trp Gln Met Gln Ile Ala Asn Ser Glu Leu Ala Arg Phe Met Ile
145                 150                 155                 160

Asn Gln Thr Pro Gly Ile Ala His Leu Val Ile Asp Thr Leu Val Gln
                165                 170                 175

Gly Gly

<210> SEQ ID NO 7
<211> LENGTH: 332
<212> TYPE: PRT
<213> ORGANISM: Artificial Sequence
<220> FEATURE:
<223> OTHER INFORMATION: Based on Lactobacillus reuteri sequence

<400> SEQUENCE: 7

Met Asn Glu Tyr Asn Ala Glu Met Ala Lys Leu Asn Gln Gly Ala Asn
1               5                   10                  15

Ala Pro Val Ile Thr Thr Asn Ser Val Asn Gln Ala Leu Ser Leu Lys
                20                  25                  30

Pro Glu Asn Asn Ala Thr Val Asp Ile Glu Ala Leu Asn Pro Arg Ile
            35                  40                  45

Thr Phe Lys Arg Val Glu Glu Gly Thr Lys Tyr Ala Gly Tyr Gln Ile
        50                  55                  60

Phe Asp Lys Asn Asn Ala Tyr Val Asn Asn Ile Asp Gly Glu Phe Leu
65                  70                  75                  80

Arg Val Thr Tyr Thr Asn Leu Lys Asn Ser Thr Tyr Lys Gly Ser Lys
                85                  90                  95

Ile Ser Lys Ile Val Val Thr Tyr Ser Asp Ser Thr Pro Thr Gly Asn
            100                 105                 110

Arg Ile Thr Gln Ser Gly Leu Asn Ala Val Thr Glu Gly Ala Asn Asp
        115                 120                 125

Asn Phe Leu Val Val Phe Glu Asp Pro Val Arg Gly Asp Met His Ser
130                 135                 140

Thr Thr Val Thr Ala Thr Tyr Gln Tyr Tyr Asp Ala Asn Gly Asn Leu
145                 150                 155                 160

Ile Asp Phe Ser Gly Thr Asn Asn Ala Trp Leu Ser Val Gly Ser Leu
                165                 170                 175

Asn Phe Asp Gln Gly Asn Asp Tyr Gln Gly Gly Lys Asn Glu Gly Asn
            180                 185                 190

Pro Thr Ser Gly Ile Ser Glu Gly Val Lys Leu Ile Ser Gly Ala Gln
        195                 200                 205

Ile Lys Gln Leu Ala Gly Ser Ser Ile Ser Val His Asp Asp Gly Trp
    210                 215                 220

Ala Tyr Ala Gly Phe Asn Asn Tyr Ser Gly Thr Gly Met Asn Asn Gly
225                 230                 235                 240

Ile Asn Thr Asp Asn Gly Gly Ser Gly Trp Asp Met Asp Gly Ser Pro
                245                 250                 255

Asn Ala Tyr Tyr Gly Ala Ile Val Phe Gln Leu Thr Gly Ser Ser Val
            260                 265                 270

Ser Leu Arg Gln Gly Leu Val Ser Trp Gly Gly Ala Asp Ile Ala Ser
        275                 280                 285
```

Gln Tyr Asn Asn Gln Phe Leu Asn Asn Ala Trp Phe Thr Ala Gly Thr
    290                 295                 300

Thr Leu Pro Glu Thr Gln Ile Lys Gln Pro Ile Arg Lys Thr Ser Glu
305                 310                 315                 320

Thr His Tyr His Tyr Asn Pro Ser Val Ile Arg Leu
                325                 330

<210> SEQ ID NO 8
<211> LENGTH: 2059
<212> TYPE: PRT
<213> ORGANISM: Artificial Sequence
<220> FEATURE:
<223> OTHER INFORMATION: Based on Lactobacillus reuteri sequence

<400> SEQUENCE: 8

Met Ala Gln Lys Leu Met Ser Ala Asn Ser Thr Asp Lys Asn Phe Lys
1               5                   10                  15

Met Tyr Lys Ser Lys Lys Ser Trp Val Phe Ala Tyr Ser Thr Thr Leu
                20                  25                  30

Ala Leu Ala Ala Val Ala Gly Ile Thr Leu Ser Thr Thr Asn Val His
            35                  40                  45

Ala Asp Thr Thr Asn Gly Gly Asp Asn Gln Val Asn Ala Thr Ala Val
        50                  55                  60

Thr Gln Asn Thr Thr Ser Asn Thr Val Asp Gln Ile Ala Ala Asn Thr
65                  70                  75                  80

Ala Gln Thr Asp Asn Thr Ser Thr Ser Ile Asn Ile Arg Ser Leu Met
                85                  90                  95

Asp Asp Leu Ala Ser Gly Asp Asp Thr Ser Ser Ser Gln Asn Gly Gln
            100                 105                 110

Glu Gln Ser Gln Asn Tyr Ala Ser Ser Asn Gln Asn Ser Gln Thr Gln
        115                 120                 125

Gln Glu Asn Gly Thr Thr Gly Gln Ser Thr Ala Ser Gln Asn Gly Thr
    130                 135                 140

Thr Ser Asp Gln Thr Asn Ser Asp Gln Ser Asp Lys Asn Tyr Tyr Val
145                 150                 155                 160

Ile Ser Thr Arg Asp Leu Asp Lys Asn Gly Asn Val Asn Tyr Leu Thr
                165                 170                 175

Gln Lys Asn Tyr Thr Ser Ile Lys Gly Gln Glu Val Ala Asp Gly Thr
            180                 185                 190

Val Val Thr Trp Pro Leu Ser Val Ser Ala Leu Pro Ala Asn Arg Ala
        195                 200                 205

Gln Asp Leu Lys Ser His Val Ile Ser Glu Thr Leu Asp Pro His Leu
    210                 215                 220

Glu Tyr Leu His Tyr Arg Ala Tyr Leu Thr Asn Thr Asp Gly Thr Val
225                 230                 235                 240

Thr Asp Val Thr Asn His Val Asn Leu Asn Arg Ser Gly Gln Thr Leu
                245                 250                 255

Ile Phe Thr Asp Asp Asn Tyr Leu Leu Ser Ile Tyr Asn Asn Asn Arg
            260                 265                 270

Tyr Arg Val Gln Asn Leu Pro Val Ile Lys Leu Val Thr Lys Ala Asn
        275                 280                 285

Gly Asn Gly Tyr Ile Ile Pro Asn Ala Phe Lys Ser Ser Tyr Val Phe
    290                 295                 300

Asn Asp Gly Ser His Asp Val Ser Phe Thr Thr Thr Ser Asn Asn Val
305                 310                 315                 320

```
Gln Ile Lys Thr Phe Asn Pro Gly Asn Ser Lys Asp Val Glu Ile Gly
                325                 330                 335

Gly Asn Val Gln Gly Asp Pro Ser Gly Thr Ile Asn Gly Gln Val Val
            340                 345                 350

Ala Asp Gly Ser Val Val Thr Trp Pro Met Ser Val Gly Asp Leu Pro
        355                 360                 365

Ala Asn Arg Ala Gln Asp Val Leu Ser His Ile Glu Thr Asp Thr Leu
    370                 375                 380

Tyr Asn Gly Leu Asn Tyr Glu Gly Tyr His Ala Tyr Leu Pro Gln Ala
385                 390                 395                 400

Asp Gly Ser Phe Gln Asp Val Ser His Ile Asn Val Gln Gln Asn
            405                 410                 415

Gly Gln Asp Leu Thr Phe Ile Ala Asp Asp Tyr Leu Ile Gly Leu Tyr
        420                 425                 430

Asn Gln Asp Lys Ser Thr Ala Phe Lys Met Pro Ile Ile Asp Leu Ile
    435                 440                 445

Thr Ser Val His Gly Thr Ser Ile Ile Ala Pro Asn Lys Phe Asn Ser
450                 455                 460

Gln Leu Ala Phe Lys Asp Gly Asn Gly Gln Thr Val Ile Asn Asn Thr
465                 470                 475                 480

Ser Asn Gln Val Gln Ile Ser Thr Tyr His Pro Thr Asn Thr Lys Asp
            485                 490                 495

Val Glu Leu Gly Gly Asn Val Gln Gly Asp Thr Pro Asn Ser Ile Asn
            500                 505                 510

Asp Lys Val Val Ala Asn Gly Ala Ile Val Thr Trp Pro Met Ala Ser
            515                 520                 525

Ser Glu Leu Pro Ala Asn Arg Val Gln Asp Leu Gln Ser Arg Val Ile
530                 535                 540

Ser Glu Thr Leu Asp Ser His Leu Gln Tyr Gln Gly Tyr Lys Ala Trp
545                 550                 555                 560

Leu Gln Asn Ala Asp Gly Lys Tyr Thr Asp Val Thr Ser His Val Lys
            565                 570                 575

Leu Thr Gln Asp Gly Gln Asn Leu Thr Phe Ala Asp Asp Glu Tyr Leu
            580                 585                 590

Leu Asn Leu Tyr Asn Ser Asn Lys Gly Thr Ala Tyr Lys Leu Pro Ile
            595                 600                 605

Ile Asp Leu Val Thr Lys Val Asn Gly Ala Gly Ile Thr Ala Pro Asn
        610                 615                 620

Ser Tyr Thr Thr Lys Tyr Val Tyr Ser Asp Gly Asp Gly Asn Thr Thr
625                 630                 635                 640

Ile Asn Val Thr Ser Asn Thr Val Lys Ile Ser Thr Phe Asn Pro Thr
            645                 650                 655

Thr Asn Lys Asp Val Glu Leu Gly Asp Asn Ile His Gly Asp Thr Glu
            660                 665                 670

Ser Ser Ile Ala Gly Lys Leu Val Ser Glu Gly Thr Ile Val Thr Trp
        675                 680                 685

Pro Leu Ser Thr Ser Asp Leu Pro Ala Asn Arg Ala Gln Asp Val Val
        690                 695                 700

Ser His Thr Ala Val Asp Ala Leu Glu Pro Thr Leu Gln Tyr Ile Ser
705                 710                 715                 720

Tyr Thr Ala Trp Leu Pro Asp Ser Asn Gly Gln Leu Gln Asp Val Thr
            725                 730                 735
```

```
Ser His Val Lys Met Thr Arg Asp Gly Gln Lys Leu Thr Phe Thr Asp
             740                 745                 750

Asp Asp Tyr Leu Ile Gly Leu Tyr Asn Gln Asn Lys Asp Ile Ala Leu
         755                 760                 765

Lys Met Pro Ile Ile Asp Leu Val Thr Lys Ala Thr Gly Asn Thr Lys
     770                 775                 780

Leu Leu Pro Asn Ser Phe Asp Ser Gln Phe Val Tyr Asn Asp Val Asp
785                 790                 795                 800

Gly Asn Thr Ile Ile Asn Val Ser Ser Asn Lys Pro Thr Val Glu Thr
                 805                 810                 815

Phe Asp Pro Thr Val His Lys Asp Val Glu Leu Gly Gly Asn Asn Val
             820                 825                 830

Gln Gly Asp Thr Pro Asn Ser Ile Asp Gly Lys Ile Val Ala Gln Gly
         835                 840                 845

Thr Val Val Thr Trp Pro Met Ser Thr Ser Asp Leu Pro Ala Asn Arg
     850                 855                 860

Thr Gln Asp Val Val Ser His Ser Thr Ser Glu Thr Leu Asn Gln Asn
865                 870                 875                 880

Leu Gln Tyr Val Gly Tyr His Ala Tyr Met Pro Asp Ala Asn Gly Lys
                 885                 890                 895

Leu Gln Asp Val Thr Ser His Val Gln Leu Gln Gln Asn Gly Gln Asn
             900                 905                 910

Leu Val Phe Thr Asp Asp Ser Tyr Leu Ile Asn Leu Tyr Asn Gln Asp
         915                 920                 925

Lys Ser Ile Ala Phe Lys Met Pro Ile Ile Asp Leu Met Thr Lys Ala
     930                 935                 940

Ile Ser Asp Ser Ala Thr Ile Pro Asn Thr Phe Glu Ser Gln Tyr Val
945                 950                 955                 960

Phe Asn Asp Gly Asn Gly Asn Thr Thr Phe Lys Ser Thr Ser Asn Thr
                 965                 970                 975

Val Gln Ile Ile Thr Tyr Lys Pro Lys Thr Thr Lys Asp Val Glu Leu
             980                 985                 990

Gly Asp Asn Ile His Gly Asp Thr Asn Ala Ser Ile Ala Gly Gln Met
         995                1000                1005

Ile Thr Asp Gly Thr Val Val Thr Trp Pro Met Ser Thr Ser Asp
    1010                1015                1020

Leu Pro Ala Asn Arg Thr Gln Asp Leu Gln Gln His Val Val Thr
    1025                1030                1035

Asp Asn Leu Asn Asp Asn Leu Ile Phe Gln Gly Tyr Thr Ala Trp
    1040                1045                1050

Leu Pro Thr Ala Asn Gly Leu Val Asp Val Thr Asn His Ile Glu
    1055                1060                1065

Leu Thr Arg Asp Gly Gln Asn Leu Thr Phe Thr Asp Asp Ala Tyr
    1070                1075                1080

Leu Leu Asn Leu Tyr Asn Gln Asn Lys Asp Thr Ala Tyr Lys Leu
    1085                1090                1095

Pro Ile Ile Asp Leu Val Thr Lys Ala Asn Gly Asn Thr Lys Leu
    1100                1105                1110

Ile Pro Asn Asn Phe Asp Ser Met Phe Val Tyr Asn Asp Gly Asp
    1115                1120                1125

Gln Gln Thr Thr Val Asn Val Thr Ser Asn Thr Val Asn Ile Ser
    1130                1135                1140

Thr Tyr Asp Pro Thr Ala Thr Lys Asp Val Glu Leu Gly Asp Asp
```

-continued

```
            1145                1150                1155

Ile Glu Gly Asp Thr Ala Asp Thr Ile Asn Asn Leu Met Val Gln
            1160                1165                1170

Ile Gly Thr Lys Met Thr Tyr Pro Leu Thr Val Ser Asp Leu Pro
            1175                1180                1185

Ala Asn Arg Ala Asp Glu Ile Thr Ala His Gln Ser Val Asp Thr
            1190                1195                1200

Leu Ser Asp Tyr Leu Glu Tyr Gln Gly Tyr Lys Ala Tyr Leu Pro
            1205                1210                1215

Asp Ala Asp Gly Lys Leu Gln Asp Ile Thr Glu His Val Asn Leu
            1220                1225                1230

Lys Arg Glu Gly Gln Lys Leu Ser Phe Asn Asp Asp Tyr Leu
            1235                1240                1245

Ile Asn Leu Tyr Asn Asn Ser Lys Ala Thr Lys Gln Ala Leu Pro
            1250                1255                1260

Val Ile Asp Leu Val Ala Lys Val Thr Gly Ser Asn Asp Gly Lys
            1265                1270                1275

Lys Val His Ile Ile Pro Asn His Phe Asp Ser Thr Ile Thr Thr
            1280                1285                1290

Lys Asp Gly Lys Ile Asn Thr Thr Ser Asn Thr Val Val Ile Asn
            1295                1300                1305

Ser Asn Asp Pro Glu Ala Val Lys Asp Val Glu Leu Gly Asp Asn
            1310                1315                1320

Val Val Gly Asp Thr Pro Asn Ser Val Thr Gly Thr Thr Val Ala
            1325                1330                1335

Asp Gly Thr Ile Val Thr Trp Pro Met Ser Val Gly Ser Leu Gly
            1340                1345                1350

Ala Asn Arg Ala Gln Asn Val Ile Lys His Thr Glu Thr Glu Asn
            1355                1360                1365

Leu Asp Ser Gly Leu Thr Tyr Leu Ser Phe Lys Ala Tyr Leu Pro
            1370                1375                1380

Asp Ala Asp Gly Lys Met Gln Asp Ile Thr Glu His Ile Asn Ile
            1385                1390                1395

Gln Gln Asp Gly Gln Lys Leu Val Phe Thr Asp Asp Tyr Leu
            1400                1405                1410

Ile Ser Leu Tyr Asn Lys Asp Lys Ser Gln Arg Phe Ala Leu Pro
            1415                1420                1425

Val Ile Asp Leu Val Thr Arg Val Asn Gly Asp Asn Lys Ile Ile
            1430                1435                1440

Pro Asn Thr Phe Val Ser Gln Phe Thr Phe Asn Asp Gly Lys Gly
            1445                1450                1455

Asn Thr Ile Thr Ser Val Thr Ser Asn Gln Val Asn Val Ser Thr
            1460                1465                1470

Phe Lys Ser Asn Pro Glu Lys His Val Thr Leu Gly Thr Asp Ile
            1475                1480                1485

Glu Gly Asp Asp Ala Glu Asn Ala Asp Gly Thr Val Val Ala Gln
            1490                1495                1500

Gly Ser Glu Val Thr Trp Pro Leu Ser Asp Lys Ser Pro Leu Pro
            1505                1510                1515

Ala Asn Arg Ser Gln Asp Val Lys Ser His Thr Leu Val Asp Lys
            1520                1525                1530

Leu Asp Asp Asn Leu Gln Tyr Asn Ser Tyr Lys Ala Tyr Leu Lys
            1535                1540                1545
```

```
Gly Thr Asp Gly Lys Leu Gln Asp Val Thr Asp His Ile Lys Leu
1550                1555                1560

Thr Arg Asp Gly Gln Asn Leu Thr Phe Ile Asp Asp Tyr Leu
1565                1570                1575

Leu Asp Leu Tyr Asn Lys Asp Lys Ser Thr Ala Phe Asn Leu Pro
1580                1585                1590

Ile Ile Asp Leu Val Thr Thr Val Val Gly Asn Asp Lys Leu Ile
1595                1600                1605

Pro Asn Lys Phe Asp Ser Asn Phe Val Phe Ser Asp Gly Asn Lys
1610                1615                1620

Asp Thr Ser Met Lys Thr Thr Ser Asn Glu Val Ser Ile Ser Thr
1625                1630                1635

Tyr Thr Pro Val Thr Asn Lys Asp Ala Glu Leu Gly Asp Asn Val
1640                1645                1650

Val Gly Asp Thr Ser Asp Ser Ile Ala Asn Glu Thr Val Pro Asp
1655                1660                1665

Gly Thr Ile Val Thr Trp Pro Leu Ser Val Ser Ser Leu Pro Ala
1670                1675                1680

Asn Arg Ser Gln Asp Val Phe Lys His Val Ile Glu Asp Ile Leu
1685                1690                1695

Asp Gly Asn Leu Thr Tyr Asn Ser Phe Lys Ala Tyr Leu Lys Asp
1700                1705                1710

Ala Ala Gly Asn Leu Gln Glu Val Thr Asp His Val Lys Leu Ala
1715                1720                1725

Gln Glu Gly Gln His Leu Thr Phe Thr Asp Asp Tyr Leu Ile
1730                1735                1740

Asn Leu Tyr Asn Ser Ser Lys Asn Lys Glu Gln Ser Leu Pro Ile
1745                1750                1755

Ile Asp Leu Val Thr Thr Val His Gly Asp Ser Lys Leu Ile Pro
1760                1765                1770

Asn Glu Phe Asp Asn Val Phe Val Phe Lys Asp Gly Lys Gly Gln
1775                1780                1785

Thr Thr Val Lys Thr Thr Ser Asn Lys Val Thr Ile Lys Thr Ala
1790                1795                1800

Ser Leu Pro Thr Pro Thr Lys Glu Glu Thr Asp Asp Gln Gly Asn
1805                1810                1815

Asn Ile Asn Gly Asn Glu Val Lys Ala Gly Glu His Val Asn Tyr
1820                1825                1830

Thr Leu Asn Trp Asp Leu Ser Asn Asp Lys Asp Val Lys Ala Thr
1835                1840                1845

Pro Glu Met Ile Lys Lys Gly Phe Phe Phe Ile Asp Pro Ile Asp
1850                1855                1860

Ser Arg Ala Leu Ser Val Asp Leu Ser Lys Ala Lys Val Val
1865                1870                1875

Asp Gln Asn Gly Asn Lys Val Asp Gly Ile Ser Phe His Leu Tyr
1880                1885                1890

Asn Ser Leu Ser Glu Val Pro Glu Phe Ile Gln Glu Gln Val Lys
1895                1900                1905

Ala Asn Asn Leu Gln Asp Lys Ile Thr Gly Pro Phe Val Val Ala
1910                1915                1920

Gln Ala Asp Asp Leu Gln Ala Phe Phe Asp Lys Tyr Val Lys Thr
1925                1930                1935
```

| | | | | | | | | | | | |
|---|---|---|---|---|---|---|---|---|---|---|---|
|Gly|Ala|Lys|Leu|Lys|Val|Thr|Ile|Pro|Thr|Ile|Val|Lys|Ser|Gly|
| |1940| | | |1945| | | |1950| | | | | |
|Phe|Thr|Gly|Glu|Phe|Ser|Asn|Thr|Ala|Tyr|Gln|Phe|Gly|Phe|Gly|
| |1955| | | |1960| | | |1965| | | | | |
|Lys|Ala|Thr|Pro|Thr|Asn|Thr|Val|Thr|Asn|Tyr|Val|Lys|Pro|Met|
| |1970| | | |1975| | | |1980| | | | | |
|His|Lys|Pro|Ala|Ser|Pro|Glu|Thr|Pro|Ala|Ala|Ile|Ala|Pro|Gln|
| |1985| | | |1990| | | |1995| | | | | |
|Val|Ile|Ser|Ala|Thr|Ala|Gln|Pro|Met|Thr|Ser|Asp|Ala|Pro|Val|
| |2000| | | |2005| | | |2010| | | | | |
|Thr|Pro|Ser|Glu|Lys|Thr|Ala|Lys|Leu|Pro|Gln|Thr|Gly|Asn|Ala|
| |2015| | | |2020| | | |2025| | | | | |
|Asp|Glu|Gly|Ala|Leu|Leu|Gly|Leu|Ala|Ala|Val|Ser|Leu|Val|Gly|
| |2030| | | |2035| | | |2040| | | | | |
|Ser|Leu|Gly|Leu|Ala|Ala|Leu|Gly|Leu|Lys|Gln|Asn|Arg|Asn|Asp|
| |2045| | | |2050| | | |2055| | | | | |
|Asp| | | | | | | | | | | | | | |

<210> SEQ ID NO 9
<211> LENGTH: 300
<212> TYPE: DNA
<213> ORGANISM: Artificial Sequence
<220> FEATURE:
<223> OTHER INFORMATION: Based on Lactobacillus reuteri sequence

<400> SEQUENCE: 9

```
ttaaagtatt aaaatagatg taaaatttat ttttttcaaa agaaatttta attgtacact    60
gttggtattg aacggggtta aacaaaggta aattagcatt tctgcggatt aagataaata   120
gaaaaatgtt aaagaacacc ttaaaaagat taatttttta taattggacc gtatcaattt   180
gtaaaaaggt tgacttttttg aaaaaaaagt ttatcattaa cattgtaaat ttaatgattt   240
acgttatgtt gttatagagc acaggacgta ttgatttata tagaaggagt gtttattaga   300
```

<210> SEQ ID NO 10
<211> LENGTH: 300
<212> TYPE: DNA
<213> ORGANISM: Artificial Sequence
<220> FEATURE:
<223> OTHER INFORMATION: Based on Lactobacillus reuteri sequence

<400> SEQUENCE: 10

```
atgaatggac agatgtttta atcgctagaa tagaaggaaa gaaagtcgca acaaatacgg    60
tttctagtac gtggcaggaa cgactaggta agcagattga cgaattaata gaaaaacatt   120
agtcaaatac atttacaaat gaacagatag ttgatattat atttaagaat tcttcttcag   180
agcctaagat taaagctttc aattggcgaa aagaagttgt acaatatgta taaaggtatg   240
tcagtcaccg aatcagatga tctggcatta tacttgtaaa ttatcaggag gttttcatta   300
```

<210> SEQ ID NO 11
<211> LENGTH: 300
<212> TYPE: DNA
<213> ORGANISM: Artificial Sequence
<220> FEATURE:
<223> OTHER INFORMATION: Based on Lactobacillus reuteri sequence

<400> SEQUENCE: 11

```
atctcacgtg cgatccatta cactaagggc gcgtcaacaa atattatact atcttaaata    60
agaatgaatt gcaagcatta tttgaaaatt ttaattaaaa taacgcttac atcagaaaaa   120
```

-continued

```
tgttgtgatt gaatagacaa ttttttttgaa gatggtatca taagtatcgt aggagttgta    180
ttattgctta gaccttacca ctgcgtcact tacaatggtt gagagttgcg atgctgatgt    240
aatgtgataa actaagcaag tacactaatt atgttttttc ctaaaggagg aatttgcagt    300
```

<210> SEQ ID NO 12
<211> LENGTH: 300
<212> TYPE: DNA
<213> ORGANISM: Artificial Sequence
<220> FEATURE:
<223> OTHER INFORMATION: Based on Lactobacillus reuteri sequence

<400> SEQUENCE: 12

```
ttgtttaaga tatcttcaa agctgcggaa ttttccag cttttttagt tagttttgtt      60
ttcataagct ataattttaa ccgattccaa atttctttta aaagtttttt tgatctagac   120
cattaattga taaacgctta ccaaagacta atcaacaagc catttagcgg tagtggtcca   180
ttttaacttt ctaagacatc ttctcagaaa acgtttcctt tgatagtgca gattgtgctt   240
taagagtata taattgtcac ggtataagaa ttttctgaaa tttcagaagg agtgaacatt   300
```

<210> SEQ ID NO 13
<211> LENGTH: 449
<212> TYPE: DNA
<213> ORGANISM: Artificial Sequence
<220> FEATURE:
<223> OTHER INFORMATION: Based on Lactobacillus reuteri sequence

<400> SEQUENCE: 13

```
ctcctctatt attattcctg atcaatttta aattaatctc cctagatagg tatattttag     60
cacaggtcac caacgttcca aagtttaatc tatgtttaaa cttaattttt caaaaaatg    120 ctatactatg ttcacgatac tttaaggaaa ggtgattaca atagtgagtc tcttaattgc   180
tattcttatc tgctggttgc tatggaagat tgggggttta acggttaagt tcattggtct   240
aatccttctt attctattaa tcgggacatt aattcatgtt ttactttggc cagcgatcct   300
tttagcagtt attatcttag gagcaggttt attcactaac taattatct ataaaatctt   360 atagtaattt ttctgcggaa tgttataatc attactgtga gagaaatctc aaataatgta   420
tacataagat gaaagggaga ctgttttatt                                    449
```

<210> SEQ ID NO 14
<211> LENGTH: 250
<212> TYPE: DNA
<213> ORGANISM: Artificial Sequence
<220> FEATURE:
<223> OTHER INFORMATION: Based on Lactobacillus reuteri sequence

<400> SEQUENCE: 14

```
acaaatacgg tttctagtac gtggcaggaa cgactaggta agcagattga cgaattaata    60
gaaaaacatt agtcaaatac atttacaaat gaacagatag ttgatattat atttaagaat   120
tcttcttcag agcctaagat taaagctttc aattggcgaa aagaagttgt acaatatgta   180
taaaggtatg tcagtcaccg aatcagatga tctggcatta tacttgtaaa ttatcaggag   240
gttttcatta                                                          250
```

<210> SEQ ID NO 15
<211> LENGTH: 3017
<212> TYPE: PRT
<213> ORGANISM: Artificial Sequence
<220> FEATURE:

<223> OTHER INFORMATION: Based on Lactobacillus reuteri sequence

<400> SEQUENCE: 15

Met Val Ser Lys Asn Asn His Gln Phe Tyr Gln Gln Lys His Ala Glu
1               5                   10                  15

Arg Lys Gln Arg Trp Gly Ile Arg Lys Leu Ser Val Gly Val Ala Ser
            20                  25                  30

Val Leu Leu Gly Thr Thr Phe Met Leu Tyr Gly Asn His Ala Val Leu
        35                  40                  45

Ala Asp Thr Val Thr Ser Pro Ser Asp Val Thr Arg Ser Thr Thr
    50                  55                  60

Thr Gln Gly Gly Asn Lys Asp Lys Val Thr Glu Gly Thr Thr Glu Gly
65                  70                  75                  80

Thr Thr Ser Thr Pro Gln Thr Ser Gly Asp Ser Thr Asp Lys Gln Ala
                85                  90                  95

Asn Gly Gln Asn Val Asn Gln Gln Val Pro Thr Thr Asp Thr Glu Glu
            100                 105                 110

Ala Thr Asn His Gln Asp Thr Pro Gln Gly Gln Asp Thr Thr Gln Asn
        115                 120                 125

Thr Thr Asn Val Asp Lys Asp Thr Glu Val Thr Pro Ala Asn Asp
130                 135                 140

Ala Thr Pro Thr Thr Gln Lys Ile Thr Ala Lys Phe Thr Thr Ala
145                 150                 155                 160

Lys Phe Thr Thr Ala Lys Phe Thr Ala Ala Lys Phe Lys Val Leu Ala
                165                 170                 175

Ala Arg Pro Val Met Lys Val Ala Gly Thr Ala Ser Leu Pro Ile Ser
            180                 185                 190

Asn Gln Asp Ile Lys Leu Asp Ser Gln Pro Met Leu Thr Glu Ile Ile
        195                 200                 205

Asn Lys Pro Thr Asp Asn Trp Val Tyr Asn Asn Leu Lys Trp Tyr Gln
    210                 215                 220

Asp Thr Ser Thr Glu Lys Ile Lys Glu Ile Leu Gln Asn His Thr Ala
225                 230                 235                 240

Asn Asp Glu Ser Gly Arg Tyr Tyr Phe Ala Gly Val Ala Asn Tyr Asn
                245                 250                 255

Glu His Tyr His Ala Ile Tyr Leu Leu Ala Arg Ser Asn Asn Leu Asn
            260                 265                 270

Asp Asn Ser Leu Tyr Val Thr Ile Leu His Thr Gly Leu Gly Lys Asn
        275                 280                 285

Ile Gln Glu Ala Val Val Ala Pro Gly Glu Ser Lys Val Glu Tyr
    290                 295                 300

Ser Gly Thr Thr His Thr Pro Ile Phe Thr Asn Tyr Asp Gly Thr Ser
305                 310                 315                 320

Ala Ser Ile Asp Leu Asp Gly Ile Glu Lys Gly Asp Asn Ile Tyr Gly
                325                 330                 335

Met Val Val Gly Phe Ala Tyr Gly His Asn Thr Gly Ile Lys Gly Asp
            340                 345                 350

Pro Ala Ser Met Gly Asn Gly Phe Val Met Thr Pro Ile Pro Thr Lys
        355                 360                 365

Met Thr Thr Thr Ile His Tyr Ile Asp Gln Ala Thr Gly Asp Glu Ile
    370                 375                 380

Ala Val Pro Lys Ser Phe Glu Gly Val Ala Tyr Gln Lys Tyr Thr Ile
385                 390                 395                 400

```
Thr Gly Glu Ala Pro Thr Ile Asp Gly Tyr Thr Leu Lys Lys Ser Pro
                405                 410                 415
Glu Thr Thr Gly Tyr Ile Ser Pro Tyr Lys Val Gly Glu Ser Tyr Asp
            420                 425                 430
Phe Arg Leu Asp Lys His Val Ile Lys Gln Thr Val Ile Asp Ala
        435                 440                 445
Gln Gly Leu Val Arg Val Thr Ala Tyr Tyr Asp Gly Glu Val Leu Asn
    450                 455                 460
Asn Thr Thr Arg Tyr Leu Gly Asn Lys Leu Asn Val Asn Asp Arg Met
465                 470                 475                 480
Ser Phe Ile Ser His Gly Lys Trp Tyr Thr Tyr Ile Asn Gln Ile Thr
                485                 490                 495
Ser Thr Asn Asp Gly Ile Val Tyr Tyr Ala Lys Asp Gly Ser Glu
            500                 505                 510
Asp Lys Ser Glu Val Arg Val His Tyr Ile Asp Val Thr Gly Ser Lys
        515                 520                 525
Asn Ser Ile Phe Val Pro Gly Asp Gly Glu Val Ala Thr Asp Lys
    530                 535                 540
Ile Ser Gly Lys Leu Gly Glu Asn Tyr Asn Tyr Asp Val Asn Leu Pro
545                 550                 555                 560
Thr Asp Tyr Asn Leu Ala Thr Asn Gln Ala Asn Thr Val Asn Gly Thr
                565                 570                 575
Tyr Thr Ile Asp His His Asp Glu Tyr Val Tyr Val Lys Lys Thr
            580                 585                 590
Ser Ala Glu Leu Asp Pro Thr Val Pro Ala Lys Thr Lys Val Asp Asn
        595                 600                 605
Pro Thr Ser Leu Thr Ala Asp Glu Lys Lys Thr Ile Glu Asp Lys Ile
    610                 615                 620
Val Glu Ala Asn Lys Asp Lys Phe Pro Glu Gly Thr Gly Val Thr Val
625                 630                 635                 640
Ala Asn Asp Gly Lys Ala Thr Ile Thr Tyr Pro Asp Lys Ser Val Asp
                645                 650                 655
Thr Ile Glu Gly Asn Gln Leu Val Glu Glu Lys Thr Ser Ala Glu Lys
            660                 665                 670
Leu Asp Pro Thr Val Pro Ala Lys Thr Lys Val Asp Asn Pro Thr Ser
        675                 680                 685
Leu Thr Ala Asp Glu Lys Lys Thr Ile Glu Asp Lys Ile Val Glu Ala
    690                 695                 700
Asn Lys Asp Lys Phe Pro Glu Gly Thr Gly Val Thr Val Ala Asn Asp
705                 710                 715                 720
Gly Lys Ala Thr Ile Thr Tyr Pro Asp Lys Ser Val Asp Thr Ile Glu
                725                 730                 735
Gly Asn Gln Leu Val Glu Glu Lys Thr Ser Ala Glu Lys Leu Asp Pro
            740                 745                 750
Thr Val Pro Ala Lys Thr Lys Val Asp Asn Pro Thr Ser Leu Thr Ala
        755                 760                 765
Asp Glu Lys Lys Thr Ile Glu Asp Lys Ile Val Glu Ala Asn Lys Asp
    770                 775                 780
Lys Phe Pro Glu Gly Thr Gly Val Thr Val Ala Asn Asp Gly Lys Ala
785                 790                 795                 800
Thr Ile Thr Tyr Pro Asp Lys Ser Val Asp Thr Ile Glu Gly Asn Gln
                805                 810                 815
Leu Val Glu Glu Lys Thr Ser Ala Glu Lys Leu Asp Pro Thr Val Pro
```

```
                820                 825                 830
Ala Lys Thr Lys Val Asp Asn Pro Thr Ser Leu Thr Ala Asp Glu Lys
            835                 840                 845
Lys Thr Ile Glu Asp Lys Ile Val Glu Ala Asn Lys Asp Lys Phe Pro
            850                 855                 860
Glu Gly Thr Gly Val Thr Val Ala Asn Asp Gly Lys Ala Thr Ile Thr
865                 870                 875                 880
Tyr Pro Asp Lys Ser Val Asp Thr Ile Glu Gly Asn Gln Leu Val Glu
            885                 890                 895
Glu Lys Thr Ser Ala Glu Lys Leu Asp Pro Thr Val Pro Ala Lys Thr
            900                 905                 910
Lys Val Asp Asn Pro Thr Ser Leu Thr Ala Asp Glu Lys Lys Thr Ile
            915                 920                 925
Glu Asp Lys Ile Val Glu Ala Asn Lys Asp Lys Phe Pro Glu Gly Thr
            930                 935                 940
Gly Val Thr Val Ala Asn Asp Gly Lys Ala Thr Ile Thr Tyr Pro Asp
945                 950                 955                 960
Lys Ser Val Asp Thr Ile Glu Gly Asn Gln Leu Val Glu Glu Lys Thr
            965                 970                 975
Ser Ala Glu Lys Leu Asp Pro Thr Val Pro Ala Lys Thr Lys Val Asp
            980                 985                 990
Asn Pro Thr Ser Leu Thr Ala Asp Glu Lys Lys Thr Ile Glu Asp Lys
            995                1000                1005
Ile Val Glu Ala Asn Lys Asp Lys Phe Pro Glu Gly Thr Gly Val
           1010                1015                1020
Thr Val Ala Asn Asp Gly Lys Ala Thr Ile Thr Tyr Pro Asp Lys
           1025                1030                1035
Ser Val Asp Thr Ile Glu Gly Asn Gln Leu Val Glu Glu Lys Thr
           1040                1045                1050
Ser Ala Glu Lys Leu Asp Pro Thr Val Pro Ala Lys Thr Lys Val
           1055                1060                1065
Asp Asn Pro Thr Ser Leu Thr Ala Asp Glu Lys Lys Thr Ile Glu
           1070                1075                1080
Asp Lys Ile Val Glu Ala Asn Lys Asp Lys Phe Pro Glu Gly Thr
           1085                1090                1095
Gly Val Thr Val Ala Asn Asp Gly Lys Ala Thr Ile Thr Tyr Pro
           1100                1105                1110
Asp Lys Ser Val Asp Thr Ile Glu Gly Asn Gln Leu Val Glu Glu
           1115                1120                1125
Lys Thr Ser Ala Glu Lys Leu Asp Pro Thr Val Pro Ala Lys Thr
           1130                1135                1140
Lys Val Asp Asn Pro Thr Ser Leu Thr Ala Asp Glu Lys Lys Thr
           1145                1150                1155
Ile Glu Asp Lys Ile Val Glu Ala Asn Lys Asp Lys Phe Pro Glu
           1160                1165                1170
Gly Thr Gly Val Thr Val Ala Asn Asp Gly Lys Ala Thr Ile Thr
           1175                1180                1185
Tyr Pro Asp Lys Ser Val Asp Thr Ile Glu Gly Asn Gln Leu Val
           1190                1195                1200
Glu Glu Lys Thr Ser Ala Glu Lys Leu Asp Pro Thr Val Pro Ala
           1205                1210                1215
Lys Thr Lys Val Asp Asn Pro Thr Ser Leu Thr Ala Asp Glu Lys
           1220                1225                1230
```

-continued

```
Lys Thr Ile Glu Asp Lys Ile Val Glu Ala Asn Lys Asp Lys Phe
1235                1240                1245

Pro Glu Gly Thr Gly Val Thr Val Ala Asn Asp Gly Lys Ala Thr
1250                1255                1260

Ile Thr Tyr Pro Asp Lys Ser Val Asp Thr Ile Glu Gly Asn Gln
1265                1270                1275

Leu Val Glu Glu Lys Thr Ser Ala Glu Lys Leu Asp Pro Thr Val
1280                1285                1290

Pro Ala Lys Thr Lys Val Asp Asn Pro Thr Ser Leu Thr Ala Asp
1295                1300                1305

Glu Lys Lys Thr Ile Glu Asp Lys Ile Val Glu Ala Asn Lys Asp
1310                1315                1320

Lys Phe Pro Glu Gly Thr Gly Val Thr Val Ala Asn Asp Gly Lys
1325                1330                1335

Ala Thr Ile Thr Tyr Pro Asp Lys Ser Val Asp Thr Ile Glu Gly
1340                1345                1350

Asn Gln Leu Val Glu Glu Lys Thr Ser Ala Glu Lys Leu Asp Pro
1355                1360                1365

Thr Val Pro Ala Lys Thr Lys Val Asp Asn Pro Thr Ser Leu Thr
1370                1375                1380

Ala Asp Glu Lys Lys Thr Ile Glu Asp Lys Ile Val Glu Ala Asn
1385                1390                1395

Lys Asp Lys Phe Pro Glu Gly Thr Gly Val Thr Val Ala Asn Asp
1400                1405                1410

Gly Lys Ala Thr Ile Thr Tyr Pro Asp Lys Ser Val Asp Thr Ile
1415                1420                1425

Glu Gly Asn Gln Leu Val Glu Glu Lys Thr Ser Ala Glu Lys Leu
1430                1435                1440

Asp Pro Thr Val Pro Ala Lys Thr Lys Val Asp Asn Pro Thr Ser
1445                1450                1455

Leu Thr Ala Asp Glu Lys Lys Thr Ile Glu Asp Lys Ile Val Glu
1460                1465                1470

Ala Asn Lys Asp Lys Phe Pro Glu Gly Thr Gly Val Thr Val Ala
1475                1480                1485

Asn Asp Gly Lys Ala Thr Ile Thr Tyr Pro Asp Lys Ser Val Asp
1490                1495                1500

Thr Ile Glu Gly Asn Gln Leu Val Glu Glu Lys Thr Ser Ala Glu
1505                1510                1515

Lys Leu Asp Pro Thr Val Pro Ala Lys Thr Lys Val Asp Asn Pro
1520                1525                1530

Thr Ser Leu Thr Ala Asp Glu Lys Lys Thr Ile Glu Asp Lys Ile
1535                1540                1545

Val Glu Ala Asn Lys Asp Lys Phe Pro Glu Gly Thr Gly Val Thr
1550                1555                1560

Val Ala Asn Asp Gly Lys Ala Thr Ile Thr Tyr Pro Asp Lys Ser
1565                1570                1575

Val Asp Thr Ile Glu Gly Asn Gln Leu Val Glu Glu Lys Thr Ser
1580                1585                1590

Ala Glu Lys Leu Asp Pro Thr Val Pro Ala Lys Thr Lys Val Asp
1595                1600                1605

Asn Pro Thr Ser Leu Thr Ala Asp Glu Lys Lys Thr Ile Glu Asp
1610                1615                1620
```

-continued

```
Lys Ile Val Glu Ala Asn Lys Asp Lys Phe Pro Glu Gly Thr Gly
    1625                1630                1635

Val Thr Val Ala Asn Asp Gly Lys Ala Thr Ile Thr Tyr Pro Asp
    1640                1645                1650

Lys Ser Val Asp Thr Ile Glu Gly Asn Gln Leu Val Glu Glu Lys
    1655                1660                1665

Thr Ser Ala Glu Lys Leu Asp Pro Thr Val Pro Ala Lys Thr Lys
    1670                1675                1680

Val Asp Asn Pro Thr Ser Leu Thr Ala Asp Glu Lys Lys Thr Ile
    1685                1690                1695

Glu Asp Lys Ile Val Glu Ala Asn Lys Asp Lys Phe Pro Glu Gly
    1700                1705                1710

Thr Gly Val Thr Val Ala Asn Asp Gly Lys Ala Thr Ile Thr Tyr
    1715                1720                1725

Pro Asp Lys Ser Val Asp Thr Ile Glu Gly Asn Gln Leu Val Glu
    1730                1735                1740

Glu Lys Thr Ser Ala Glu Lys Leu Asp Pro Thr Val Pro Ala Lys
    1745                1750                1755

Thr Lys Val Asp Asn Pro Thr Ser Leu Thr Ala Asp Glu Lys Lys
    1760                1765                1770

Thr Ile Glu Asp Lys Ile Val Glu Ala Asn Lys Asp Lys Phe Pro
    1775                1780                1785

Glu Gly Thr Gly Val Thr Val Ala Asn Asp Gly Lys Ala Thr Ile
    1790                1795                1800

Thr Tyr Pro Asp Lys Ser Val Asp Thr Ile Glu Gly Asn Gln Leu
    1805                1810                1815

Val Glu Glu Lys Thr Ser Ala Glu Lys Leu Asp Pro Thr Val Pro
    1820                1825                1830

Ala Lys Thr Lys Val Asp Asn Pro Thr Ser Leu Thr Ala Asp Glu
    1835                1840                1845

Lys Lys Thr Ile Glu Asp Lys Ile Val Glu Ala Asn Lys Asp Lys
    1850                1855                1860

Phe Pro Glu Gly Thr Gly Val Thr Val Ala Asn Asp Gly Lys Ala
    1865                1870                1875

Thr Ile Thr Tyr Pro Asp Lys Ser Val Asp Thr Ile Glu Gly Asn
    1880                1885                1890

Gln Leu Val Glu Glu Lys Thr Ser Ala Glu Lys Leu Asp Pro Thr
    1895                1900                1905

Val Pro Ala Lys Thr Lys Val Asp Asn Pro Thr Ser Leu Thr Ala
    1910                1915                1920

Asp Glu Lys Lys Thr Ile Glu Asp Lys Ile Val Glu Ala Asn Lys
    1925                1930                1935

Asp Lys Phe Pro Glu Gly Thr Gly Val Thr Val Ala Asn Asp Gly
    1940                1945                1950

Lys Ala Thr Ile Thr Tyr Pro Asp Lys Ser Val Asp Thr Ile Glu
    1955                1960                1965

Gly Asn Gln Leu Val Glu Glu Lys Thr Ser Ala Glu Lys Leu Asp
    1970                1975                1980

Pro Thr Val Pro Ala Lys Thr Lys Val Asp Asn Pro Thr Ser Leu
    1985                1990                1995

Thr Ala Asp Glu Lys Lys Thr Ile Glu Asp Lys Ile Val Glu Ala
    2000                2005                2010

Asn Lys Asp Lys Phe Pro Glu Gly Thr Gly Val Thr Val Ala Asn
```

```
                    2015                2020                2025

Asp Gly Lys Ala Thr Ile Thr Tyr Pro Asp Lys Ser Val Asp Thr
    2030                2035                2040

Ile Glu Gly Asn Gln Leu Val Glu Glu Lys Thr Ser Ala Glu Lys
    2045                2050                2055

Leu Asp Pro Thr Val Pro Ala Lys Thr Lys Val Asp Asn Pro Thr
    2060                2065                2070

Ser Leu Thr Ala Asp Glu Lys Lys Thr Ile Glu Asp Lys Ile Val
    2075                2080                2085

Glu Ala Asn Lys Asp Lys Phe Pro Glu Gly Thr Gly Val Thr Val
    2090                2095                2100

Ala Asn Asp Gly Lys Ala Thr Ile Thr Tyr Pro Asp Lys Ser Val
    2105                2110                2115

Asp Thr Ile Glu Gly Asn Gln Leu Val Glu Glu Lys Thr Ser Ala
    2120                2125                2130

Glu Lys Leu Asp Pro Thr Val Pro Ala Lys Thr Lys Val Asp Asn
    2135                2140                2145

Pro Thr Ser Leu Thr Ala Asp Glu Lys Lys Thr Ile Glu Asp Lys
    2150                2155                2160

Ile Val Glu Ala Asn Lys Asp Lys Phe Pro Glu Gly Thr Gly Val
    2165                2170                2175

Thr Val Ala Asn Asp Gly Lys Ala Thr Ile Thr Tyr Pro Asp Lys
    2180                2185                2190

Ser Val Asp Thr Ile Glu Gly Asn Gln Leu Val Glu Glu Lys Thr
    2195                2200                2205

Ser Ala Glu Lys Leu Asp Pro Thr Val Pro Ala Lys Thr Lys Val
    2210                2215                2220

Asp Asp Pro Thr Lys Leu Thr Asn Asp Glu Lys Lys Glu Val Glu
    2225                2230                2235

Asp Asn Ile Arg Asp His Asn Thr Gly Leu Pro Glu Gly Thr Lys
    2240                2245                2250

Ile Ala Val Gly Asp Asn Gly Asp Thr Thr Ile Thr Tyr Pro Asp
    2255                2260                2265

Lys Ser Val Asp Thr Ile Glu Gly Asn Gln Leu Val Glu Glu Lys
    2270                2275                2280

Thr Ser Ala Glu Lys Leu Asp Pro Thr Val Pro Ala Lys Thr Lys
    2285                2290                2295

Val Asp Asp Pro Thr Lys Leu Thr Asn Asp Glu Lys Lys Glu Val
    2300                2305                2310

Glu Asp Asn Ile Arg Asp His Asn Thr Gly Leu Pro Glu Gly Thr
    2315                2320                2325

Lys Ile Ala Val Gly Asp Asn Gly Asp Thr Thr Ile Thr Tyr Pro
    2330                2335                2340

Asp Asn Ser Val Asp Thr Ile Pro Gly Asp Lys Val Val Glu Gly
    2345                2350                2355

Lys Ser Asp Ala Ala Lys Asn Glu Pro Lys Val Pro Gly Asp Lys
    2360                2365                2370

Val Lys Val Asp Asp Pro Asn Lys Leu Thr Glu Asp Glu Lys Ser
    2375                2380                2385

Glu Val Val Lys Ala Val Glu Asp Ala Asn Lys Asp Glu Asn Gly
    2390                2395                2400

Lys Ser Thr Leu Pro Glu Gly Ser Lys Val Thr Val Gly Asp Asn
    2405                2410                2415
```

-continued

```
Gly Asp Val Thr Val Thr Tyr Pro Asp Gly Ser Lys Asp Thr Ile
2420                2425                2430

Pro Gly Asp Lys Val Val Glu Gly Lys Gly Thr Glu Gly Gln Thr
2435                2440                2445

Asp Ala Asp Lys Asn Glu Pro Lys Val Pro Gly Asp Lys Val Lys
2450                2455                2460

Val Asp Asp Pro Asn Lys Leu Thr Glu Asp Glu Lys Ser Glu Val
2465                2470                2475

Val Lys Ala Val Glu Asp Ala Asn Lys Asp Glu Asn Gly Lys Ser
2480                2485                2490

Thr Leu Pro Glu Gly Ser Lys Val Thr Val Gly Asp Asn Gly Asp
2495                2500                2505

Val Thr Val Thr Tyr Pro Asp Gly Ser Lys Asp Thr Ile Pro Gly
2510                2515                2520

Asp Lys Val Val Glu Gly Lys Gly Thr Glu Gly Gln Thr Asp Ala
2525                2530                2535

Asp Lys Asn Glu Pro Lys Val Pro Gly Asp Lys Val Lys Val Asp
2540                2545                2550

Asp Pro Asn Lys Leu Thr Glu Asp Glu Lys Ser Glu Val Val Lys
2555                2560                2565

Ala Val Glu Asp Ala Asn Lys Asp Glu Asn Gly Lys Ser Thr Leu
2570                2575                2580

Pro Glu Gly Ser Lys Val Thr Val Gly Asp Asn Gly Asp Val Thr
2585                2590                2595

Val Thr Tyr Pro Asp Gly Ser Lys Asp Thr Ile Pro Gly Asp Lys
2600                2605                2610

Val Val Glu Gly Arg Gly Thr Glu Gly Gln Thr Asp Ala Asp Lys
2615                2620                2625

Asn Glu Pro Lys Val Pro Gly Asp Lys Val Lys Val Asp Asp Pro
2630                2635                2640

Thr Lys Leu Thr Glu Asp Glu Lys Ser Asp Val Glu Gln Ala Ile
2645                2650                2655

Lys Asp Ala Asn Lys Asp Glu Asn Gly Lys Ser Thr Leu Pro Glu
2660                2665                2670

Gly Ser Lys Val Thr Val Gly Asp Asn Asp Asp Val Thr Val Thr
2675                2680                2685

Tyr Pro Asp Gly Ser Lys Asp Thr Ile Pro Gly Asp Lys Val Val
2690                2695                2700

Glu Gly Lys Gly Thr Glu Gly Gln Thr Asp Ala Asp Lys Asn Glu
2705                2710                2715

Pro Lys Val Pro Gly Asp Lys Val Lys Val Asp Asp Pro Asn Lys
2720                2725                2730

Leu Met Glu Asp Glu Lys Ser Asp Val Glu Gln Ala Ile Lys Asp
2735                2740                2745

Ala Asn Lys Asp Glu Asn Gly Lys Ser Thr Leu Pro Glu Gly Ser
2750                2755                2760

Lys Val Thr Val Ser Asp Asn Gly Asp Val Thr Ile Thr Tyr Pro
2765                2770                2775

Asp Gly Ser Lys Asp Thr Ile Pro Gly Asp Gln Val Ile Glu Gly
2780                2785                2790

Lys Ser Asp Ala Asp Lys Asn Thr Pro Asn Val Pro Gly Gly Asp
2795                2800                2805
```

```
Lys Val Lys Val Asp Asp Pro Thr Lys Leu Thr Asp Asn Glu Lys
2810                2815                2820

Asn Ala Val Lys Asp Lys Val Asp Glu Ala Asn Ser Asn Leu Pro
    2825                2830                2835

Asp Gly Thr Lys Val Thr Val Gly Asp Asp Gly Thr Thr Thr Ile
2840                2845                2850

Thr Tyr Pro Asp Gly Ser Thr Asn Thr Ile Ser Gly His Asp Leu
    2855                2860                2865

Val Thr Gly Lys Thr Asp Ala Asp Lys Tyr Pro Leu Asn Pro Gly
2870                2875                2880

Gln Ala Val Asn Val Val Asp Pro Asn His Leu Thr Gln Ala Glu
    2885                2890                2895

Gln Asp Gln Val Lys Glu Ala Ile Gln Thr Thr Asn Pro Thr Ala
2900                2905                2910

Pro Ile Ala Thr Ile Thr Val Asp Thr Ala Gly Asn Val Gln Val
    2915                2920                2925

Thr Phe Ala Asp Gly Ser Thr Thr Thr Leu Gln Ala Asn Leu His
2930                2935                2940

Lys His Val Thr Glu Ala Thr Thr Gly Ser Ala Ile Lys Pro Gly
    2945                2950                2955

Val Gly Thr Asn Gly Gly Gln Thr Lys Gly Ala Thr Ser Thr Asn
2960                2965                2970

Gln Thr Ala Thr Lys Gln Gln Ala Gln Gln His Leu Pro Gln Thr
    2975                2980                2985

Gly Asp Gln Pro Ala Thr Trp Ala Met Leu Ser Gly Leu Gly Val
2990                2995                3000

Ala Phe Leu Gly Leu Leu Gly Leu Lys Lys Lys Arg Glu Asp
    3005                3010                3015

<210> SEQ ID NO 16
<211> LENGTH: 1472
<212> TYPE: PRT
<213> ORGANISM: Artificial Sequence
<220> FEATURE:
<223> OTHER INFORMATION: Based on Lactobacillus reuteri sequence

<400> SEQUENCE: 16

Met Glu Ile Lys Lys His Phe Lys Leu Tyr Lys Asp Gly Lys Lys Trp
1               5                   10                  15

Cys Cys Ala Ala Ile Ala Thr Thr Val Leu Gly Ile Gly Leu Ala Ile
                20                  25                  30

Gly Ser Pro Ser Val Leu Ala Asp Ala Asp Thr Ile Thr Ser Thr Ser
        35                  40                  45

Asp Ala Asn Asn Ser Leu Val Lys Asn Asp Asn Thr Ser Asp Thr Asp
    50                  55                  60

Ser Asn Ser Glu Ser Thr Phe Thr Asp Thr Asn Lys Asn Ser Thr Asn
65                  70                  75                  80

Glu Lys Glu Ile Asn Glu Lys Asn Ile Asp Ser Ser Gln Gln Ile
                85                  90                  95

Asn Gln Glu Gln Thr Lys Ser Asn Asn Ser Glu Glu Gln Thr Thr Pro
            100                 105                 110

Val Asn Val Lys Ala Glu Asn Thr Asp Ile Lys Asp Ser Ile Pro Glu
        115                 120                 125

Lys Ser Thr Pro Asn Ser Phe Lys Glu Ile Asn Gly Ser Thr Tyr Tyr
    130                 135                 140
```

-continued

Tyr Gly Glu Asn Gly Asp Leu Tyr Arg Asn Gln Phe Tyr Asn Asn Trp
145                 150                 155                 160

Gly Arg Thr Tyr Tyr Phe Gln Ala Asn Gly Ala Arg Leu Asp Asn Gly
            165                 170                 175

Phe Tyr Asn Asn Trp Gly Arg Thr Tyr Tyr Phe Gly Ser Asp Gly Ala
        180                 185                 190

Arg Trp Asp Asn Arg Phe Tyr Asn Asn Trp Gly Arg Thr Tyr Tyr Phe
    195                 200                 205

Gln Asn Asp Gly Ser Arg Leu Asp Asn Ser Phe Tyr Asn Asn Trp Gly
210                 215                 220

Arg Thr Tyr Tyr Phe Gly Val Asp Gly Ala Arg Trp Asp Asn Arg Tyr
225                 230                 235                 240

Met Val Lys Trp Gly Arg Ala Tyr Tyr Phe Gly Asn Asp Gly Ala Leu
            245                 250                 255

Leu Gln Asn Gln Leu Lys Ser Ile Asn Gly Ile Asn Tyr Trp Ile Asn
        260                 265                 270

Asn Glu Gly Ile Ile Pro Leu Lys Asn Gln Phe Leu Thr Ala Asn Glu
    275                 280                 285

Asn Gln Leu Phe Tyr Phe Asp Gly Asn Gly Ser Leu Val Val Asn Lys
290                 295                 300

Phe Tyr His Asn Trp Gly His Thr Tyr Tyr Phe Gly Ser Asp Gly Ala
305                 310                 315                 320

Arg Tyr Thr Asp Gln Phe Leu Asn Arg Asp Gly Lys Val Tyr Tyr Phe
            325                 330                 335

Asp Asn Gln Gly Ile Met Tyr Gln Asp Gln Tyr Tyr Lys Asn Trp Gly
        340                 345                 350

His Thr Tyr Tyr Phe Gly Ser Asp Gly Ala Arg Tyr Thr Asp Gln Phe
    355                 360                 365

Leu Asn Arg Asp Gly Lys Val Tyr Tyr Phe Asp Asn Gln Gly Ile Met
370                 375                 380

Tyr Gln Asp Gln Tyr Tyr Lys Asn Trp Gly His Thr Tyr Tyr Phe Gly
385                 390                 395                 400

Ser Asp Gly Ala Arg Tyr Thr Asp Gln Phe Leu Asn Arg Asp Gly Lys
            405                 410                 415

Val Tyr Tyr Phe Asp Asn Gln Gly Ile Met Tyr Gln Asp Gln Tyr Tyr
        420                 425                 430

Lys Asn Trp Gly His Thr Tyr Tyr Phe Gly Ser Asp Gly Ala Arg Tyr
    435                 440                 445

Thr Asp Gln Phe Leu Asn Arg Asp Gly Lys Val Tyr Tyr Phe Asp Asn
450                 455                 460

Gln Gly Ile Met Val Thr Asn Gln Val Arg Val Ile Asp Gly Lys Gly
465                 470                 475                 480

Tyr Glu Phe Asn Asp Asn Gly Glu Ala Thr Glu Thr Ser Asp Met Gly
            485                 490                 495

Gln Thr Arg Asp Thr Val Ala Lys Glu Val Ala Gln Ala Leu Thr Asn
        500                 505                 510

Gln Gly Ile Lys Gly Val Lys Tyr Asp Trp Arg Asn Thr Asn Asn Asp
    515                 520                 525

Tyr Gln Glu Leu Ala Leu His Asp Ile Ala Gln Glu Val Ala Gln Gly
530                 535                 540

Asp Thr Asn Pro Asp Lys Asn Val Ile Glu Lys Lys Leu Gln Ala Asn
545                 550                 555                 560

Asn Leu Leu Ser Gly Lys Val Leu Val Val Tyr Ser Thr Asp Phe Thr

```
                    565                 570                 575
Asn Asp Asp Pro Gln Lys Ile Thr Asn Thr Phe Met Asn Ser Tyr Asp
                580                 585                 590
Phe Thr Asn Ala Asp Asn Ser Val Leu Gly Val Gly Ala Asp Leu Asn
                595                 600             605
Lys Asn Lys Leu Val Ile Ile Leu Phe Lys Pro Gly Glu Lys Ala Glu
        610                 615                 620
Gln Pro Gln Ala Thr Ser Thr Ile Ser Ala Ser Ile Ser Asp Ile Phe
625                 630                 635                 640
Lys Lys Ala Gly Val Asn Val Asp Val Asp Asn Gly Leu Thr Lys Gly
                645                 650                 655
Ser Val Val Asn Ser Ala Asp Leu Gly Asn Ala Leu Thr Asn Gly Thr
                660                 665                 670
Ala Glu Leu Leu Lys Gly Asp Lys Gly Thr Ile Ile Ser Gln Glu Val
                675                 680                 685
Leu Lys Ala Ile Phe Ala Ala Phe Ala Gly Asn Thr Ser Ala Val Glu
        690                 695                 700
Gly Thr Lys Asn Tyr Tyr Asn Gly Asn Asp Ala Tyr His Tyr Glu Phe
705                 710                 715                 720
Trp Leu Glu Gly Gln Ser Ala Asp Asp Lys Leu Asn Asn Phe Leu Ala
                725                 730                 735
Leu Asn Lys Gly Ala Lys Tyr Gly Asp Gln Leu Lys Val Asn Tyr Thr
                740                 745                 750
Ala Thr Leu Val Phe Gly Gln Glu Thr Gly Thr Asn Ser Asn Glu Ser
                755                 760                 765
Lys Val Pro Ala Ser Glu Arg Thr Asp Glu Gln Leu Asp Leu Ala Tyr
        770                 775                 780
Lys Thr Gly Thr Asp Thr Gly Leu Arg Tyr Asp Ser Val Lys Val Glu
785                 790                 795                 800
Lys Ile Pro Gly Met Thr Asp Asp Met Val Arg Gly Val Asp Val Ser
                805                 810                 815
Ser Tyr Gln Ala Leu Ile Asn Ala Gly Val Lys Phe Tyr Asp Phe Asn
                820                 825                 830
Gly Gln Glu Ser Asn Leu Phe Lys Ile Leu Lys Asp Ser Gly Val Asn
        835                 840                 845
Trp Val Arg Leu Arg Val Trp Asn Asp Pro Tyr Asn Ala Gln Gly Gln
        850                 855                 860
Pro Tyr Ala Gly Gly Asp Asn Asn Glu Glu Asn Leu Ile Lys Met Ala
865                 870                 875                 880
Lys Glu Ala Ser Asp Asn Gly Leu Lys Leu Leu Ile Asp Phe Gln Tyr
                885                 890                 895
Ser Asp Phe Trp Thr Asp Pro Ala Gln Gln Ile Leu Pro Lys Ala Trp
                900                 905                 910
Arg Asn Leu Ser His Gly Glu Met Ser Gln Glu Val Tyr Leu Tyr Thr
        915                 920                 925
Ser Lys Ile Leu Asn Asp Leu Gln Lys Ala Gly Ala Ser Val Lys Met
930                 935                 940
Val Gln Ile Gly Asn Glu Ile Thr Asn Gly Ala Phe Gly Leu Tyr Thr
945                 950                 955                 960
Gly Arg Asn Gly Gly Asn Trp Ala Ser Leu Trp Glu Thr Ser Asp
                965                 970                 975
Gly Asp Gln Val Ala Lys Tyr Ile Gln Ala Gly Ser Ser Ala Val Arg
                980                 985                 990
```

-continued

```
Arg Ile Asp Pro Thr Ile Lys Val  Ala Ile Gln Leu Glu  Thr Pro Glu
        995             1000               1005

Ile Asn  Lys Tyr Arg Gly Ile  Met Asn Val Leu Lys  Lys Asn Asn
        1010            1015               1020

Val Asp  Tyr Asp Tyr Leu Gly  Thr Ser Tyr Tyr Pro  Phe Trp Ser
        1025            1030               1035

Thr Thr  Gln Gly Asn Gly Trp  Tyr Asp Asn Val Asp  Leu Gly Tyr
        1040            1045               1050

Gly Ala  Asn Thr Pro Val Asn  Leu Glu Ala Ile Glu  Lys Met Ala
        1055            1060               1065

Trp Asn  Glu Phe Gly Lys Arg  Thr Val Ile Leu Glu  Ser Gly Trp
        1070            1075               1080

Leu Asn  Asn Thr Asn Asp Ala  Asp Gly Thr His Asn  Ser Val Gly
        1085            1090               1095

Glu Asn  Asn Glu Thr Thr Asn  Ile Asp Arg Tyr Ser  Ala Asp Pro
        1100            1105               1110

Gln Gly  Gln Val Asp Glu Ile  Glu Asp Met Tyr Asn  Ala Ile Ile
        1115            1120               1125

Ala Gln  Lys Gly Leu Gly Ala  Phe Tyr Trp Glu Pro  Ala Trp Ile
        1130            1135               1140

Pro Val  Lys Ala Gly Trp Asn  Asn Trp Gln Tyr Asn  Lys Leu Met
        1145            1150               1155

Ser Asn  Ile Tyr Gly Ser Gly  Trp Ala Ser Gln Tyr  Ala Lys Gly
        1160            1165               1170

Tyr Ala  Pro Asp Ser Val Leu  Tyr Tyr Asp Gly Lys  Glu Ala Trp
        1175            1180               1185

Gly Gly  Ser Ser Trp Asp Asn  Ile Ser Leu Phe Asp  Asp His Gly
        1190            1195               1200

His Pro  Leu Gln Ser Leu Asn  Val Tyr Asn Gly Met  Leu Asn Gly
        1205            1210               1215

Tyr Glu  Ser Pro Lys Asn Val  Lys Ser Ser Leu Ser  Thr Gln Leu
        1220            1225               1230

Val Lys  Ile Trp Asn Glu Thr  Asp Val Ile Pro Asn  Asp Gly Leu
        1235            1240               1245

Thr Glu  Gly Thr Lys Leu Ser  Thr Asp Leu Phe Gly  Thr Thr Gln
        1250            1255               1260

Leu Ser  Gly Asn Asp Gly Gln  Ser Ile Gly Asn Ala  Glu Leu Thr
        1265            1270               1275

Lys Leu  Ala Gly Arg Leu Lys  Asp Gly Ile Ser Ser  Lys Val Tyr
        1280            1285               1290

Thr Ala  Ala Asn Gly Ala Arg  Tyr His Tyr Ile Tyr  Trp Leu Glu
        1295            1300               1305

Gly Gly  Asn Asn Lys Val Asn  Thr Phe Val Ser Ala  Asn Lys Asp
        1310            1315               1320

Ala Lys  Tyr Gly Gln Pro Leu  Ile Ala Asn Tyr Ser  Ala Thr Val
        1325            1330               1335

Val Val  Asp Ser Glu Pro Gly  Thr Gln Val Ala Thr  Ser Pro Leu
        1340            1345               1350

Gln Ile  Lys Ile Ser Gln Val  Trp Asn Thr Val Asn  Asn Glu Glu
        1355            1360               1365

Ile Lys  Ile Asp Asn Pro Leu  Lys Gln Gly Asp Leu  Ile Thr Asp
        1370            1375               1380
```

-continued

Lys Ser Asp Asn Ala Phe Ser Gly Ile Leu Asn Ser Lys Asp Ile
1385                1390                1395

Lys Glu Ala Leu Thr Gly Glu Lys Gly Lys Asp Val Ser Glu Ser
1400                1405                1410

Thr Val Asn Asp Val Lys Ser Leu Leu Pro Lys Glu Val Lys Gly
1415                1420                1425

Ser Lys Thr Tyr Thr Ala Asp Gly Asn Gln Tyr Tyr Tyr Asp
1430                1435                1440

Phe Trp Leu Ala Ser Val Glu Thr Ser Asn Val Asn Tyr Gly Glu
1445                1450                1455

Pro Ile Ile Val Asn Tyr Thr Ala Ser Leu Lys Trp Leu Gly
1460                1465                1470

<210> SEQ ID NO 17
<211> LENGTH: 1063
<212> TYPE: PRT
<213> ORGANISM: Artificial Sequence
<220> FEATURE:
<223> OTHER INFORMATION: Based on Lactobacillus reuteri sequence

<400> SEQUENCE: 17

Met Glu Lys Thr Met Lys Lys Lys Ala Leu Val Ala Thr Thr Ala Val
1               5                   10                  15

Ala Gly Ile Thr Leu Val Gly Glu Val Thr Thr Val His Ala Ala Asp
            20                  25                  30

Asn Val Gln Gln Pro Val Asn Glu Gln Asn Val Asn Gln Ser Ser Gln
        35                  40                  45

Glu Glu Lys Gln Ala Ala Gln Asn Leu Gln Asn Ala Gln Ser Asp Val
    50                  55                  60

Asn Thr Ala Thr Glu Ala Asn Ser Asn Ala Gln Asp Asn Leu Ala Ser
65                  70                  75                  80

Ala Asn Asn Asn Leu Ser Asn Ala Lys Lys Ala Val Ser Asp Gln Ala
                85                  90                  95

Ala Lys Val Ala Asp Ala Thr Lys Ala Gln Ser Asp Ala Ser Thr Lys
            100                 105                 110

Val Asp Asn Asp Asn Lys Val Val Ala Asp Ala Gln Gln Lys Ala Asp
        115                 120                 125

Gln Ala Thr Pro Ala Asn Ile Glu Asn Ala Lys Gln Ala Ile Glu Gly
    130                 135                 140

Gln Asn Lys Val Ile Asp Gln Asp Asn Glu Asn Ile Lys Tyr Ser Asn
145                 150                 155                 160

Thr Asp Gln Asp Lys Ala Gln Asn Thr Leu Asn Asn Ala Gln Ser Asn
                165                 170                 175

Glu Asp Lys Ala Asn Ala Thr Leu Ser Asn Lys Ser Ser Gln Ala
            180                 185                 190

Ser Ala Gln Asn Asn Val Lys Gln Ala Glu Asp Ala Leu Asn Gly Thr
        195                 200                 205

His Leu Val Glu Ala Gln Asn Ala Phe Asn Gln Ala Ser Asn Val
    210                 215                 220

Glu Asn Ala Gln Ser Lys Tyr Asp Gln Ala Asn Asn Gln Leu Ser Asp
225                 230                 235                 240

Ala Gln Lys Lys Val Thr Thr Asn Gln Asn Asp Leu Thr Ala Lys Asn
                245                 250                 255

Lys Ala Leu Asp Asn Ile Asn Asn Gln Val Asp Thr Asp Gln Asn Asn
            260                 265                 270

-continued

```
Val Asn Ser Asn Gln Ala Thr Ala Asp Ser Ala Ser Ala Thr Gln
            275                 280                 285

Val Ala Gln Asn Ala Val Asp Gln Thr Lys Gln Ser Leu Asp Lys Val
290                 295                 300

Ile Glu Glu Leu Asn Gly Phe Ser Glu Asn Thr Ile Lys Val Pro Ala
305                 310                 315                 320

Gly Ala Gln Glu Ala Tyr Glu Ala Phe Ile Asp Ala Val Asp Asn Asn
                325                 330                 335

Ala Asp Gln Ser Gln Leu Asp Ser Leu Ala Lys Lys Met Tyr Asp Thr
            340                 345                 350

Leu His Gln Gly Gln Gly Thr Asn Gly Ile Asn His Phe Asn Ser Ser
        355                 360                 365

Lys Tyr Asp Gln Asn Gln Leu Val Asp Val Asp His Leu Thr Thr Asp
    370                 375                 380

Gln Leu Asn Glu Leu Thr Gln Phe Ala Ala Asp Met Ile Asn Ser Ala
385                 390                 395                 400

Arg Lys Ala Trp Gly Ser Asp Lys Asn Ala Gly Thr Leu Ile Pro Thr
                405                 410                 415

Gln Gly Val Ser Glu Met Ala Gln Gln Ile Ala Lys Gly Tyr Val Ser
            420                 425                 430

Asp Asn Trp His Ile Ser Gln Gly His Asp Val Lys Arg Val Thr Ala
        435                 440                 445

Ala Ala Gly Leu Ile Gly Leu Asn Asp Ala Gly Gln Phe Tyr Glu Asp
    450                 455                 460

Ala Ser Glu Gly Tyr Val His Ala Trp Pro Trp Glu Lys Asp Ser Tyr
465                 470                 475                 480

Thr Met Asp Asn Leu Lys Glu Ala Val Tyr Asp Ser Ile Leu Gly Met
                485                 490                 495

Leu Phe Ala Asp Asp Asn Ser Gly Asn Gly His Met Thr Asp Leu Leu
            500                 505                 510

Gly Leu His Val Asn Arg Lys Glu Asp His Gln Tyr Phe Gly Leu Ser
        515                 520                 525

Thr Asn Met Cys Pro Gly Ser Tyr Met Gly Gln Leu His Phe Ile Ile
    530                 535                 540

Val Glu Asn Asp Pro Ala Tyr Ile Lys Asp Pro Gln Thr Phe Asn Ala
545                 550                 555                 560

Lys Gly Gly Thr Thr Lys Ile Glu Tyr Ile Asp Pro Lys Val Gln Leu
                565                 570                 575

Asn Gln Gln Lys Asp Ile Leu Thr Thr Thr Leu Ser Thr Gln Gln Ala
            580                 585                 590

Asp Leu Ala Thr Lys Gln Asp Ala Leu Asn Lys Ala Asn Gln Asn Leu
        595                 600                 605

Ala Asn Ala Lys Lys Gln Leu Ser Glu Asp Gln Asp Leu Gln Thr Val
    610                 615                 620

Ala Gln Gln Asn Arg Asp Ser Ala Gln Lys Ala Leu Asn Asp Ala Thr
625                 630                 635                 640

Ala Lys Val Ser Asn Leu Gln Ala Thr Val Asn Ser Leu Ser Gln Asp
                645                 650                 655

Leu Asn Ser Ala Lys Ala Thr Leu Asp Gln Ala Lys Lys Thr Leu Glu
            660                 665                 670

Ser Tyr Thr Ala Asp His Lys Ala Lys Leu Asp Asn Tyr Asn Asn Ala
        675                 680                 685

Lys Ala Ala Leu Asp Asp Ala Asn Lys Ala Val Ala Glu Ala Gln Ser
```

690             695             700
Ala Val Asp Thr Ala Val Asn Glu Thr Lys Ile Ala Gln Asn Asn Leu
705                 710                 715                 720

Asp Gln Lys Lys Gln Ala Val Thr Asp Ala Gln Asn Lys Leu Ala Asn
                725                 730                 735

Asp Gln Glu Tyr Leu Ala Thr Leu Lys Gln Asn Leu Ala Asp Leu Gln
            740                 745                 750

Asn Ala Pro Gln Asn Leu Gln Lys Ala Lys Asp Gln Leu Ala Lys Asp
        755                 760                 765

Gln Ile Ala Leu Asp Asn Ala Asn Lys Asp Leu Gln Asn Gln Lys Asp
    770                 775                 780

Ser Leu Asp Glu Leu Asn Lys Lys Leu Glu Asp Ala Gln Val Lys Val
785                 790                 795                 800

Asn Glu Ala Gln Ser Ala Ala Asn Val Thr Lys Ala Thr Leu Asp Gln
                805                 810                 815

Ala Gln Ala Lys Leu Ser Asp Ala Glu Ala Thr Trp Lys Glu Leu His
            820                 825                 830

Asn Asp Ala His Arg Tyr Gly Asn Val Val Lys Val Thr Pro Ile Thr
        835                 840                 845

Met Glu Ala Gly Thr Ser Leu Pro Asp Pro Val Ile Glu Asn Gly Phe
    850                 855                 860

Thr Val Asn Thr Gly Thr Asn Gln Leu Phe Val Ser Leu Ala Ala Ile
865                 870                 875                 880

Asp Ser Ser Asn Asn Ile Pro Gln Gly Thr Lys Ala Ser Trp Ala
                885                 890                 895

Asn Arg Ser Lys Ala Leu Thr Asp Ser Gln Asn Ala Gly Ser Tyr Ser
            900                 905                 910

Glu Asp Ile Leu Ile Thr Phe Pro Asp Asn Ser Thr Val Thr Val Pro
        915                 920                 925

Val Asp Leu Thr Val Thr Ala Lys Lys Ile Thr Glu Asp Gln Lys Ala
    930                 935                 940

Thr Glu Gly Gly Tyr His Ile Val Asn Gly Ser Val Val Asp Lys Gln
945                 950                 955                 960

Asn Asn Leu Val Ser Gly Trp Thr Val Lys Asn Gly Gln Met Val Asp
                965                 970                 975

Pro Glu Gly Asn Val Ile Lys Thr Thr Met Ser Thr Ala Gln Gly Val
            980                 985                 990

Thr Ile Glu Lys Asn Asn Ser Lys Ser Gly Asn Thr Lys Thr Asn Met
        995                 1000                1005

Ile Gln Thr Ser Leu Thr Ile Ala Asn Asn Lys Ala Thr Thr Asn
    1010                1015                1020

Lys Asp Asn Gln Leu Pro Gln Thr Gly Asn Tyr Asn Asn Asn Thr
    1025                1030                1035

Lys Val Leu Gly Leu Ala Gly Ile Ala Leu Ala Ser Ala Leu Thr
    1040                1045                1050

Met Phe Gly Tyr Lys Lys Arg Gln His Asn
    1055                1060

<210> SEQ ID NO 18
<211> LENGTH: 212
<212> TYPE: PRT
<213> ORGANISM: Artificial Sequence
<220> FEATURE:
<223> OTHER INFORMATION: Based on Lactobacillus reuteri sequence

<400> SEQUENCE: 18

```
Met Lys Ser Thr Thr Lys Lys Ile Leu Ala Ser Ser Leu Gly Val Ala
1               5                   10                  15
Gly Ala Met Ala Met Gly Thr Val Thr Ala Lys Ala Asp Thr Thr Val
            20                  25                  30
Thr Val Asn Ala Gly Asp Ser Leu Asn Gly Ile Ala Gln Lys Tyr Asn
        35                  40                  45
Val Ser Ala Asp Asp Ile Ala Thr Ala Asn His Leu Gln Asn Lys Glu
    50                  55                  60
Leu Ile Phe Val Gly Gln Lys Leu Thr Ile Pro Thr Lys Asp Lys Asn
65                  70                  75                  80
Glu Thr Pro Ala Asn Asn Ala Glu Lys Lys Asp Gln Ala Ser Lys Asn
                85                  90                  95
Ser Gln Ser Leu Gln Asp Ser Val Asn Lys Ala Met Ser Tyr Leu Gly
            100                 105                 110
Thr Pro Tyr Val Trp Gly Gly Asn Lys Pro Gly Gly Phe Asp Cys Ser
        115                 120                 125
Gly Leu Val Gln Tyr Cys Tyr Gly Ile Pro Gln Arg Thr Thr Tyr Glu
    130                 135                 140
Gln Gln Ala Leu Gly Pro His Ile His Asp Asn Val Leu Asn Ala Pro
145                 150                 155                 160
Tyr Gly Ala Leu Val Phe Tyr Gly Ser Asp Asp Ala Pro Tyr His Val
                165                 170                 175
Ala Ile Ser Leu Gly Asp Gly Arg Ile Ile Gln Ala Pro Asn Glu Asn
            180                 185                 190
Glu Thr Val Lys Ile Thr Asp Gln Gln Tyr Phe Pro Gly Asn Tyr Tyr
        195                 200                 205
Val Val Met His
    210
```

<210> SEQ ID NO 19
<211> LENGTH: 1107
<212> TYPE: DNA
<213> ORGANISM: Artificial Sequence
<220> FEATURE:
<223> OTHER INFORMATION: Based on Lactobacillus reuteri sequence

<400> SEQUENCE: 19

```
atgcgtaatc aattcatcga tgtttcaagt tatcaaccag atactgttgc cttttttccaa      60
gctgctaaag ctcagggtgc attaggggtc gttgttaagt taacggaagg gtccgaagat     120
ggttcggctt atgttaatcc acgtgcggcc gctcaaattc gtaatgcctt agcggttggc     180
ttgcgcgttt cctgttacca ctttgctcgt tatacatcag tgactgatgc acaaaatgaa     240
gctcgattct tcgttaaaat cgctaagcaa tttggtatgt atgacgatac tttgatgatt     300
gatgatgcgg aagttcattc aactgcagat tatcaatcag tatccttagc ctttcttcaa     360
gaagtagaag ctcttggtta caagaatact gggatttact ccatgaagtc cttcttcact     420
ggcggtattc ttaattcaca tggctttgat ccccggaaga tttggattgc tggctatggt     480
gtgactgaac tggggattga taatgcaagt gcttggcaat attctgatca tagcatcatg     540
ggaattgata ctagttatga ctttgacggt gcctttacga ctggtttagt atcaggcaat     600
gttccgcaag ctgttattcc agcaccacag ccggttcaac atattggtca cccagctact     660
ggaacctaca ttgttcagcc gggcgataca ttgagtggaa ttgcagaaaa atacgggact     720
acttatcaga acctagcagc aatcaatggt attggtaatc caaaccagat caatgtcggc     780
```

```
caagtcctca aagtcaccgg aaaagtatca acgaaaata cttactttgt tcaatcaggc      840
gatacgttat ccggaattgc caccaaattc ggcaccactg tctcagacct cgtaagccgt      900
aatcacatta ctaacccgaa tgtgatctac gttgggcaaa aactctactt agccggcaac      960
ggacaatcca atgcttatac tgtccaagca ggggacacac taagcggaat tgcggctaag     1020
tttggcaaga cctggcaagc attagctcaa agaatggca tcgcaaatcc taatatgatt     1080
ttcattggtc aaacaattca gatttaa                                         1107

<210> SEQ ID NO 20
<211> LENGTH: 2439
<212> TYPE: DNA
<213> ORGANISM: Artificial Sequence
<220> FEATURE:
<223> OTHER INFORMATION: Based on Lactobacillus reuteri sequence

<400> SEQUENCE: 20
gtgtaccgaa ttattggtta taatgaacca acagataaag caggatttat tgtactggat       60
ccccgagtta atcgtcatat tagttcggga aaactcacgc ttaaagaatc taatattgat      120
gatttgacta ttacggttaa tcaagcaagt ccattatggg acaacgtaag gccttatcat      180
actcatgtta acgtttatga tgataatgaa cttattttc gtggacgagc tatcaaacct      240
aaaaagtcga tggaagaaag cggacaattc attcgtgaat atgttttga agatattgaa      300 gcatatctca tggatagcac ccaaagattt tatgaaggtg ttggtcaaac gcccaaagaa      360
tttttacaaa ctttaatcga tgttcataat tcacaggttc ctgactataa aaagtttcaa      420
gtccggaatg taaatgtcac taataataag gatgaccaat atcgacaaat tgattatccc      480
aaaactagcg atgctattaa tgataaatta gttaaatctc ttggtggtta tattgtgact      540
acttacaacg ctaacggaat aaactacatt gactactaa cggatattgg ggttgatcat      600
aaagatgata ctcctattca gttagctaaa aatatgaagt ctgcaagtat gcaaattgat      660
cctactaagg tgattacaag actgattcca ctgggaaaga cactagaacc atcaaaagtt      720
gatgtaagtg atgatgatgg agagggcggt tctggatcat tagatagccc tgaagaattt      780
tgtaaatcag aaattaatgc tacttggggt agtgatatta ataatatgaa acaagatttt      840
gccgctcgtt cttcgagagt tcgggcttgg ggagtggacg ttaatcgttt atatgatgtg      900
gtgaaaaatg ctggagtaag tcctgaatgg ttctttgctt atgaacttca agaacaagga      960
acttactatg atggcttaa ccatacttat cgacacggtg atgcgtatag tgatgcgcaa     1020
tctgtttgtg agtggattaa aaattgttca aatagtaatt ccattaatcc agcatggagc     1080
gcaccggaag gatcaatggc gccgaatcaa gcattagcgg ataaatggaa tcaagagttt     1140
ggaaaaggta ctattggccg cgtttattta caagggactg ccgctgctgt ttgggattta     1200
gctggtcaaa cgcctaatcc agctattgga aagccaatta gtggatgcat tcttgtatt     1260 aaacgttggg gtggtcattc taatgcagct ggtggtacat gggatgggcc ttttcctgat     1320
gttggggaag gtcatttttc tcaagttcag agtttcggaa atgatggcgg atatcgtcaa     1380
aatagttatc acgatggtgt ggattttgga tcaatagatc atcctggtag agaagtgcat     1440
tgtattcatg gtggaacggt aactatcaaa tcagctatgg gtggcttagg taattttgtg     1500
gttattcata cgccggaagg attcaatatc gtttatcaag aagcttttag ttctccctct     1560
aatattattg ttagtgttgg gcaaaaagta aaaactggtg atgtaattgg atatcgtgat     1620
acagaccatg ttcatattgg cgtaactaag caagattttt atcaagcagt tcgaaattct     1680
```

```
ttttctcctg caggtggttg ctagatcca gtaaaactaa ttaagaagg tggcgatggg    1740 tctaaaccac aagaaggaaa gaaagatcaa actgttgata atagtaatgc tgcacgtcct   1800
aaattaacca ttactactgt caataacggt agagactata ttgatattcc tgatttacaa   1860
aaagaattcg gtattattga gggaactgtt gaatttgata atgtagatga tccgaatgtt   1920
ttaatgcaac aagctcaaac atggataaag gctcaaagaa tacctcaaag ttgggaagtt   1980
acagctttag aattacatat gacaaacttc aaatctttta aggttgctga taggtacatg   2040
tttattaatc caaatgttgc aaaaccccaa ttattacgaa ttactcaaaa agaaattgat   2100
ttactaaagc cccatgcgtc ttcattaacg attggtgata agacgatggg gcttactgat   2160
tatcagttag aaaatcaagt caattttcaa caatttaagg aaattcgagt gatggttaat   2220
caggttgtcc aaacccaaga gcaatctgct aataacaata ataaggttat gcaaaatttt   2280
gctagtagtg ctgatcttgc acaaatgaga caggatctaa gaaatcttca agatgataac   2340
gatcgtgctc gcaaaggaat ggtttcctta gaagaattca ataaactaaa ggaacaagta   2400
gaaaaactaa caacaggagg cgatgataat ggcaagtga                          2439
```

<210> SEQ ID NO 21
<211> LENGTH: 739
<212> TYPE: PRT
<213> ORGANISM: Artificial Sequence
<220> FEATURE:
<223> OTHER INFORMATION: Based on Lactobacillus reuteri sequence

<400> SEQUENCE: 21

```
Met Asn Lys Ala Asn Gln Lys Val Ala Asp Asp Thr Thr Ala Val Asn
1               5                   10                  15

Asn Lys Gln Thr Asp Val Asn Asn Ala Ala Glu Ala Lys Lys Asn Ala
                20                  25                  30

Asp Glu Ala Leu Lys Asn Ala Asn Asp Ala Gln Thr Ser Ala Gln Lys
            35                  40                  45

Asn Lys Asp Ala Lys Gln Ala Ile Ala Asp Glu Ala Ser Val Ala Leu
        50                  55                  60

Ala Asp Ala Asn Thr Ala Val Lys Asp Ala Gln Ala Lys Val Asp Ala
65                  70                  75                  80

Ile Asn Asp Lys Leu Ala Asn Phe Asn Thr Ile Thr Leu Pro Ala Gly
                85                  90                  95

Tyr Lys Asp Asp Leu Ile Ala Tyr Tyr Asn Tyr Phe Gly Asn Ser Asn
            100                 105                 110

Tyr Asn Gln Asp Glu Ala Asn Asn Leu Ala Gln Asp Leu Leu Lys Tyr
        115                 120                 125

Arg Asp Gln Ala Met Ser Gln Asn Lys Phe Lys Asp Asn Leu Ser Asp
    130                 135                 140

Asp Arg Val Val Asp Ile Asp Asn Leu Asn Ser Thr Asp Arg Ala Glu
145                 150                 155                 160

Leu Ser Gln Phe Val Ala Ser Leu Ile Asn Gln Val Arg Thr Gln Met
                165                 170                 175

Gly Thr Asn Leu Val Ile Ser Ser Pro Ala Ala Asp Asp Tyr Ala Glu
            180                 185                 190

Gln Val Ser Gln Asn Tyr Asn Lys Asp Asn Trp Asn Ser Ala Asp Asn
        195                 200                 205

Gly Lys His Asp Gln Ser Ala Leu Asn Asn Ala Thr Asp Gln Leu Asn
    210                 215                 220

Ile Ser Trp Asn Gly Glu Asn Met Gly Leu Asp Gln Ser Ile Phe Thr
```

```
            225                 230                 235                 240
        Thr Asp Tyr Thr Val Leu Thr Asp Gly Thr Lys Leu Pro Thr Gly Asn
                        245                 250                 255

Lys Gln Thr Ile Asn Asp Leu Lys His Leu Ile Tyr Asp Asp Phe Ile
                        260                 265                 270

Ser Met Met Phe Asp Asp Ala Asp Ser Ala Trp Gly His Ala Thr Asn
                        275                 280                 285

Phe Ala Gly Ile Asp Asn Phe Ala Ala Glu Lys Gln Ala Val Gly Phe
                        290                 295                 300

Ser Leu Asp Lys Phe Tyr Asn Thr His Tyr Asp Leu Val Glu Ala Asn
        305                 310                 315                 320

Gln Lys Val Glu Glu Asn Ser Tyr Thr Leu Pro Ser Ile Asn Ala Leu
                        325                 330                 335

Thr Gln Lys Leu Ala Asp Ala Lys Asp Leu Ser Ile Lys Gln Thr
                        340                 345                 350

Asp Gln Ala Ser Lys Gln Lys Ala Asn Asp Asp Ala Gln Asn Ala Leu
                        355                 360                 365

Ser Ser Ala Asn Gln Val Leu Val Ala Ala Gln Asn Asp Val Lys Asp
                        370                 375                 380

Lys Thr Ala Thr Ala Gln Glu Ala Asn Asp Asn Leu Thr Thr Ala Gln
        385                 390                 395                 400

Asn Asp Leu Ala Thr Leu Gln Asn Gln Leu Ser Ala Asp Gln Ala Asn
                        405                 410                 415

Gln Lys Gln Ala Gln Thr Thr Phe Asp Ser Phe Asp Ala Asp Leu Ala
                        420                 425                 430

Thr Lys Gln Ala Asn Leu Gln Lys Ala Thr Asp Ser Leu Lys Ala Glu
                        435                 440                 445

Gln Gly Arg Leu Ala Ile Ala Gln Ala Asp Leu Asp Asn Ala Asn Lys
                        450                 455                 460

Ala Leu Ser Asp Ala Asn Asn Asn Leu Ala Gln Lys Lys Gln Val Val
        465                 470                 475                 480

Glu Asn Asp Asn Glu Thr Leu Lys Val Asp Asn Asp Lys Leu Val Gln
                        485                 490                 495

Leu Gln Asn Asn Leu Ser Asp Leu Gln Asn Ala Pro Lys Leu Leu Ala
                        500                 505                 510

Ala Ala Lys Glu Gln Val Ala Thr Ala Gln Lys Ala Leu Ala Asp Ala
                        515                 520                 525

Gln Glu Ala Tyr Asn Val Ala Asn Asp Lys Leu Thr Ser Leu Lys Gln
                        530                 535                 540

Thr Ala Ala Gly Thr Thr Thr Asn Val Ser Lys Ala Gln Gln Ala Leu
        545                 550                 555                 560

Ala Glu Ala Lys Asn Asn Glu Asp Ala Ala Lys Glu Val Leu Asp Gln
                        565                 570                 575

Ala Gln Gln Ala Leu Thr Glu Leu Arg Gln Lys Glu Ala Leu Ala Lys
                        580                 585                 590

Gln Val Ala Glu Glu Gln Ala Lys Leu Ala Ala Glu Lys Glu Ala Lys
                        595                 600                 605

Asp Asn Gly Tyr His Ile Glu Asn Asn Gln Val Val Asp Ala Lys Gly
                        610                 615                 620

Asn Ser Val Asn Gly Trp Thr Val Lys Gly Asn Gln Ile Val Ser Pro
        625                 630                 635                 640

Thr Asn Ala Thr Val Asp Pro Ala Val Ser Val Thr Asn Val Asn
                        645                 650                 655
```

```
Val Asp Ser Lys Gly Gln Val Gln Pro Gln Thr Ser Val Thr Ala Asn
            660                 665                 670

Ser Val Lys Thr Val Ala Ala Thr Glu Ser Ala Asn Pro Val Ala Thr
        675                 680                 685

Thr Thr Val Gln Thr Arg Glu Gln Tyr Lys Gln Leu Lys Ser Asn
    690                 695                 700

Asn Gln Leu Pro Gln Thr Gly Asn Asn Asp Ser Ala Val Leu Ser Leu
705                 710                 715                 720

Ala Gly Val Ala Leu Ala Ala Met Leu Ser Leu Phe Gly Ile Lys Lys
                725                 730                 735

Arg Glu Tyr

<210> SEQ ID NO 22
<211> LENGTH: 185
<212> TYPE: DNA
<213> ORGANISM: Artificial Sequence
<220> FEATURE:
<223> OTHER INFORMATION: Based on Lactobacillus reuteri sequence

<400> SEQUENCE: 22
aaattaaaag ctggatttt ttcggccttt ttttagtgca ataattatt ttttacgtat      60 ttatattata gggctaatca ctaaactaat aattagtggt tgaagcgctg aaaattttct   120
gctattttat taatagtttg ataataaaat aatgatattt aatataaaga gggataaacg   180
aaata                                                               185

<210> SEQ ID NO 23
<211> LENGTH: 275
<212> TYPE: DNA
<213> ORGANISM: Artificial Sequence
<220> FEATURE:
<223> OTHER INFORMATION: Based on Lactobacillus reuteri sequence

<400> SEQUENCE: 23
gaagtacaaa gttactttaa ctataatgaa aaacaagaca atataaagaa aacaacatat    60
aaggttcagt tcataactga ttagatttat aataaatatt gtaaatcgga caaaaataaa   120
ttaattttca attaattcaa aaaaaccata ttttttttcgt tttggcatat ttggatttgc   180
tacactaaag atgatcaaga aaggggaaaa gataatcttc aatcttgtgt acttagtttg   240
ttaattaatt tataaattta gggaggaaac ctatc                              275

<210> SEQ ID NO 24
<211> LENGTH: 313
<212> TYPE: DNA
<213> ORGANISM: Artificial Sequence
<220> FEATURE:
<223> OTHER INFORMATION: Based on Lactobacillus reuteri sequence

<400> SEQUENCE: 24
gcaatgcaca agatgctgaa acaaaggcac aacaaaatgc agatcaagct tcaccagcta    60
atattcaaaa ggcacaagat gctattgcta atcaagaaac tcaaattagt aaagacaccg   120
atgctattaa tgacgctaac aaagccgtta gcgatgcaca agcacagtt gatgcagcgc    180 aaaaaaagtt aatgatgcaa ctactgctcg tgacaatcaa caaagaatg ttgatactgc    240 tagtgatgca gttaagaatg ctcaagctat tcttgacaac agtgatcagg ctaaaaagga   300
agcccaagat gct                                                      313
```

<210> SEQ ID NO 25
<211> LENGTH: 527
<212> TYPE: DNA
<213> ORGANISM: Artificial Sequence
<220> FEATURE:
<223> OTHER INFORMATION: Based on Lactobacillus reuteri sequence

<400> SEQUENCE: 25

```
gccgcgggtg cctatacatg cagtcgtacg cactggccca actgattgat ggtgcttgca      60
cctgattgac gatggatcac cagtgagtgg cggacgggtg agtaacacgt aggtaacctg     120
ccccggagcg ggggataaca tttggaaaca gatgctaata ccgcataaca acaaaagcca     180
catggctttt gtttgaaaga tggctttggc tatcactctg ggatggacct gcggtgcatt     240
agctagttgg taaggtaacg gcttaccaag gcgatgatgc atagccgagt tgagagactg     300
atcggccaca atggaactga gacacggtcc atactcctac ggaggcagc agtagggaat      360 cttccacaat gggcgcaagc ctgatggagc aacaccgcgt gagtgaagaa gggtttcggc     420
tcgtaaagct ctgttgttgg agaagaacgt gcgtgagagt aactgttcac gcagtgacgg     480
tatccaacca gaaagtcacg gctaactacg cccccacca gccccaa                    527
```

<210> SEQ ID NO 26
<211> LENGTH: 531
<212> TYPE: DNA
<213> ORGANISM: Artificial Sequence
<220> FEATURE:
<223> OTHER INFORMATION: Based on Lactobacillus reuteri sequence

<400> SEQUENCE: 26

```
tgctggggtt tgcctataca tgcagtcgta cgcactggcc caactgattg atggtgcttg      60
cacctgattg acgatggatc accagtgagt ggcggacggg tgagtaacac gtaggtaacc     120
tgccccggag cggggggataa catttggaaa cagatgctaa taccgcataa caacaaaagc    180
cacatggctt tgtttgaaa gatgctttg gctatcactc tgggatggac ctgcggtgca      240
ttagctagtt ggtaaggtaa cggcttacca aggcgatgat gcatagccga gttgagagac     300
tgatcggcca caatggaact gagacacggt ccatactcct acgggaggca gcagtaggga     360
atcttccaca tgggcgcaa gcctgatgga gcaacaccgc gtgagtgaag aagggtttcg      420
gctcgtaaag ctctgttgtt ggagaagaac gtgcgtgaga gtaactgttc acgcagtgac     480
ggtatccaac cagaaagtca cgactaacta cgccccacac cccagccgca a              531
```

<210> SEQ ID NO 27
<211> LENGTH: 165
<212> TYPE: DNA
<213> ORGANISM: Artificial Sequence
<220> FEATURE:
<223> OTHER INFORMATION: Based on Lactobacillus reuteri

<400> SEQUENCE: 27

```
atggatatga aaataaaaaa agaaccacca caacaagtaa aattagttga agtaattcag      60
gttataacct ctcgtggagc tggaacaaag gaggatccga taagaaagat tattcagtat     120
tggagcaaag aaggcacatt attagcagaa agttttggaa actaa                     165
```

<210> SEQ ID NO 28
<211> LENGTH: 129
<212> TYPE: DNA
<213> ORGANISM: Artificial Sequence
<220> FEATURE:
<223> OTHER INFORMATION: Based on Lactobacillus reuteri

<400> SEQUENCE: 28

| atggctggta tcaaaagtat cgcaaaagcg taatgaccc agaatcactt cgtgatcgcc | 60 |
| gaggcaaagc taagccagaa gagaagtgga cggaagttga ccgactcaag gcagaaaatc | 120 |
| gcttattaa | 129 |

<210> SEQ ID NO 29
<211> LENGTH: 117
<212> TYPE: DNA
<213> ORGANISM: Artificial Sequence
<220> FEATURE:
<223> OTHER INFORMATION: Based on Lactobacillus reuteri

<400> SEQUENCE: 29

| atggctaaat acactgttga attaagtgaa gaagatatcc aaatgatcaa ggattgtcat | 60 |
| tcaaagaatc cttctatcat gaaggcaatg aacgacgcta aaaaagttga agattaa | 117 |

<210> SEQ ID NO 30
<211> LENGTH: 6789
<212> TYPE: DNA
<213> ORGANISM: Artificial Sequence
<220> FEATURE:
<223> OTHER INFORMATION: Based on Lactobacillus reuteri

<400> SEQUENCE: 30

| gtggatgcgg attcgctggc actcgttgat gcactttcac ttgcgctcgt tgatgccgat | 60 |
| tcactggcac tcgttgatgc actttcgcta gcactagtag aagctgactc acttgcactt | 120 |
| gtcgatgccg attcgcttgc acttgtcgat gctgattcgc ttgcgctcgt tgaggctgat | 180 |
| tcgctagcac tagtagaagc tgattcactg gcactcgttg aggcactttc acttgcgctt | 240 |
| gttgaagccg actcacttgc gctcgttgat gcactttcgc tggcacttgt cgatgccgat | 300 |
| tcacttacgc tcgttgaggc cgattcgctg acactcgttg atgcactttc acttacgctc | 360 |
| gttgaggccg attcgctgac actcgttgat gcactttcac ttacgctcgt tgaggccgat | 420 |
| tcgctgacac tcgttgatgc actttcgctg gcacttgtcg aggcactttc acttacgctc | 480 |
| gttgaggccg attcacttac gctcgttgag gccgattcac ttgcgcttgt ggatgcggac | 540 |
| tcacttgcac tcgttgaggc actttcactt gcacttgtcg atgcagattc gctggcactc | 600 |
| gttgatgcac tttcacttgc actcgttgat gcactttcac ttgcacttgt cgatgcggat | 660 |
| tcacttgcac ttgttgaagc ggattcgcta gcacttgtcg atgcggattc acttgcgctt | 720 |
| gttgaagcgg attcgctggc gcttgttgaa gccgactcac ttgcactcgt tgaggctgat | 780 |
| tcacttgcac tcgttgaggc actttcgctg gcgctcgttg atgcagattc gctggcactc | 840 |
| gttgaggccg attcgctggc gcttgttgag gccgattcgc ttgcacttgt cgatgctgat | 900 |
| tcacttgcac tggttgaagc agattcgctg gcactcgttg aggcactttc gctggcactc | 960 |
| gttgaggccg attcacttgc gcttgttgaa gctgattcac ttgcacttgt cgatgctgat | 1020 |
| tcacttgcgc tagtagatgc cgattcgctg gcactcgttg aagcagattc acttgcgctt | 1080 |
| gttgaagccg attcacttgc gcttgttgaa gccgactcac ttgcactcgt tgaggcactt | 1140 |
| tcgctggcgc tcgttgaagc agattcgctg gcactcgttg aagcagattc gctggcgctt | 1200 |
| gttgaggccg attcgcttgc acttgtcgat gctgattcac ttgcactggt tgaagcagat | 1260 |
| tcgctggcac tcgttgaggc actttcgctg gcactcgttg aggccgattc acttgcgctt | 1320 |
| gttgaagctg attcacttgc acttgtcgat gctgattcac ttgcgctagt agatgccgat | 1380 |
| tcgctggcac tagtagaagc agattcactt gcgcttgttg aagccgattc acttgcgctt | 1440 |

```
gttgaagccg actcacttgc actcgttgat gccgattcac ttgcacttgt ggatgcggac    1500
tcacttgcac tcgttgatgc actttcactt gcacttgtgg atgcggattc gctggcactc    1560
gttgatgcac tttcacttgc gctcgttgat gccgattcac tggcactcgt tgatgcactt    1620
tcgctagcac tagtagaagc tgactcactt gcacttgtcg atgccgattc gcttgcactt    1680
gtcgatgctg attcgcttgc gctcgttgag gctgattcgc tagcactagt agaagctgat    1740
tcactggcac tcgttgaggc actttcactt gcgcttgttg aagccgactc acttgcgctc    1800
gttgatgccg attcactggc actcgttgag gcactttcac ttgcgcttgt gaagccgac     1860 tcacttgcgc tcgttgatgc actttcgctg gcacttgtcg atgccgattc acttgcgctt    1920
gtggatgcgg actcacttgc actcgttgaa gccgattggc ttgcactagt agaagctgat    1980
tcactggcgc tcgttgaggc tgattcgctg gcgctcgttg aggctgattc actggcactc    2040
gttgaggccg attcgctggc gctcgttgat gcagattcgc tggcactagt agaagctgat    2100
tcactggcgc tcgttgatgc cgattcactt gcacttgtcg atgcggactc acttgcactc    2160
gttgatgcac tttcgcttgc acttgtggat gcggattcgc tggcactcgt tgatgcactt    2220
tcgctagcac ttgtcgatgc cgattcactt gcactcgttg atgcacttc gctagcactc     2280 gttgatgcac tttcacttgc acttgtggat gcggattcgc tggcacttgt tgatgcggac    2340
tcacttgcac ttgttgaagc cgattcactg gcgctcgttg atgccgattc acttgcactt    2400
gtcgatgccg attcactggc gcttgttgat gcggactcac ttgcactcgt tgatgcactt    2460
tcacttgcac ttgtggatgc ggattcgctg gcactagtag aagctgactc acttgcactt    2520
gtcgatgccg attcactggc actcgttgaa gcactttcac ttgcgcttgt tgatgcggac    2580
tcacttgcac tcgttgaagc cgattcgcta gcacttgtcg aagctgattc actggcgctc    2640
gttgatgctg attcactggc gcttgttgaa gccgactcac ttgcgctcgt tgatgcactt    2700
tcacttgcgc tcgttgatgc cgattcacta gcactagtag aagctgattc actggcgctt    2760
gttgatgcag attcgctggc acttgtcgat gccgattcgc tagcactagt agaagctgat    2820
tcactggcgc ttgttgatgc agattcgctg gcacttgtcg atgccgattc gctagcacta    2880
gtagaagctg attcacttgc acttgtcgat gccgattcac tggcgctcgt tgatgccgat    2940
tcgctggcac tagtagaagc tgactcactt gcacttgtcg atgccgattc actggcactc    3000
gttgatgcac tttcgctagc acttgtagat gcggattcac ttgcactcgt tgatgcactt    3060
tcactggcac tcgttgatgc actttcgcta gcactcgttg aagcactttc acttgcgctt    3120
gttgatgcgg attcgctggc actcgttgat gcactttcac ttgcgctcgt tgatgccgat    3180
tcacttgcgc ttgtggatgc ggactcactt gcactcgttg atgcactttc gcttgcactt    3240
gtggatgcgg attcgctggc actagtagaa gcagattcac ttgcgctcgt tgatgccgat    3300
tcacttgcgc ttgtggatgc ggactcactt gcactcgttg atgcactttc acttgcactt    3360
gtggatgcgg attcgctggc actagtagaa gctgactcac ttgcactcgt tgaagcactt    3420
tcacttgcgc ttgtggatgc ggactcactt gcacttgtcg atgctgattc gctagcacta    3480
gtagaagctg attcacttgc actcgttgat gcactttcac ttgcgcttgt tgaagccgac    3540
tcacttgcgc tcgttgatgc cgattcactt gcactcgtta aggcactttc acttgcgctt    3600
gttgaagccg actcacttgc gctcgttgat gcactttcgc tggcacttgt cgatgccgat    3660
tcgctggcac tagtagatgc ggactcactt gcgctcgtta agccgattg gcttgcacta     3720 gtagaagctg attcactggc gctcgttgag gctgattcac tggtactcgt tgatgcactt    3780
```

```
tcgctagcac tcgttgaagc actttcactt gcgcttgtgg atgcggactc acttgcacta   3840
gtagaagcag attcacttgc gctcgttgat gccgattcac ttgcacttgt cgatgccgat   3900
tcacttgcgc ttgtggatgc ggactcactt gcactcgttg atgcactttc gcttgcactt   3960
gtggatgcgg attcgctggc actagtagaa gcagattcac tggcgctcgt tgatgccgat   4020
tcacttgcac ttgtcgatgc cgattcactt gcactcgttg atgcactttc actggcactc   4080
gttgatgcac tttcgctagc actcgttgaa gcactttcac ttgcgcttgt tgatgcggac   4140
tcacttgcac ttgttgaagc cgattcactg gcgctcgttg atgcactttc acttgtgctt   4200
gttgaagccg actcacttgc gctcgttgat gcacttttcac ttgcgctcgt tgatgccgat   4260
```

```
tcactggcgc ttgttgaagc cgactcactt gcgctcgttg atgcactttc acttgcgctc    6240
gttgatgccg attcactagc actagtagaa gctgattcac tggcgcttgt cgatgccgat    6300
tcgctagcac ttgtcgaagc tgattcactt gcactcgttg atgctgattc acttgcactt    6360
gtcgatgctg attcacttgc gctcgttgat gctgattcgc tggcacttgt cgatgccgat    6420
tcacttgcgc ttgttgaagc tgattcactt gcgcttgttg atgcggattc gcttgcactc    6480
gttgatgcac tttcacttgc gctcgttgat gccgattcgc tggcgctcgt tgatgcactt    6540
tcacttacgc tcgttgatgc actttcactt acgctcgttg atgcactttc acttacgctc    6600
gttgatgcac tttcacttac gctcgttgat gcactttcac ttacgctttt tgatgccgat    6660
tcgctggcac tcctcgttga agcggattcg ctggcactcc tcgttgaagc ggattcactt    6720
acgctcgttg atgcgctagt cgaagtactc gtcgaggtgg attcctgttc actcttactc    6780
gtcaattga                                                            6789

<210> SEQ ID NO 31
<211> LENGTH: 132
<212> TYPE: DNA
<213> ORGANISM: Artificial Sequence
<220> FEATURE:
<223> OTHER INFORMATION: Based on Lactobacillus reuteri

<400> SEQUENCE: 31
atggagatat tggtaacgtt atttgatttg gtgtttttta ttacgtttat agtcgcaatt     60
gtctatggta ttaggtggtt taaaggaaga aagataaag aaaatgaatc tcttaagaaa    120
cgccgtttgt aa                                                        132

<210> SEQ ID NO 32
<211> LENGTH: 240
<212> TYPE: DNA
<213> ORGANISM: Artificial Sequence
<220> FEATURE:
<223> OTHER INFORMATION: Based on Lactobacillus reuteri

<400> SEQUENCE: 32
atgattaact taaacttagc aggcttagat tttgtaatga cggcactttt tattgtgttg     60
tttacagaac agttgaaaaa tgcccgaact cagcgtgatg ctctgattgg tttagcattt    120
gcaattattt gtttactatt ttgcaacaag aatgttttc tattagtgac attagtaaca    180
cttgtcgcac tgttttcatt aaattactta atcacgagga gaaaaaatga cattaactga    240

<210> SEQ ID NO 33
<211> LENGTH: 123
<212> TYPE: DNA
<213> ORGANISM: Artificial Sequence
<220> FEATURE:
<223> OTHER INFORMATION: Based on Lactobacillus reuteri

<400> SEQUENCE: 33
atgtcagaga tgaaaaatcg cgtaattaat tttcggaatg ataacttagc caaacttata     60
gtcaattatt atggaaatag tcaattaagt gtgcatatta ctaataatat gttttttgaa    120
tga                                                                  123

<210> SEQ ID NO 34
<211> LENGTH: 786
<212> TYPE: DNA
<213> ORGANISM: Artificial Sequence
<220> FEATURE:
```

<223> OTHER INFORMATION: Based on Lactobacillus reuteri

<400> SEQUENCE: 34

| | |
|---|---|
| atgaaacgca aaattgcatt agctcaactt gatattcaat taggaaatcc tgccgaaaat | 60 |
| tatcaaaaag ctaaacaagc gattgaagaa gctgctagtc accatgcaga tatcgttgtc | 120 |
| ttgccggaga tgtggaatgc tggctatgcc ttagatcaat tagcagaatt ggcagatgaa | 180 |
| aacggtcaaa agacacaaaa atttcttagt gagttagcgt tagaaaatca aattaacatt | 240 |
| gtcggtggtt cagtagcggt gagatgtgga caatcttttt tcaatacaac ctatgtttat | 300 |
| gatcaaaagg gaaatctaat tagcagttac gagaaggtgc atttatttgg actaatgaat | 360 |
| gaagaccgat atctaaaagc cgggcaaaaa gaaaatcact ttgaattagc tggggttccg | 420 |
| agtgcaagtt ttatttgtta tgatttgcga ttccctgaat ggattagaac agtcactcgt | 480 |
| tatggaactg atatcttata tttttcggca gaatggccaa gcaaacggat aaacaatgg | 540 |
| aaaataatgc ttcagtcacg ggcaattgaa aatcaagcct ttgtagtcgc ggtcaatcgt | 600 |
| gttgggacgg atttagagaa tagctttaat ggtcattcgt tagtaataga tccgcttggg | 660 |
| cagattatcc atgatgcagg agaagttgaa caagtaagtt atgcagaaat tgacttagcg | 720 |
| cagttagcac aggttcgggg gccgattccg gtgtttaagg atcgccgacc aagtctttat | 780 |
| cattaa | 786 |

<210> SEQ ID NO 35
<211> LENGTH: 504
<212> TYPE: DNA
<213> ORGANISM: Artificial Sequence
<220> FEATURE:
<223> OTHER INFORMATION: Based on Lactobacillus reuteri

<400> SEQUENCE: 35

| | |
|---|---|
| atgcaaaata aagatgcttg tacatcaatt atggtcggta aaaaggcttc tctcgacggt | 60 |
| gctaattata ttgctcgtaa tgaagatcgc gtaaaagcaa ttgaacccaa gcgattttta | 120 |
| gtaaaaccgg cagtaaaagg acgccacgaa acctacgtat caccttacaa taaagtaact | 180 |
| gtagctttgc cggaagagag aatgcgttat acttctacgc ctacccttga tcaaacagcc | 240 |
| ggacctaatg aagaagatgg aattaatgaa gcaaatgtgg cagcttcctt tactgagagt | 300 |
| gtttatgcaa atgatcgggt gttagcatat gatccatacg taaaaaatgg cctggcagaa | 360 |
| gactcacttt gtactttagt attaccgtat attcattctg cccgtgaagg agttgaatat | 420 |
| actggaaaat taattgctga attgggctct gctgagggaa atggaatgca atttgcagat | 480 |
| gcagatgata tttggtatat gtaa | 504 |

<210> SEQ ID NO 36
<211> LENGTH: 1533
<212> TYPE: DNA
<213> ORGANISM: Artificial Sequence
<220> FEATURE:
<223> OTHER INFORMATION: Based on Lactobacillus reuteri

<400> SEQUENCE: 36

| | |
|---|---|
| atgaattatt ttatcggtgt tgatgttgga actacttcta caaaggcagt tctatatgac | 60 |
| caaaatgcaa ctgtgttaga tcaatttagc caaggttatt cccttaccg cgatgctagt | 120 |
| ggaatggctg aacaaaaccc aactgcaatt gtcgaagcag tcgaaaaagt tattcatgat | 180 |
| gcagcacaaa aagcagattt aacaaatgga aaattgttag cggtatcatt ttctagtgct | 240 |
| aaccaaagtg tgattatgct cgacaagaat ttcaatcccc tttcacgggt catcacttgg | 300 |

```
gctgataccc gtgcacgtga tgtcgccaac gaattaaaga atagtcctgc tggtcagcaa      360
atctatgcta aaacaggtac acctattcat ccaatgtccc cattgaccaa gattatgtgg      420
ctcaataaga cacaagcaga taaggttgct caaactgcat attttggcga tatcaaatcc      480
tacctcttcc accagttttt caatacattt aaggttgatg tttccatcgc ttcatgtacc      540
ggaatgatga atgtcaatac gtgtgactgg gacgatcaag cattggaact cgctaacgtc      600
gactgttccc aattaccaga atcgtgaacg gaacaaccc aagcgattgg cctaacagca      660
gcggcgcaag caaaaatggg tatccccgct gacacgccat tgtctatgg tgcctttgac      720 ggtgctttat ctaatttagg tgtgggggca attaagcaaa atactgttgc cattacgatt      780
ggaacttcgg ctggtgttcg ggtagtaact gaccatccag tgatcgatcc tcagcaacga      840
ctcttctgtt acgccgtgga taaaggttta tgggtcatcg gcggtccgct taataatggt      900
ggcgatgtct atcagtgggc cgttgaacac ttagttgacg ctagtgcagt taaaaatgaa      960
aatattgatc cctacactct tgctaaccga gttattgaag tgttcccgc cggagctcac     1020 ggtttgctct tccacccatt ccttggcggt gaacgggcac cattatggga cgctaatgcg     1080
cgcggtagtt tctttggact ttcccacatt catactcgtg ccgatatgct gcgctcagta     1140
atggaaggaa tttgtatgaa tattgcaact gttttccaag cggttcgtga tcttgttggt     1200
aatcctgcaa gcgtaactgc aactggcggt tttgcgcgag ctgaagtttg gcggcaaatg     1260
ttagcagatg tcttgaactg tccggtcaat atcccgaact catttgaatc tggttgtctc     1320
ggtgcaatca ccatggcaat gaagagttta ggaatgattg aaaactatga atcattaaa      1380 acattagttg gtgatatcag ttcttatcag ccaaatcaag atgcggttaa tgtttatcaa     1440
aattacttac cactttttaa gcaggtcgaa ggattattaa caccagccta ttcgaccatc     1500
gctaaattac aacaacaatc tactactcat tag                                  1533

<210> SEQ ID NO 37
<211> LENGTH: 195
<212> TYPE: DNA
<213> ORGANISM: Artificial Sequence
<220> FEATURE:
<223> OTHER INFORMATION: Based on Lactobacillus reuteri

<400> SEQUENCE: 37
atgacaacat caatgatcca cagtagaagt atgttggcga aagtgattgc agaatcacct       60
tcacctttta ttataccaat ttttttgtcct aatgtaataa agattatctt tttatctata     120 aattattta tgaaaagagt ggaaaaggca agaagagcaa tcaaaaagcc aattttaaca      180
attttattaa gttga                                                      195

<210> SEQ ID NO 38
<211> LENGTH: 570
<212> TYPE: DNA
<213> ORGANISM: Artificial Sequence
<220> FEATURE:
<223> OTHER INFORMATION: Based on Lactobacillus reuteri

<400> SEQUENCE: 38
atgagcaaac tattacttga tgaaagaccg ttacaagttc aggcatcgtt agctggagcg       60
ttgaaaagct tagacgaagc tgttattctc cagcagcttc actattggct tcaacgttct     120
aatacagtaa agacaatca caaatgggtc tataacagca tggctgattg gaataaacag     180
ttcccttggc tttctagaaa ggctctatcg aaccactta agaaattaga aaacgagga     240
```

```
ctaattatta caggcaacta taataaatta tcttttgaca aaacaaagtg gtatcgaatt      300
gactatgacg catttttccca tttggaacaa cgattgggta gaaactaccc aacgaatggg      360
aagaatctac ccaatggaga cggtaaaaac tgcccaatcg gagaggaaga atctacccaa      420
ccaataccaa tagactacca agagactaca caaaagacta ctacaagaga taaagggcag      480
gcacagccag cccaaccttc cattgctgca cagcggcgag aagttgttga atatctcaat      540
caaaaaaact ggcaagcact tcaagcctga                                       570

<210> SEQ ID NO 39
<211> LENGTH: 438
<212> TYPE: DNA
<213> ORGANISM: Artificial Sequence
<220> FEATURE:
<223> OTHER INFORMATION: Based on Lactobacillus reuteri

<400> SEQUENCE: 39
ttgaataatt ttcaaaaggc aattttcttg ttgcagaata tcgacaagct taaacagctt       60
aatggtaaag cgatgactct tactgagttc tctaaaataa ctgatgtttc acggccaacg      120
ttgtataaat acattcagca tccagaaaca atgagtagtt cgtttgtaaa taaagcggcc      180
atgctctacg acaaggttgt taaatttcaa gatattcttg atacagttca gcgtgaagat      240
aaacaattta agactaccag gcaggaattg attaagcttt tagagtctaa tgtagctaat      300
attgaagtta cagattatac aaaagcaatc gcgacagtaa ttattagtga cttaaaagaa      360
gaaaattcaa gtctgctaaa agcgttaagt aagcaattac catttaaacc aaatttaaat      420
gataatttgt caaaatag                                                   438

<210> SEQ ID NO 40
<211> LENGTH: 333
<212> TYPE: DNA
<213> ORGANISM: Artificial Sequence
<220> FEATURE:
<223> OTHER INFORMATION: Based on Lactobacillus reuteri

<400> SEQUENCE: 40
gtgaagatga atagtatgac aaacaaccaa aaagaaagtt ggaacgttgg caactataaa       60
atcaatgtat taccagatga tgagttccag caattgttaa agaaccaacg ccaacttcaa      120
cagatcattg aaagtatgcc actaccaacc gaccccaatg ttgatctagt taaaaagatt      180
cattcccaac tccctattac aaactgggct tgggaattaa ctaaacaacg agaacatgag      240
gaaaagttaa agaaacaaaa gcagcgaatt gcacagcaat cgcttaacta tccaacaaac      300
ctcaagaaac cggataatgg cctttcccta taa                                  333

<210> SEQ ID NO 41
<211> LENGTH: 153
<212> TYPE: DNA
<213> ORGANISM: Artificial Sequence
<220> FEATURE:
<223> OTHER INFORMATION: Based on Lactobacillus reuteri

<400> SEQUENCE: 41
atgaattcta atttgaaaaa gaatttgatt atcgcaaatg gatttctact actaataata       60
atattttatg ttttattaca tatgggtcca ttaaatatga aagtcttatt agtaggattg      120
gtattaatga atctgacagt aatatttaaa taa                                  153

<210> SEQ ID NO 42
<211> LENGTH: 1395
```

<212> TYPE: DNA
<213> ORGANISM: Artificial Sequence
<220> FEATURE:
<223> OTHER INFORMATION: Based on Lactobacillus reuteri

<400> SEQUENCE: 42

```
atggataaat taacattgaa aaaactaatt attattacat taggcatgct aatggtattt      60
cttttaggta tgcaccttca tcaaaagaca cactttaaca aaaacgtgaa gattaataat     120
attccagtcg gaggtcttac tgttcaacag gcatataata aagtaagtaa tactaaaaga     180
aaatcaaaaa tctacattaa caaaaagtta gtttattcag gtaaaagtac tgactcaggt     240
tttaagttat ctgataaaga aagatttagt aaggcgttac attaccaata cacttttttt     300
ccctcacgaa aacatgaaaa tttgctagtt gagccagctg atttagataa gtcagcgtta     360
aataatattg attcggcaat agtagctagg attcatcagc tcaatatagg cagaaaggcc     420
ccacgtgatg catacgccgt ttaccagaat aataaagttt cagttattcc agcaattgat     480
gggacacgat atagtgaaca aggactttgt aatattgcta ataaggaatt tgttaatggg     540
acaattcatt taactcctaa ggttattact cctttatcgg caaacagtaa agtagttcaa     600
gatgaaaaga acacctgag taaactacaa atcgatcgg ttgtttatca ggttcagaaa      660
acaaaatata atttaaagc gtctaatgtc atttctaaag caacttatca gcatgggaaa      720
taccattttg aaactgacaa cgttaaatcc aagattgcca atataaataa taagcaagca     780
acattaggaa agagctttaa atttagaact gattctggaa aagttatttc tacatctaat     840
cagggaacat atggttggaa aataagtagc aagcaggcag acaaacact ctctaaagcg      900
ttagctaata atgttaagag cgttaatgcc gaaaatgata tttacggtaa aggctatagt     960
catcttggta ctggatattc ggctgtgaat aatcatgggc ttggtaatac ttatgtggct    1020
gtatcattag ctaaacagca tgcttggttt tataaaaatg gaaaatgtgt actgagtaca    1080
gatattgtta gtggatcaga tgacgctaat aataggactc ctaaaggtgt ttggtatatc    1140
atgtatcaac aaacgccatc agttttacgt gggactaatg atgatggttc caagtatagt    1200
agtcctgttc agtattggtc tccgtttact ttatcagggt gtggctttca tgatgctagt    1260
tggaggcata attggtctaa aacagcttat aaacagactc atggtggctc acatggctgt    1320
attaacatgc atccggaaaa tgcaggagac ggtttccatg cccttactaa aggagaaccg    1380
gtaataattt attag                                                    1395
```

<210> SEQ ID NO 43
<211> LENGTH: 1932
<212> TYPE: DNA
<213> ORGANISM: Artificial Sequence
<220> FEATURE:
<223> OTHER INFORMATION: Based on Lactobacillus reuteri

<400> SEQUENCE: 43

```
atgcaattaa accataaatt aggagttttc ttggcagcgc catttgctct actggtttta      60
tcagctacaa acgtgcatgc cgataacatt caaagtaata gtaaccagac aatcagtaat     120
atgagtttgc aaactaatga cacaaagact caacaaaatg ttgtaatgtc aaacgatgca     180
aaagctcaaa ttactgtaaa tcctagttct aatgctaatt ctagttctgt agcaaagata     240
aatgaaaaga ataatgtaaa atcggatact gacaatacta atgtcgaatc aaatgctgat     300
aatattggga cattgcttc tagcgattcc acggcagtgg ctaattctgc tagttccgat     360
aatattcagt catttaacgt aaatacgcag gaacagcctg caataaatgt atctgaacta     420
```

-continued

```
acaaccgaag agtatgttac gaattacact caacaacaga tcaataatgc gacgactatt    480
catgattact ttataaatca aggatggaca ccaaatgcta ttgctggaat gcttggtaac    540
tttgtttcag agtcaggttt aatcccagac ttacatcaat atggtggtgg gcctggttat    600
gggttagctc aatggccatt taatagtgta gtaaattggt gtcgtaataa tggatatgat    660
tatcgtactt tgcaaggaca atgtgcatat attgaatatc aaatgactca tggacagcag    720
tattatccat cagcttactc tagaatgacc gctaatgaat atatgcatag ttatgcttca    780
gcatatactt taggtatgat ttggcttaat aactttgagc gacctgcaaa taggaatcag    840
ccagctcgtg gtcaacaggc tcaatactgg tatcagtatt tccaaagtca tggttctaca    900
tcagcaccgg tacaacaaaa tcctagtaca ccagcaacaa ctcctagctc aagtcgaatg    960
agtcaacacg ggacattcaa agttgcttat ggattaaatg tacgccaagc accaagtaca   1020
tcggcagcta ttgtaacgta ttacaatggt ggtcaaagct ttacatatga ttcaaagatt   1080
gaagctaacg ggtatctttg ggtatcatac atgagttata gtggcgtacg tcgttatgtt   1140
gcaattaaga atttgaataa tggaacgact tacggttatg attcgaataa cttctcatac   1200
agtgctcctg catcttcaac accatctact aatgtgccaa gtacgccagc accaagtaca   1260
tctacttcat caactgagaa gcaatatgga acattcaaag ttgcttatgg attaaatgta   1320
cgccaagcac caagtacatc ggcagctatt gtaacgtatt acaatggtgg tcaaagcttt   1380
acatatgatt caaagattga agctaatggg tatctttggg tatcatacat gagttatagt   1440
ggcgtacgtc gttatgttgc gattaagaat ttgagtaatg gaacaactta cggttacgat   1500
tcaaataact tttcatttaa tgggactcca gtaacatcaa ataataatcc ttctagtact   1560
ccggcagttc cgcaaggtaa taagggccaa caagttgttg ctcttgcacg tcaacaaata   1620
ggtaaacctt atgtttgggg agcaaccggt cctaattcgt ttgattgttc aggactcgtg   1680
cagtatgttt atcgtcaagt tggtgttaac ttaccacgga ctacaactca acaagaatat   1740
tgtggacatg ctgtaagctt taataatctt caacctggag atctaatgtt ctggggaaag   1800
tatggtagtg catatcacgt tggaatctat accggaaacg gtaatgtttt atttgcaccg   1860
caacctggtc aaacagttaa ggaacaacca atgcgctatt acatgcctgc ctttgcaaga   1920
agagtattgt aa                                                      1932
```